US008470817B2

(12) United States Patent
Sudhakar

(10) Patent No.: US 8,470,817 B2
(45) Date of Patent: Jun. 25, 2013

(54) COMPOUNDS AND METHODS FOR TREATMENT OF CANCER

(75) Inventor: Anantha Sudhakar, Fremont, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 141 days.

(21) Appl. No.: 12/912,617

(22) Filed: Oct. 26, 2010

(65) Prior Publication Data

US 2011/0105497 A1    May 5, 2011

Related U.S. Application Data

(60) Provisional application No. 61/255,039, filed on Oct. 26, 2009.

(51) Int. Cl.
```
A61K 31/5355   (2006.01)
A61K 31/497    (2006.01)
A61K 31/4436   (2006.01)
A61K 31/426    (2006.01)
C07D 413/14    (2006.01)
C07D 417/14    (2006.01)
```

(52) U.S. Cl.
USPC ............... 514/233.8; 514/253.04; 514/300; 514/365; 544/127; 544/362; 546/123; 548/181

(58) Field of Classification Search
USPC .......... 514/233.8, 253.04, 300, 365; 544/127, 544/362; 546/123; 548/181
See application file for complete search history.

(56) References Cited

U.S. PATENT DOCUMENTS

| | | |
|---|---|---|
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 4,810,643 A | 3/1989 | Souza |
| 4,999,291 A | 3/1991 | Souza |
| 5,059,595 A | 10/1991 | Le Grazie |
| 5,073,543 A | 12/1991 | Marshall et al. |
| 5,120,548 A | 6/1992 | McClelland et al. |
| 5,229,496 A | 7/1993 | Deeley et al. |
| 5,318,965 A | 6/1994 | Chu et al. |
| 5,354,556 A | 10/1994 | Sparks et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,591,767 A | 1/1997 | Mohr et al. |
| 5,612,059 A | 3/1997 | Cardinal et al. |
| 5,624,924 A | 4/1997 | Chu et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,817,669 A | 10/1998 | Tomita et al. |
| 5,817,996 A | 10/1998 | Ulrich et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |

(Continued)

FOREIGN PATENT DOCUMENTS

| | | |
|---|---|---|
| JP | 11-349565 | 6/1998 |
| JP | 2003/127542 | 5/2003 |

(Continued)

OTHER PUBLICATIONS

Platinol Prescribing Information, Jul. 2010, pp. 1-15.*
Taxol Prescribing Information, Apr. 2011, pp. 1-53.*
Emens, et al., Curr. Opinion Mol. Ther., 2001, 3(1): 77-84.
Kumar et al., Tet. Lett., 2003, 44: 5687-5689.
Ma, et al., CA Cancer J. Clin., 2009, 59 (2) 111-37.
Penichet, et al., J. Immunol. Methods, 2001, 248:91-101.
Santus, et al., J. Controlled Release, 1995, 35: 1-21.
Therasse, J. Nat'l. Cancer Institute, 2000, 92(3): 205-216.
Tsuzuki, et al., J. Med. Chem., 2004, 47:2097-2106.
Tomita, et al., J. Med. Chem., 2002, 45:5564-5575.
Tsuzuki et al., Tet. Asym., 2001, 12: 2989-2997.
Tsuzuki et al., Tet. Asym., 2001, 12: 1793-1799.
Verma, et al., Drug Development and Industrial Pharmacy, 2000, 26, 695-708.
Verma, et al., J. Controlled Release, 2000, 79, 7-27.

*Primary Examiner* — Joseph Kosack
(74) *Attorney, Agent, or Firm* — Jones Day

(57) ABSTRACT

Compounds for treating, preventing or managing cancer are disclosed. Also provided are methods for using the compounds in treatment of various cancers. Also provided are methods of treatment using the compounds together with another chemotherapy, radiation therapy, hormonal therapy, biological therapy, or immunotherapy. Pharmaceutical compositions suitable for use in the methods are also disclosed.

19 Claims, 44 Drawing Sheets

U.S. PATENT DOCUMENTS

Figure 1:
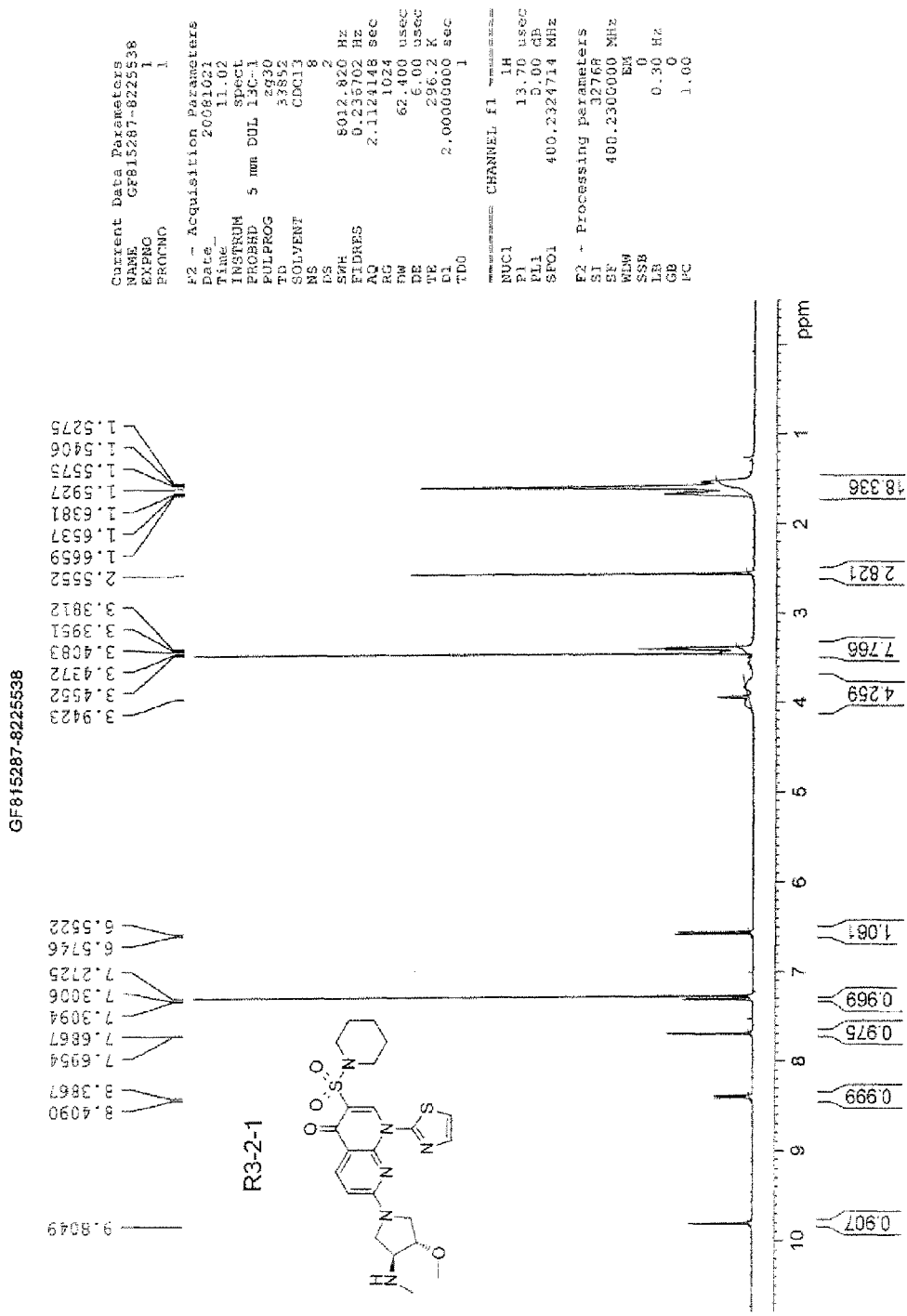

| | | |
|---|---|---|
| 6,274,552 B1 | 8/2001 | Tamarkin et al. |
| 6,316,652 B1 | 11/2001 | Steliou |
| 6,350,458 B1 | 2/2002 | Modi |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 7,163,948 B2 | 1/2007 | Whitten et al. |
| 2005/0004160 A1 | 1/2005 | Whitten et al. |
| 2005/0124604 A1 | 6/2005 | Sircar et al. |
| 2005/0203120 A1 | 9/2005 | Adelman et al. |
| 2005/0215583 A1 | 9/2005 | Arkin et al. |
| 2006/0025437 A1 | 2/2006 | Adelman et al. |
| 2006/0264634 A1 | 11/2006 | Whitten et al. |
| 2007/0249611 A1 | 10/2007 | Feng et al. |
| 2008/0063642 A1 | 3/2008 | Adelman et al. |
| 2008/0306093 A1 | 12/2008 | Servant et al. |
| 2009/0263393 A1 | 10/2009 | Adelman et al. |
| 2010/0029708 A1 | 2/2010 | Adelman et al. |
| 2010/0048609 A1 | 2/2010 | Jacobs |
| 2010/0203162 A1 | 8/2010 | Sudhakar et al. |
| 2010/0297142 A1 | 11/2010 | Silverman |
| 2011/0008371 A1 | 1/2011 | Michelson et al. |

FOREIGN PATENT DOCUMENTS

| | | |
|---|---|---|
| WO | WO 02/17918 | 3/2002 |
| WO | WO 2004/091504 | 10/2004 |
| WO | WO 2010/099526 | 2/2010 |

* cited by examiner

COMPOUNDS AND METHODS FOR TREATMENT OF CANCER

1. RELATED APPLICATIONS

This application claims priority to U.S. provisional application No. 61/255,039, filed Oct. 26, 2009. The disclosure of the above referenced application is incorporated by reference herein in its entirety.

2. FIELD

Provided herein are compounds of Formula I and Formula II, methods for using the compounds for treating, preventing or managing cancer, and compositions comprising the compounds. Also provided are doses, dosing regimens and dosages for the compounds and compositions provided herein.

3. BACKGROUND

A variety of cancers are described in detail in the medical literature. Examples include bladder cancer, brain cancer, breast cancer, cervical cancer, colon cancer (including colorectal cancer), esophageal cancer, head and neck cancer, liver cancer, lung cancer (both small cell and non-small cell), melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, uterine cancer, and hematologic cancers. The incidence of cancer continues to climb as the general population ages, as new cancers develop, and as susceptible populations (e.g., people infected with HIV or excessively exposed to sunlight) grow. However, options for the treatment of cancer are limited. For example, in the case of blood cancers, few treatment options are available, especially when conventional chemotherapy fails and bone-marrow transplantation is not an option. A tremendous demand, therefore, exists for new compounds, compositions, and methods that can be used in treating, preventing, and managing various cancers.

4. SUMMARY

In one embodiment, provided herein are compounds of Formula I:

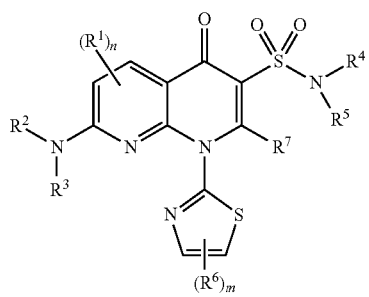

and pharmaceutically acceptable salts, solvates (e.g., hydrates), and clathrates, thereof; wherein
$R^1$ is halo, alkyl, haloalkyl, alkoxy, or hydroxyl;
$R^2$ and $R^3$ together with the nitrogen atom on which they are substituted form a substituted or unsubstituted heterocyclic ring, where substituents when present are selected from one or more $Q^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;
$R^4$ and $R^5$ are selected as follows:
i) $R^4$ and $R^5$ are each alkyl, or
ii) $R^4$ and $R^5$ together with the nitrogen atom on which they are substituted form a substituted or unsubstituted heterocyclic ring; where substituents when present are selected from one or more $Q^2$ groups selected from halo, alkyl, haloalkyl, alkoxy, and hydroxyl;
$R^6$ is halo, alkyl, haloalkyl, alkoxy, or hydroxyl;
$R^7$ is hydrogen, halo, alkyl, haloalkyl, alkoxy, or hydroxyl;
n is 0 to 2;
m is 0 to 2; and
where $Q^1$ is optionally substituted with one, two or three groups selected from halo, alkyl, amino, alkoxy, hydroxyl, and haloalkyl.

In another embodiment, provided herein are compounds of Formula II:

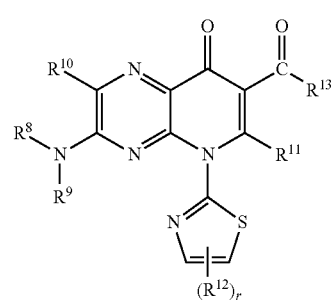

and pharmaceutically acceptable salts, solvates (e.g., hydrates), and clathrates, thereof wherein
where $R^{10}$ and $R^{11}$ are each independently hydrogen, halo, alkyl, haloalkyl, alkoxy, or hydroxyl;
$R^8$ and $R^9$ together with the nitrogen atom on which they are substituted form a substituted or unsubstituted heterocyclic ring, where substituents when present are selected from one or more $Q^3$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;
$R^{12}$ is halo, alkyl, haloalkyl, alkoxy, or hydroxyl;
$R^{13}$ is hydroxyl or alkoxy or $NHR^{14}$, where $R^{14}$ is alkyl, cycloalkyl or aryl;
r is 0 to 2; and
where $Q^3$ is optionally substituted with one, two or three groups selected from halo, alkyl, amino, alkoxy, hydroxyl, and haloalkyl.

Also provided are methods of treating, preventing and managing various cancers. The methods comprise administering to a patient in need of such treatment or management a therapeutically effective amount of a compound of Formula I or Formula II provided herein, or a pharmaceutically acceptable salt, solvate (e.g., hydrate), clathrate, ester, or prodrug thereof. In addition, dosing ranges, dosing regimens, and pharmaceutical doses using the compounds are described.

In certain embodiments, cancers that can be treated, prevented or managed using the compounds and therapeutic methods provided herein include, but are not limited to: bladder cancer, brain cancer, breast cancer, cervical cancer, colon cancer (including colorectal cancer), esophageal cancer, head and neck cancer, leukemia, liver cancer, lung cancer (both small cell and non-small cell), lymphoma, melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. The cancer can be relapsed or refractory or resistant to another treatment.

In certain embodiments, the cancer includes hematologic malignancies, including, but not limited to leukemias, lymphomas, and myeloma. The various forms of leukemias include, but are not limited to, chronic lymphocytic leukemia, chronic myeloid leukemia, acute lymphocytic leukemia, acute myelogenous leukemia, acute myeloblastic leukemia, and hairy cell leukemia. The leukemia can be relapsed or refractory or resistant to another treatment. In certain embodiments, the hematologic malignancy is promyelocytic leukemia, T-cell leukemia, or lymphoblastic leukemia. In certain embodiments, the compounds may be used to treat antecedent hematologic disorders, such as myelodysplastic syndromes.

Further provided are methods of treating, preventing or managing cancer by administering a compound provided herein to a subject in a dose of about 1 mg/m² to 500 mg/m², about 1 mg/m² to 300 mg/m², or 10 mg/m² to 150 mg/m², of a compound of Formula I or Formula II provided herein, on the basis of body surface area. Additional dosing and dosing regimens are described in more detail herein below.

Also provided herein are dosages and dosing regimens for treatment of cancer. The administered dose of a compound of Formula I or Formula II can be delivered as a single dose such as, for example, an intravenous (IV) push of 10-15 minutes duration (e.g., a single bolus injection) or over time such as, for example, a 24-hour period (e.g., continuous infusion over time or divided bolus doses over time). Administration of the compound may be repeated as necessary in the judgment of the medical practitioner, for example, until the patient is adjudged to have stable disease or experiences partial or complete disease regression, or until the patient experiences disease progression or unacceptable toxicity.

In some embodiments, a compound of Formula I or Formula II can be administered to a patient using a cyclic regimen. Cycling therapy involves the administration of the active agent, followed by a rest period, and repeating this administration/rest cycle at least once. Cycling therapy can reduce the development of resistance to one or more of the therapies, avoid or reduce the side effects of one of the therapies, and/or improve the efficacy of the treatment.

In another embodiment, a compound of Formula I or Formula II is administered in combination with another medicine ("second active agent") or another therapy conventionally used to treat, prevent, or manage cancer. Second active agents include known small molecule, anticancer, antitumor, or cytotoxic agents, as well as large molecules (e.g., proteins and antibodies), examples of which are provided herein, as well as stem cells or cord blood. Examples of such conventional therapies include, but are not limited to, surgery, chemotherapy, radiation therapy, hormonal therapy, biological therapy, immunotherapy, blood transfusions, and combinations thereof.

In some embodiments, the second active agent is selected from alkylating agents, antimetabolites, aurora kinase inhibitors, purine antagonists, pyrimidine antagonists, spindle poisons, mitotic inhibitors, topoisomerase II inhibitors and poisons, topoisomerase I inhibitors, anti-neoplastic antibiotics, nitrosoureas, inorganic ion complexes, enzymes, hormones and hormone analogs, EGFR inhibitors, antibodies and antibody derivatives, IMIDs, HDAC inhibitors, Bcl-2 inhibitors, VEGF-stimulated tyrosine kinase inhibitors, VEGFR inhibitors, proteasome inhibitors, cyclin-dependent kinase inhibitors, aromatase inhibitors, dexamethasone, and combinations thereof.

Thus, in certain embodiments, provided herein are combinations for treatment, prevention and management of solid tumors. In other embodiment, provided herein are combinations for treatment, prevention and management of hematologic cancers.

Also provided are pharmaceutical compositions, single unit dosage forms, and dosing regimens which comprise a compound of Formula I or II, and a second, or additional, active agent. Second active agents include specific combinations, or "cocktails," of drugs or therapy, or both.

5. BRIEF DESCRIPTION OF DRAWINGS

FIG. 1 provides an NMR spectrum for the compound of Example 1.

Figure 2:
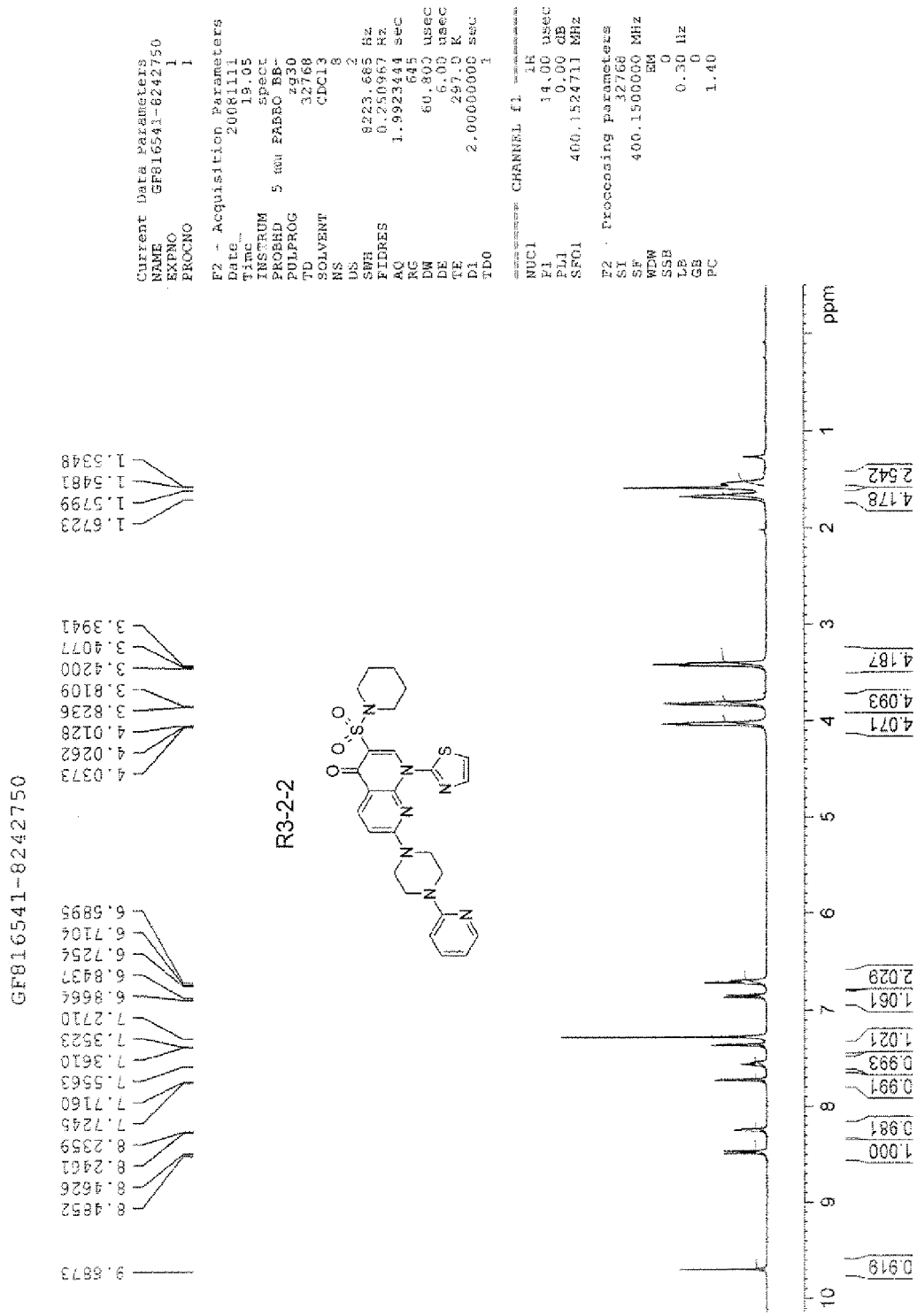

FIG. 2 provides an NMR spectrum for the compound of Example 2.

Figure 3:
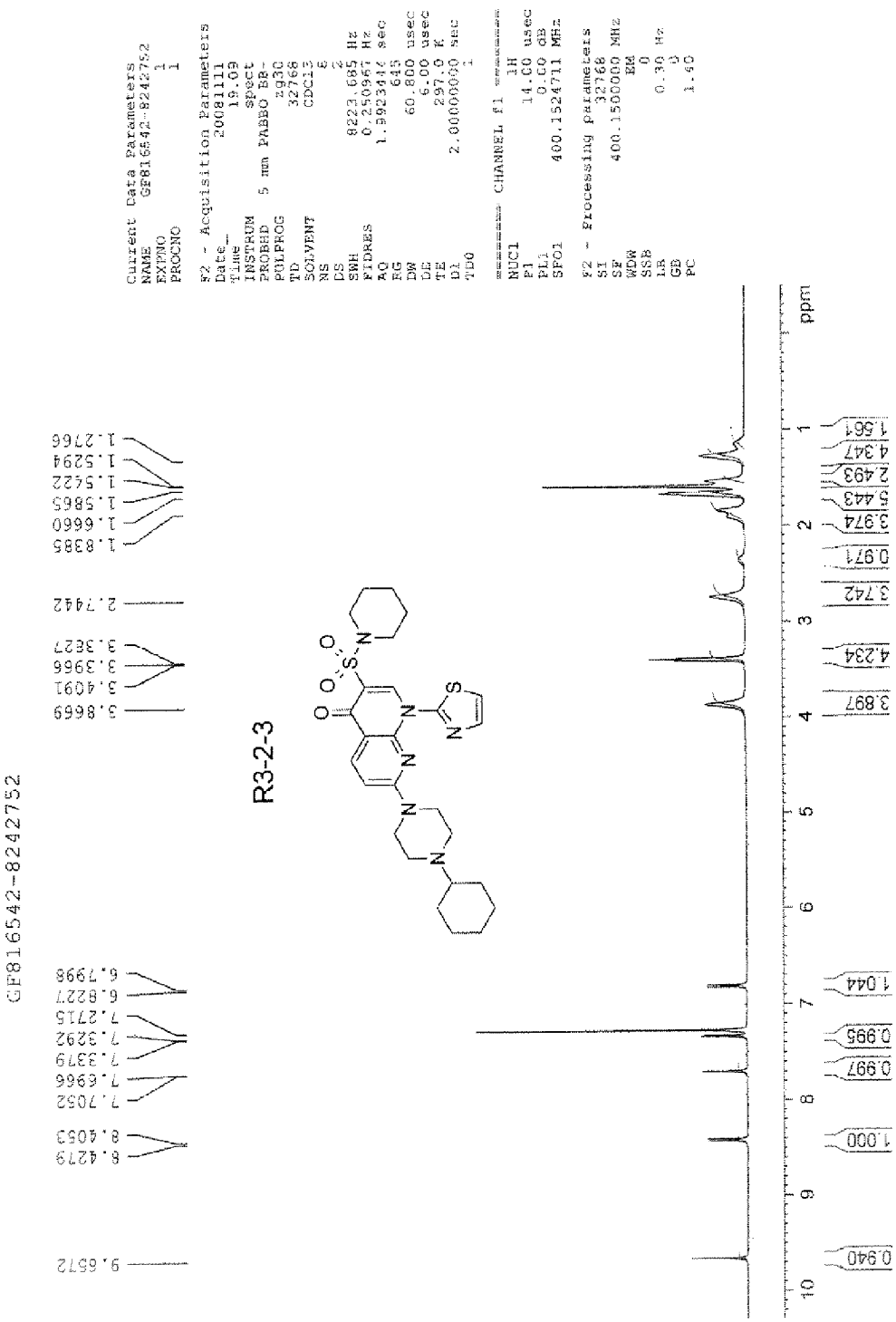

FIG. 3 provides an NMR spectrum for the compound of Example 3.

Figure 4:
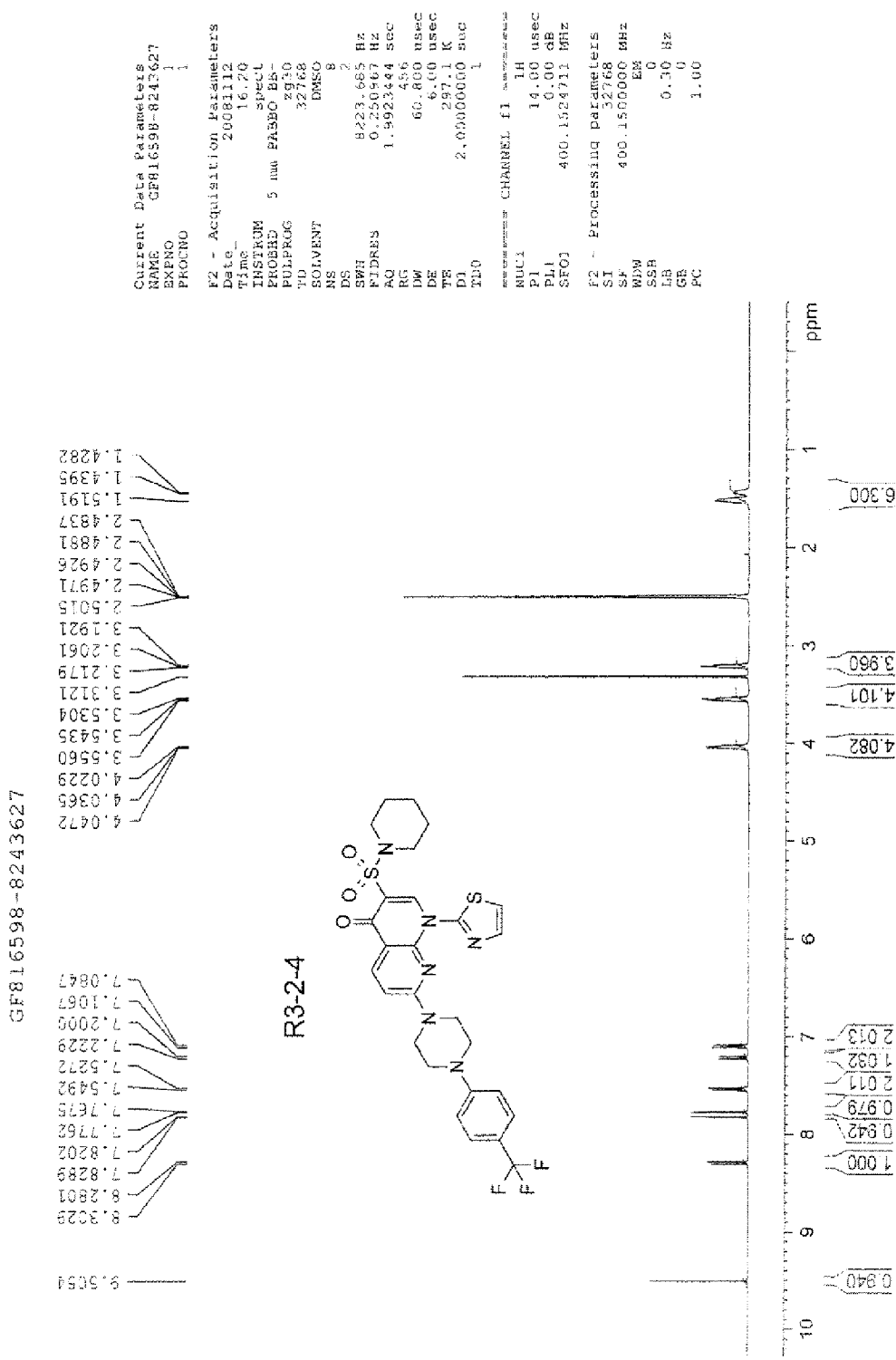

FIG. 4 provides an NMR spectrum for the compound of Example 4.

Figure 5:
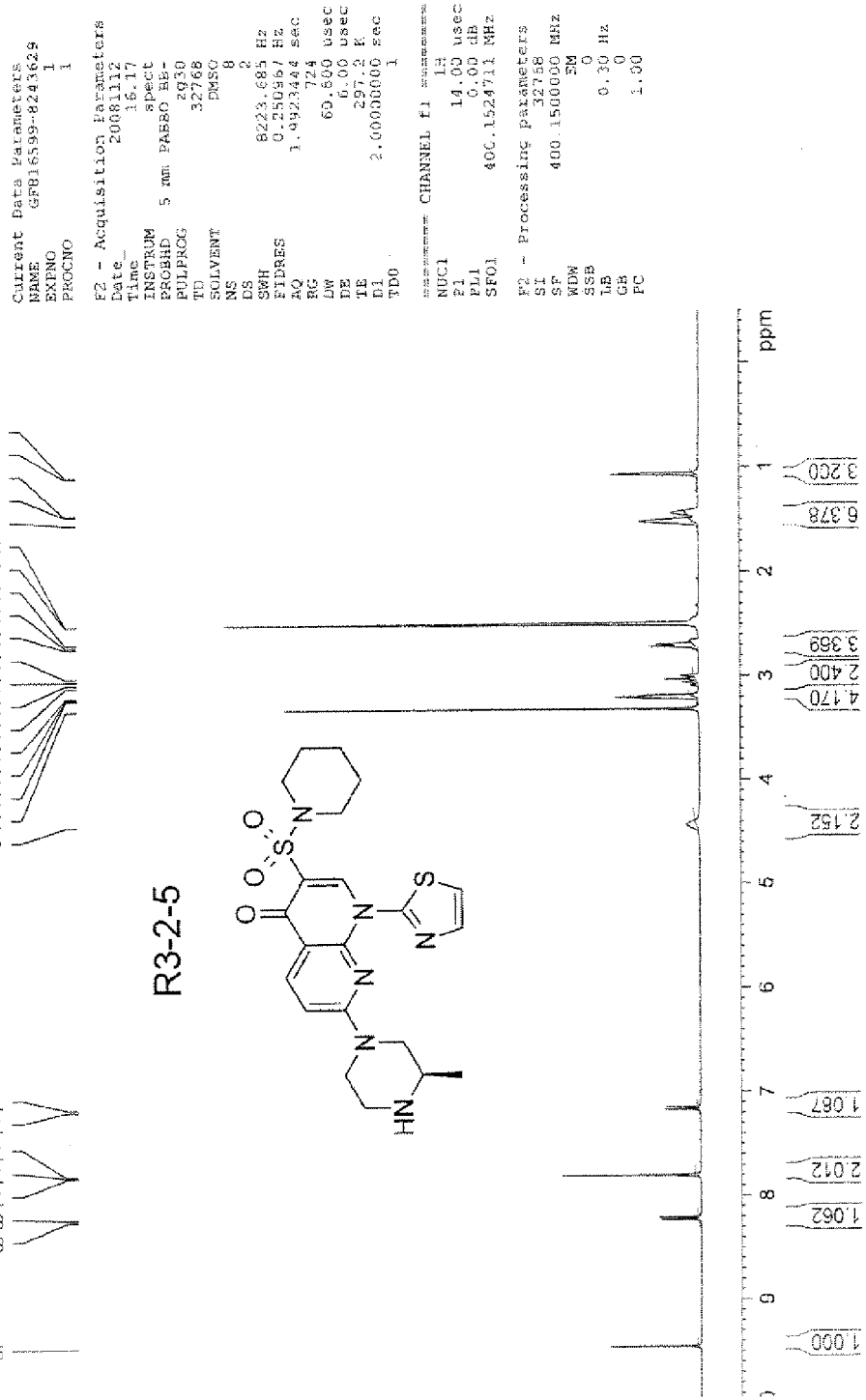

FIG. 5 provides an NMR spectrum for the compound of Example 5.

Figure 6:
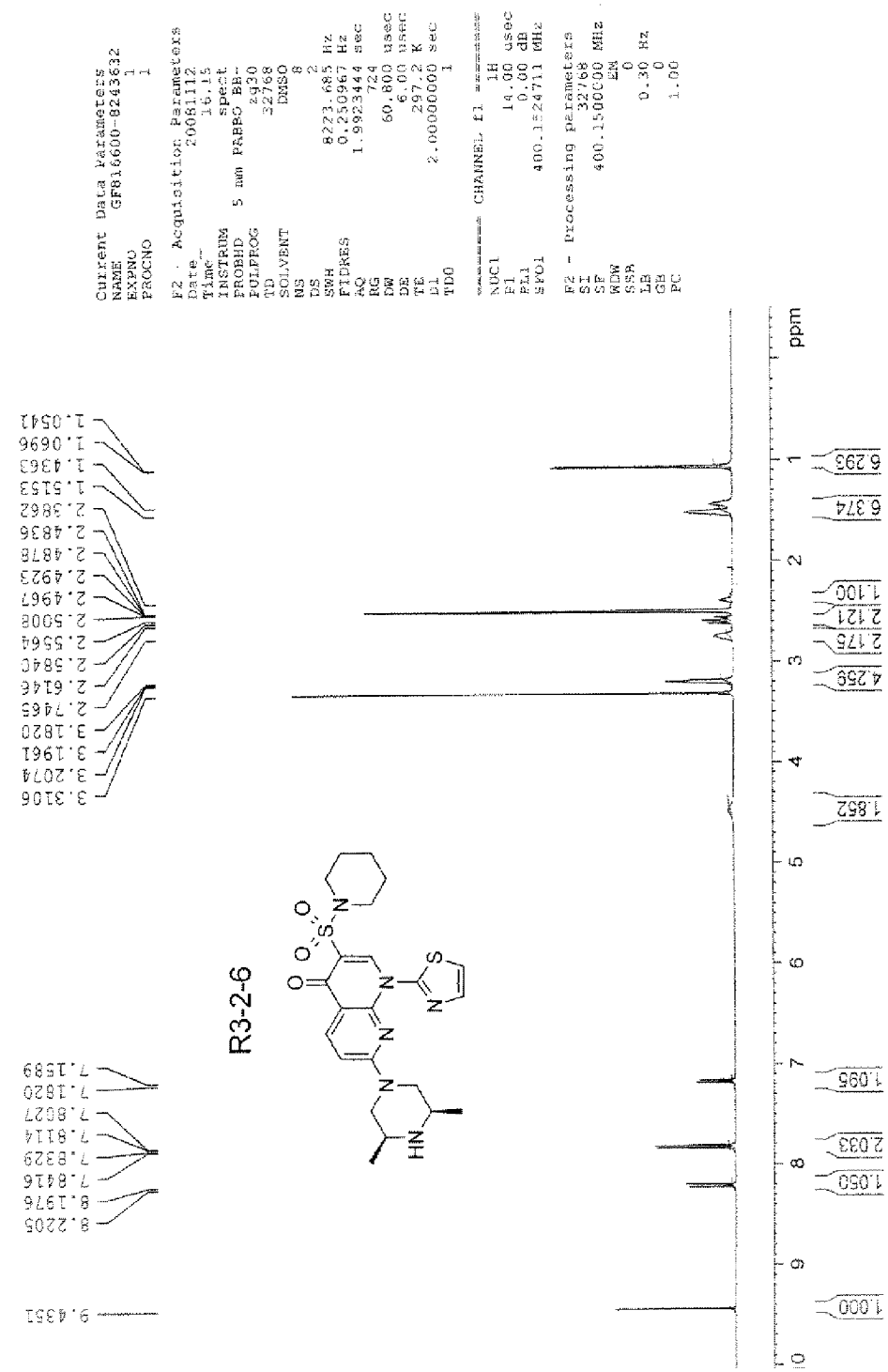

FIG. 6 provides an NMR spectrum for the compound of Example 6.

Figure 7:
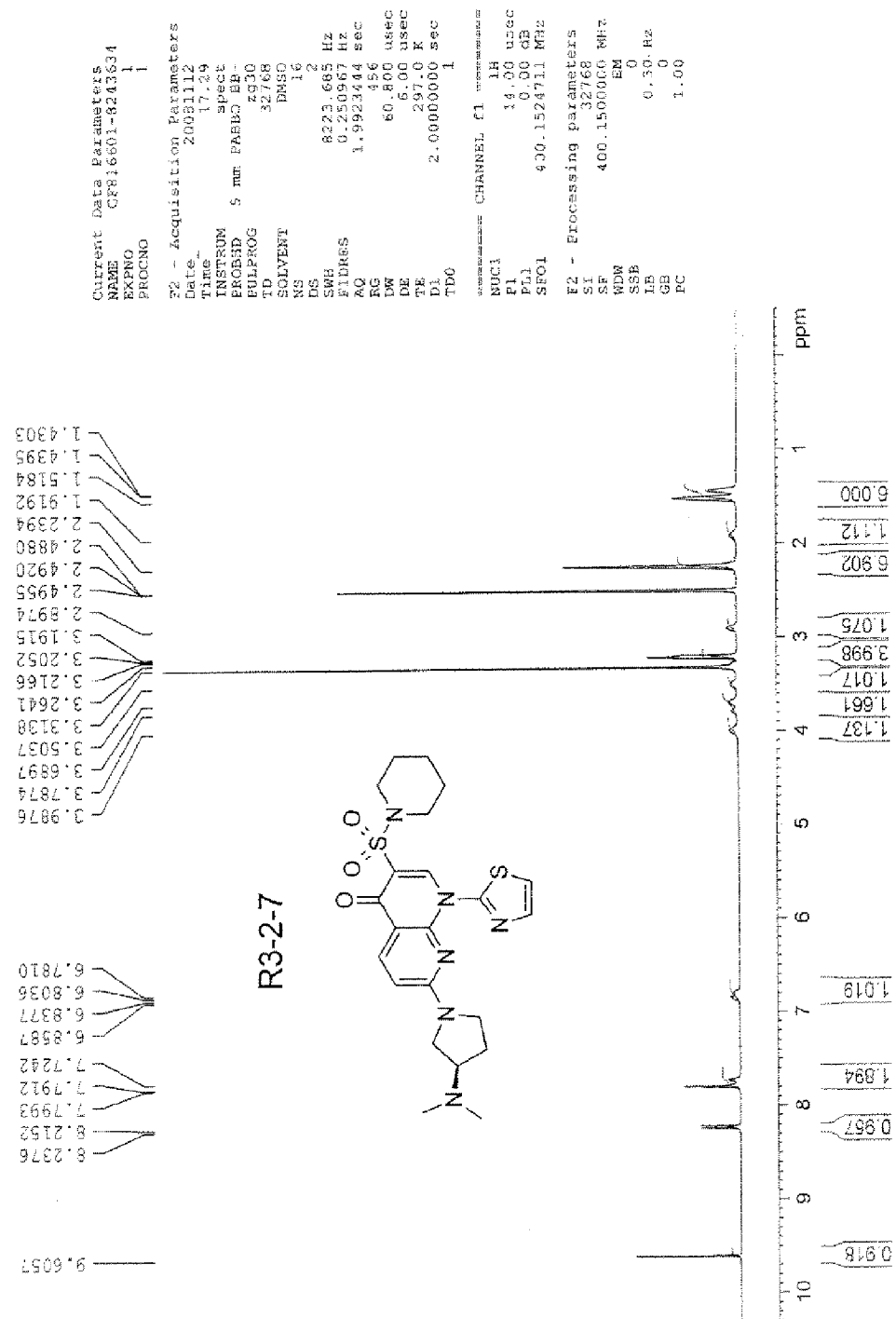

FIG. 7 provides an NMR spectrum for the compound of Example 7.

Figure 8:
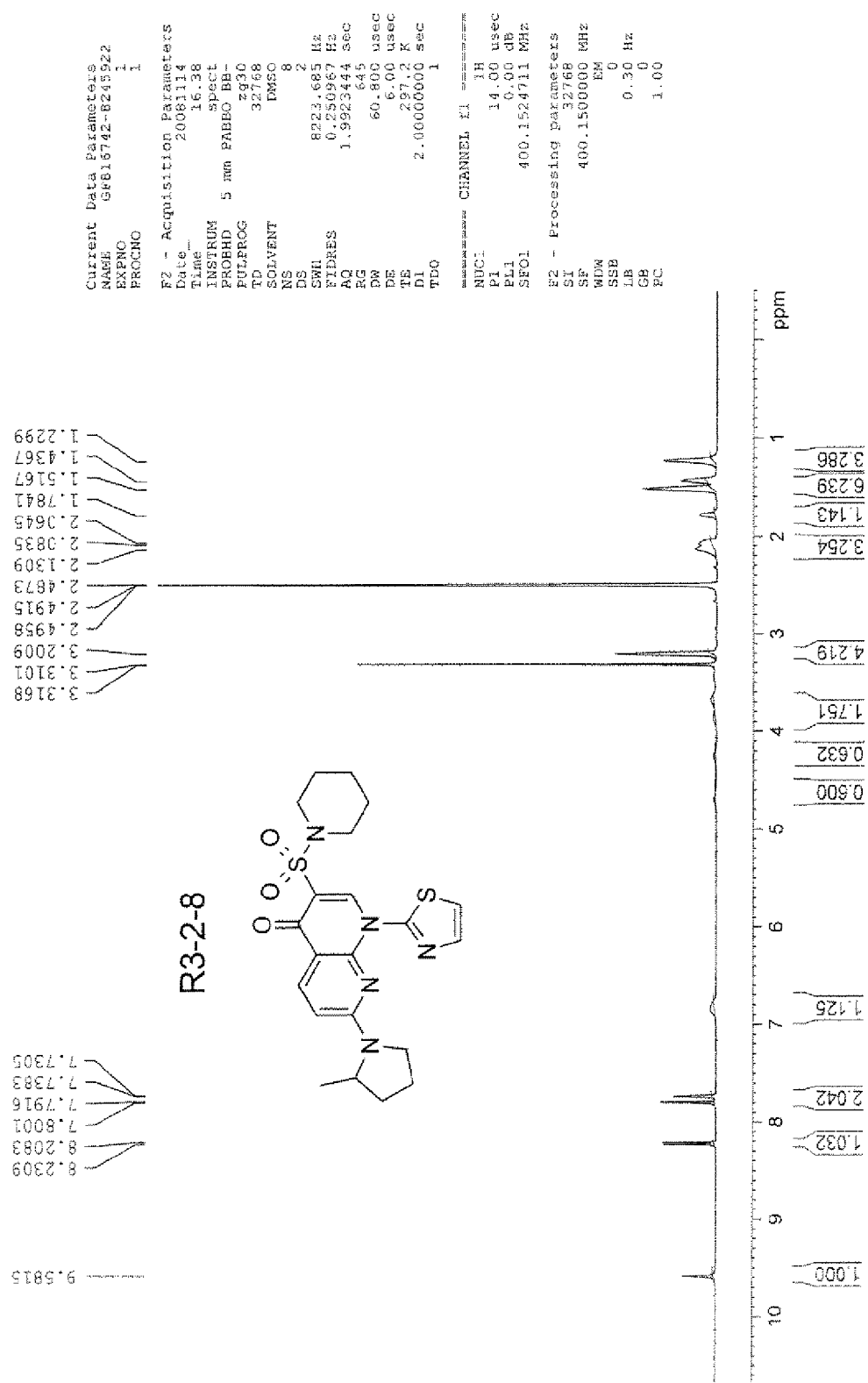

FIG. 8 provides an NMR spectrum for the compound of Example 8.

Figure 9:
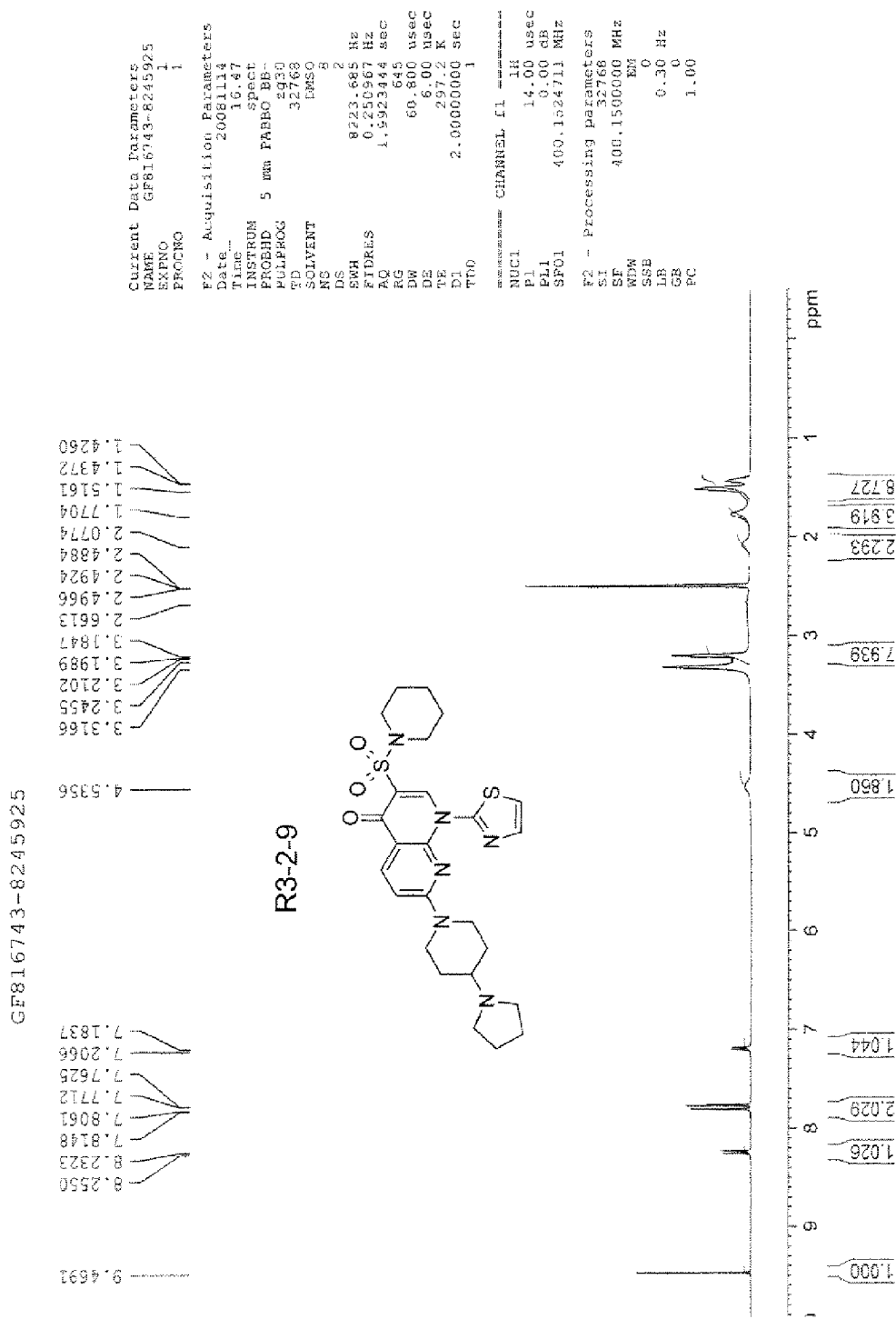

FIG. 9 provides an NMR spectrum for the compound of Example 9.

Figure 10:
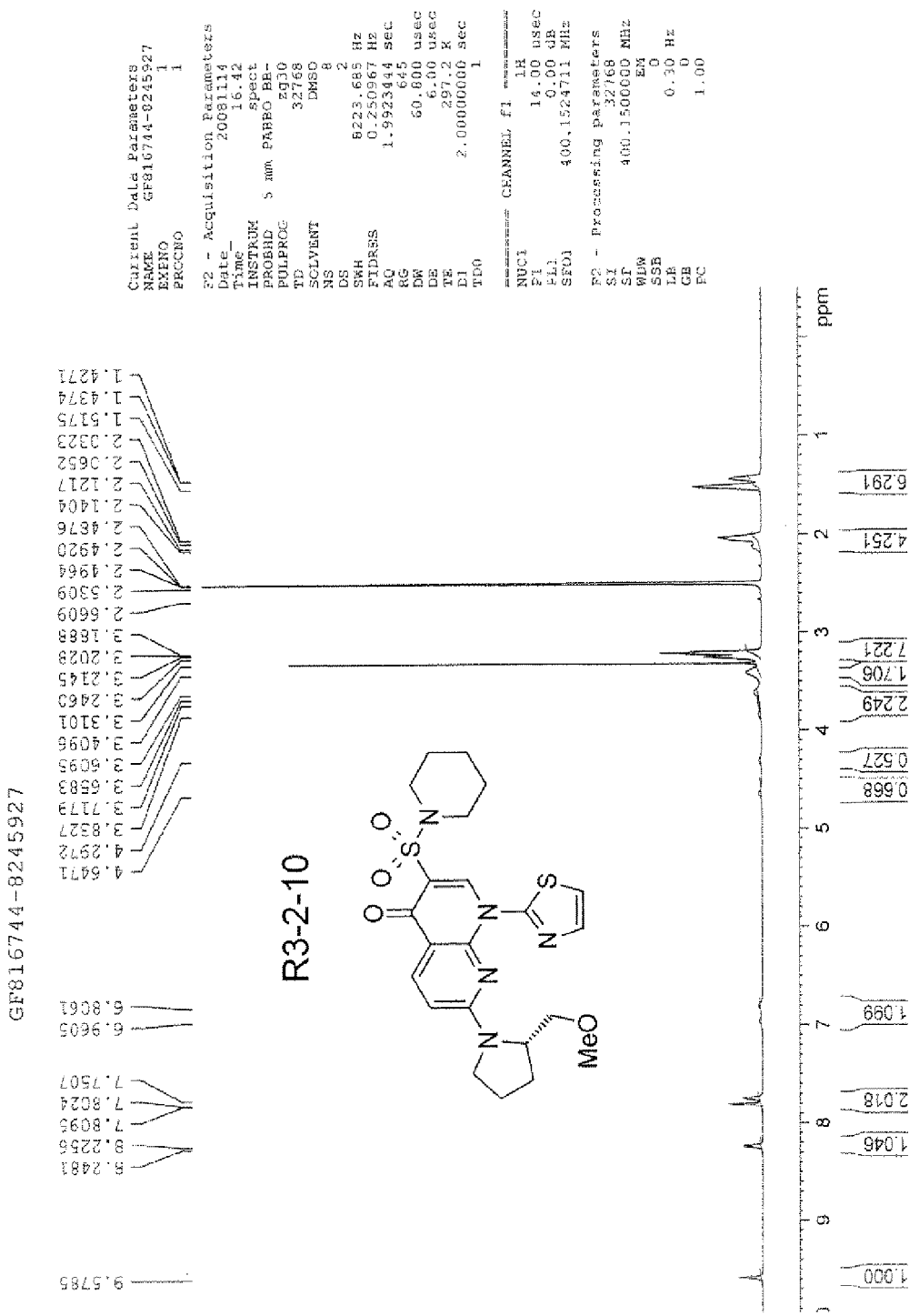

FIG. 10 provides an NMR spectrum for the compound of Example 10.

Figure 11:
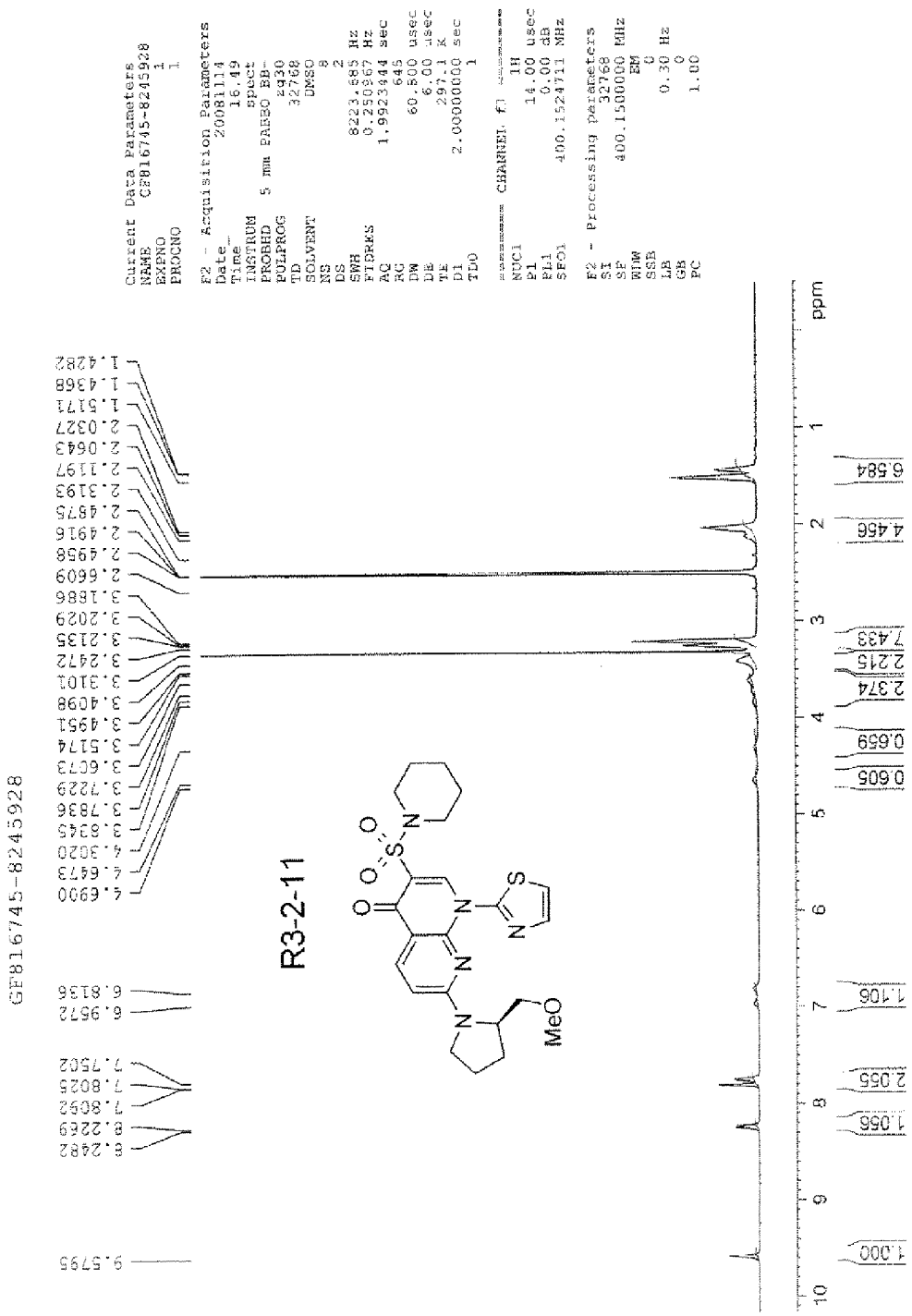

FIG. 11 provides an NMR spectrum for the compound of Example 11.

Figure 12:
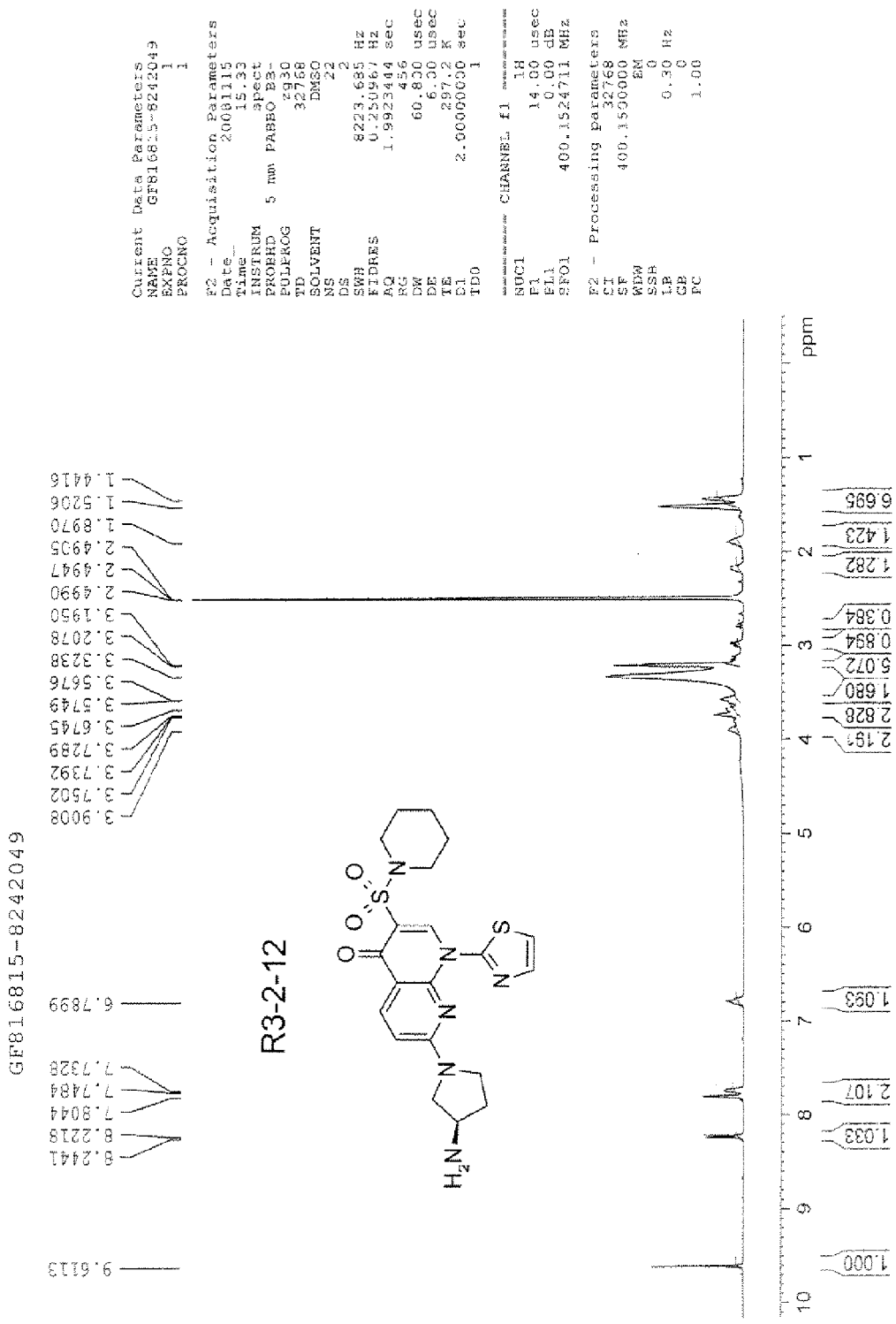

FIG. 12 provides an NMR spectrum for the compound of Example 12.

Figure 13:
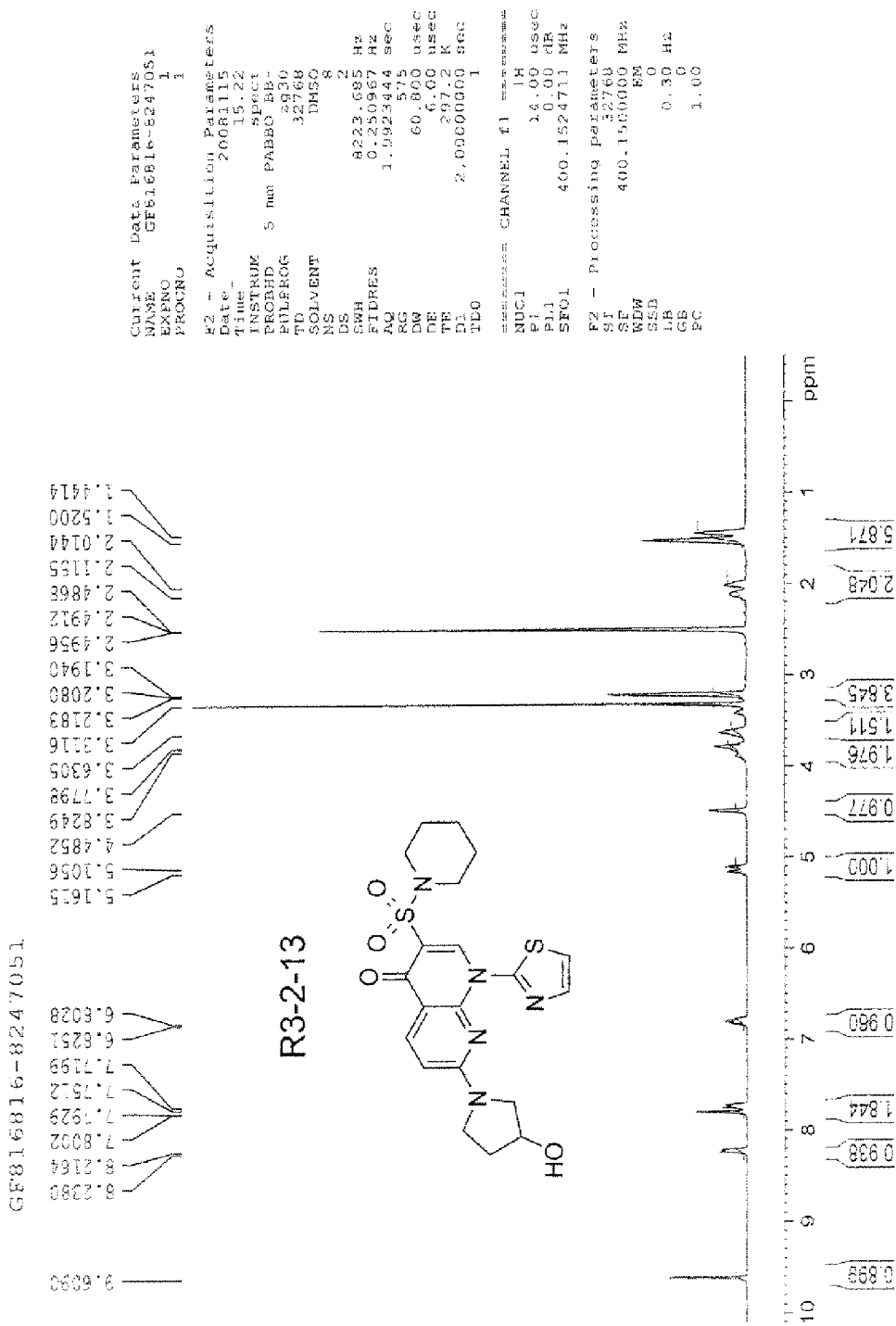

FIG. 13 provides an NMR spectrum for the compound of Example 13.

Figure 14:
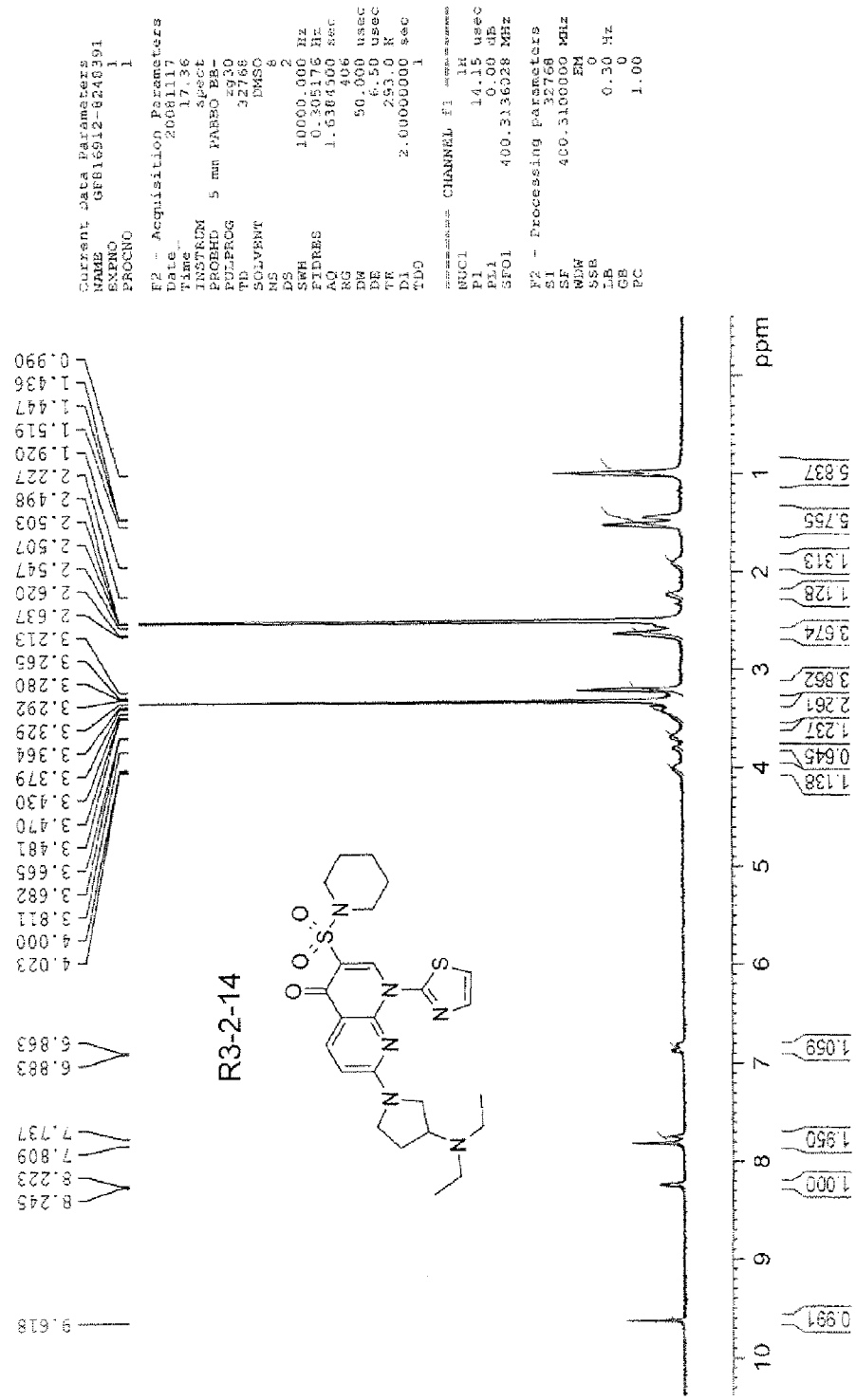

FIG. 14 provides an NMR spectrum for the compound of Example 14.

Figure 15:
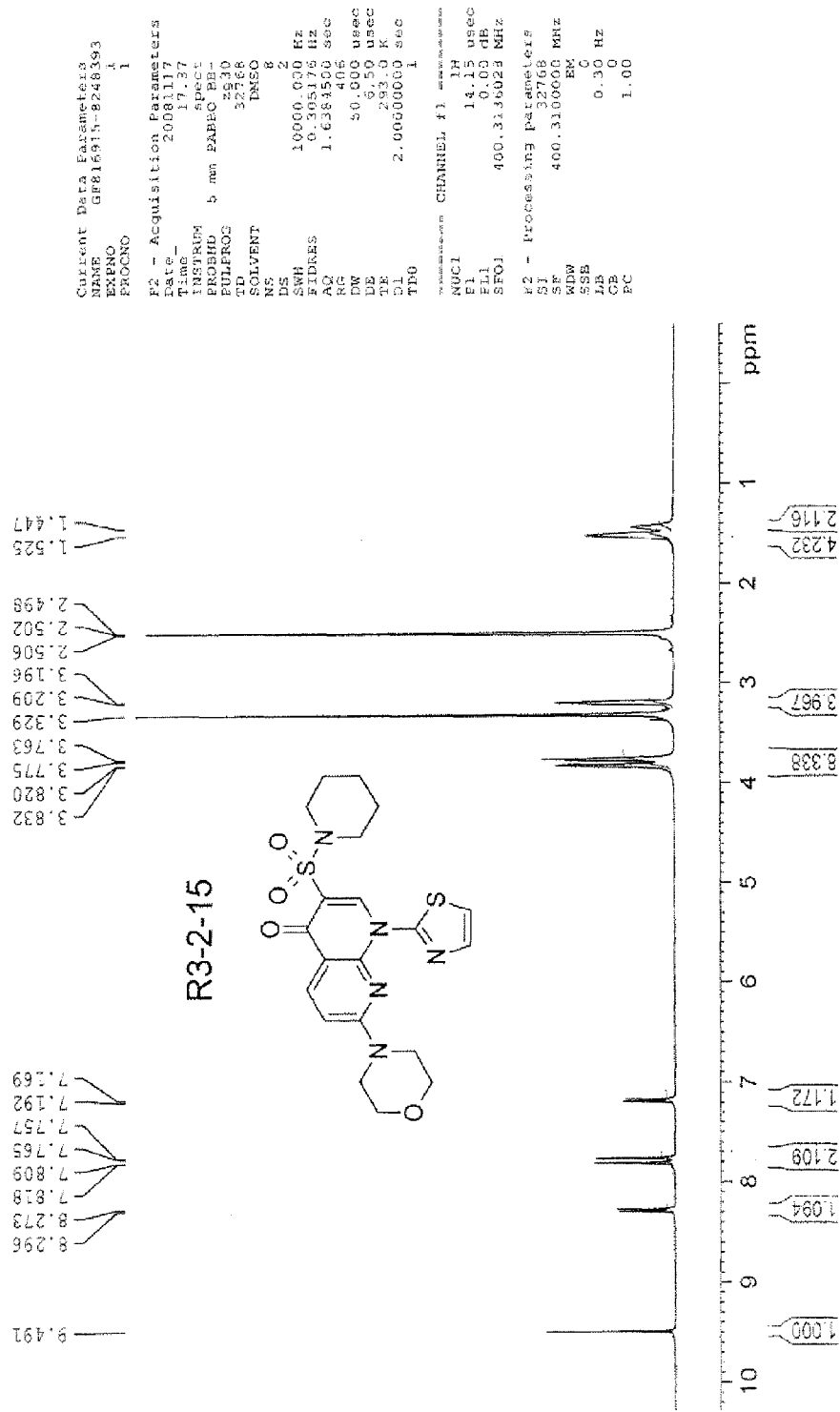

FIG. 15 provides an NMR spectrum for the compound of Example 15.

Figure 16:
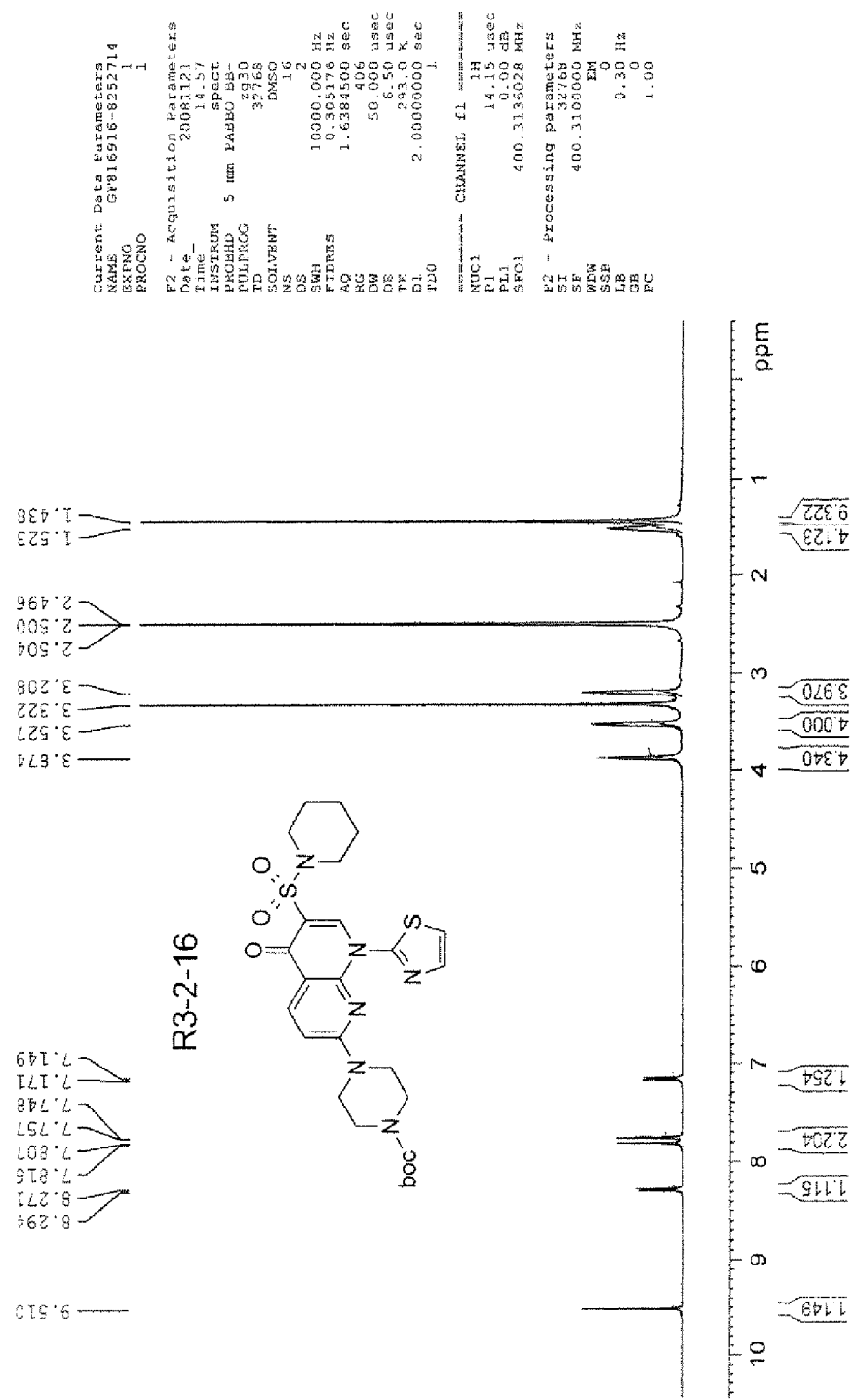

FIG. 16 provides an NMR spectrum for the compound of Example 16.

Figure 17:
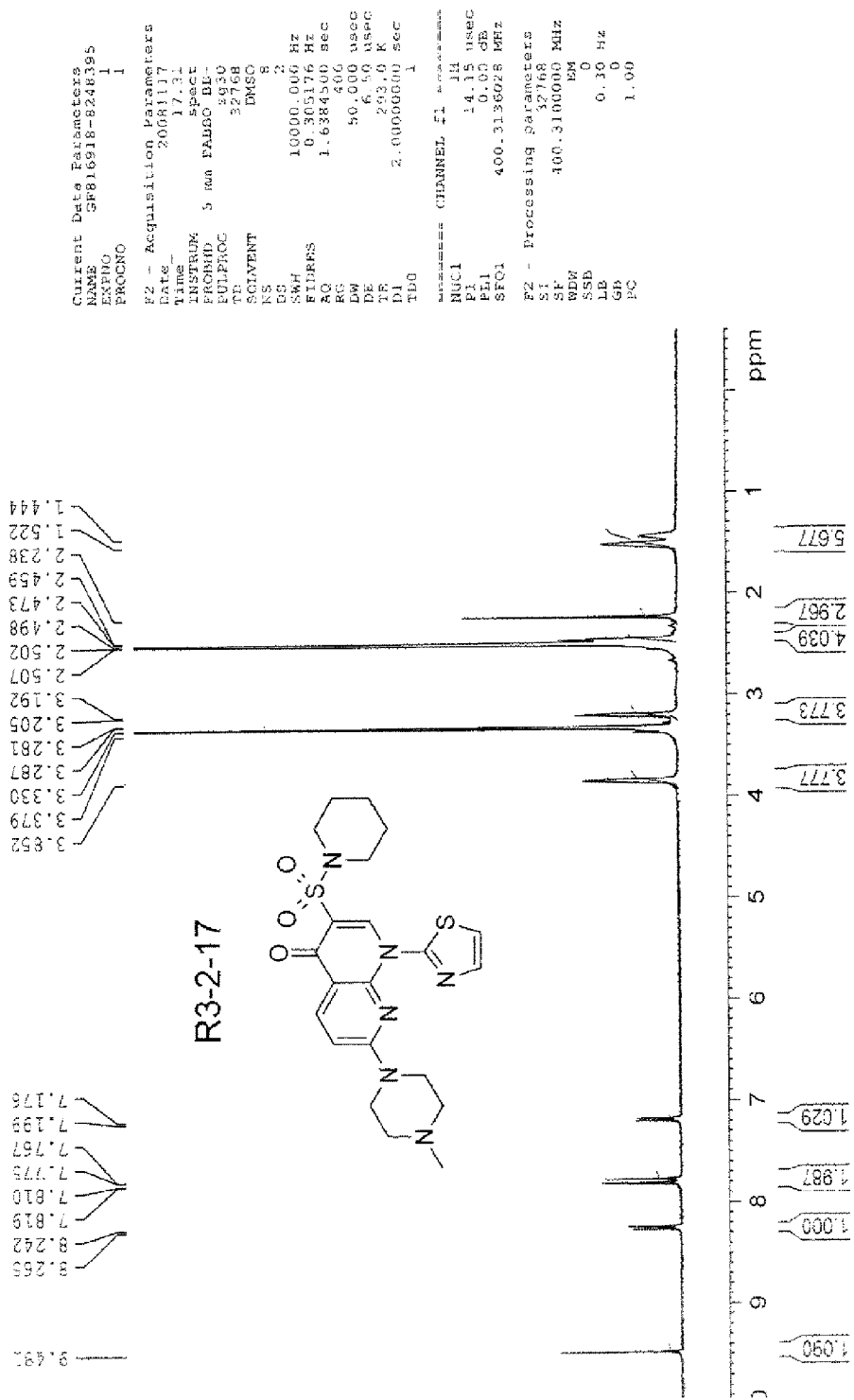

FIG. 17 provides an NMR spectrum for the compound of Example 17.

Figure 18:
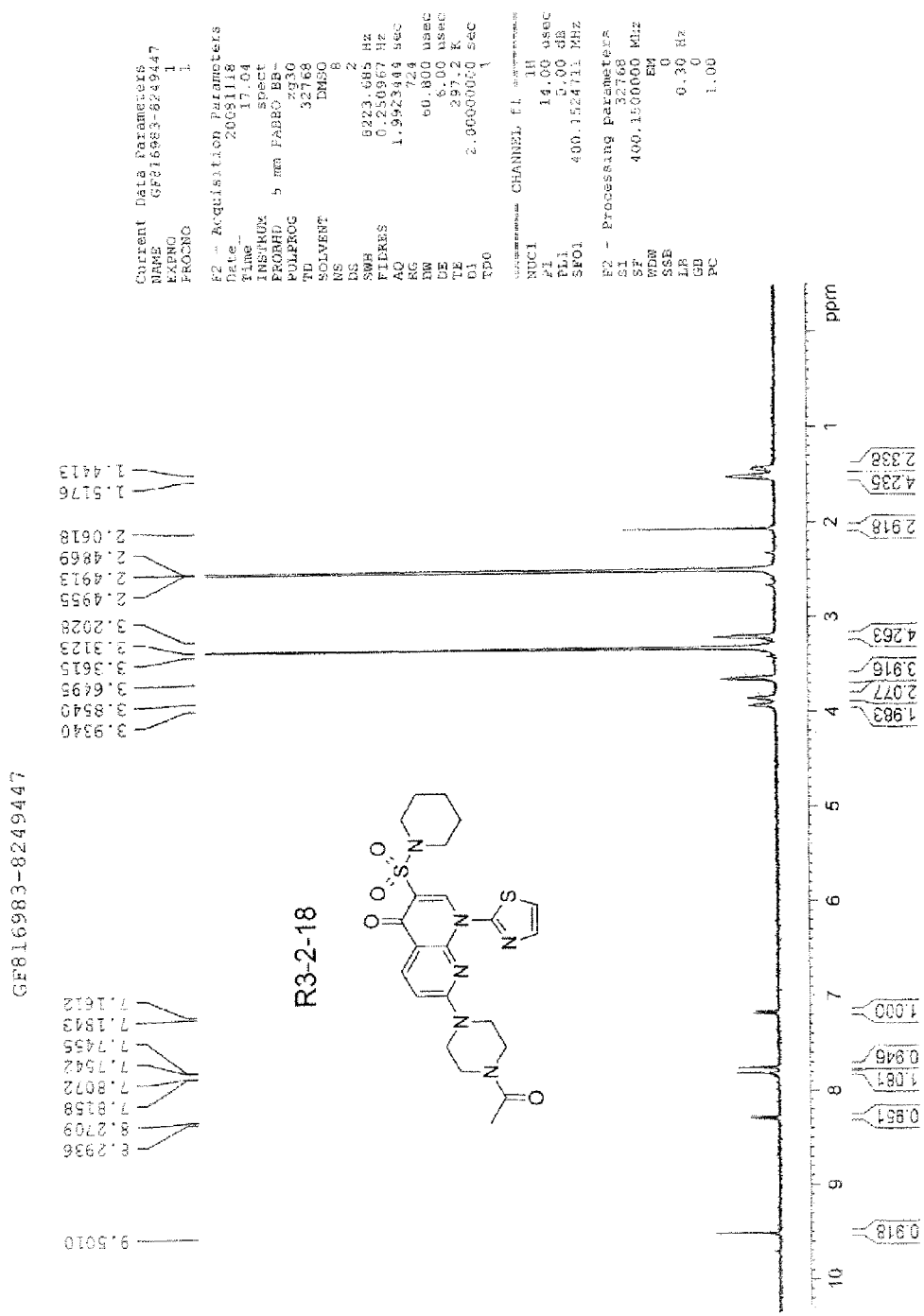

FIG. 18 provides an NMR spectrum for the compound of Example 18.

Figure 19:
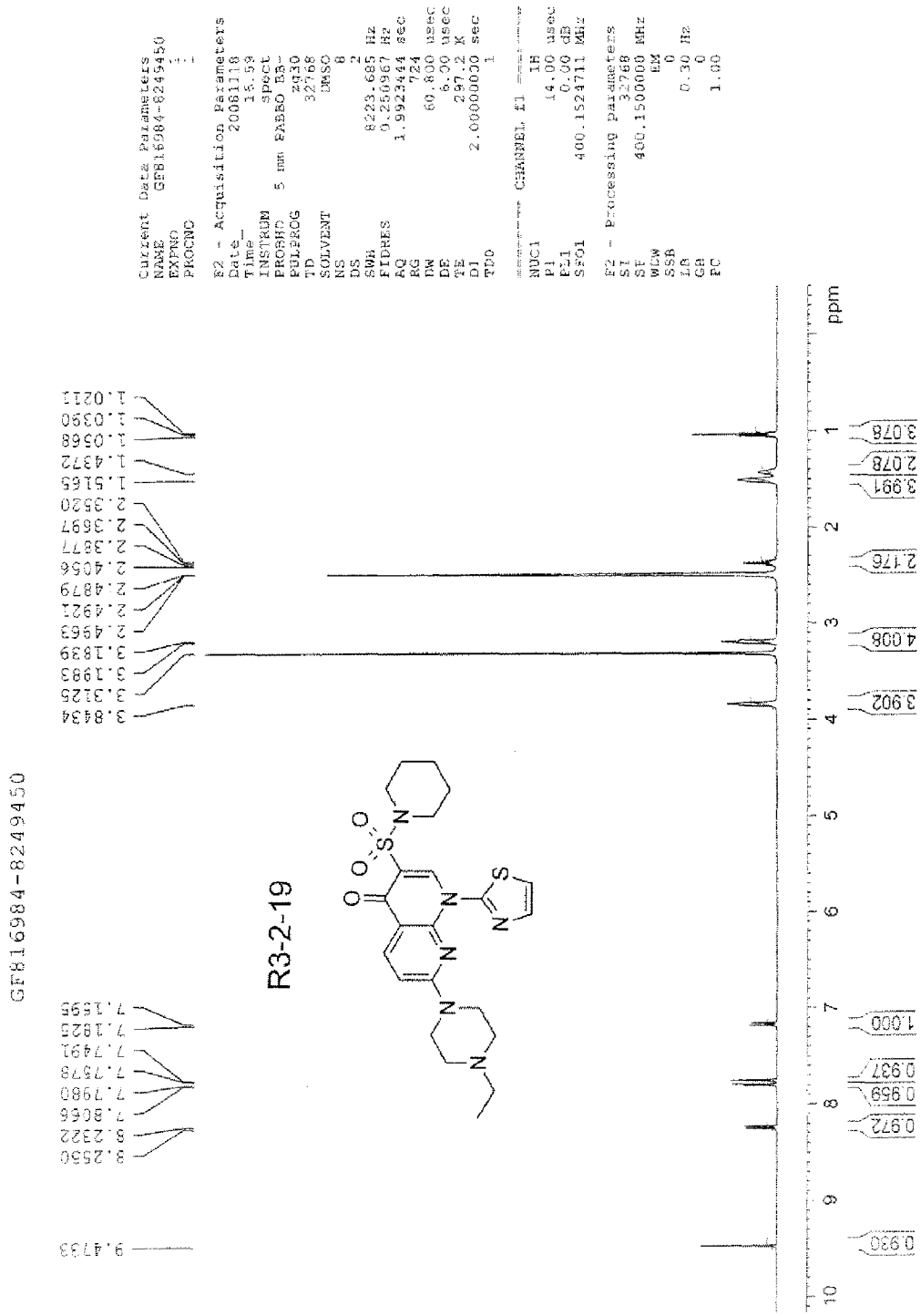

FIG. 19 provides an NMR spectrum for the compound of Example 19.

Figure 20:
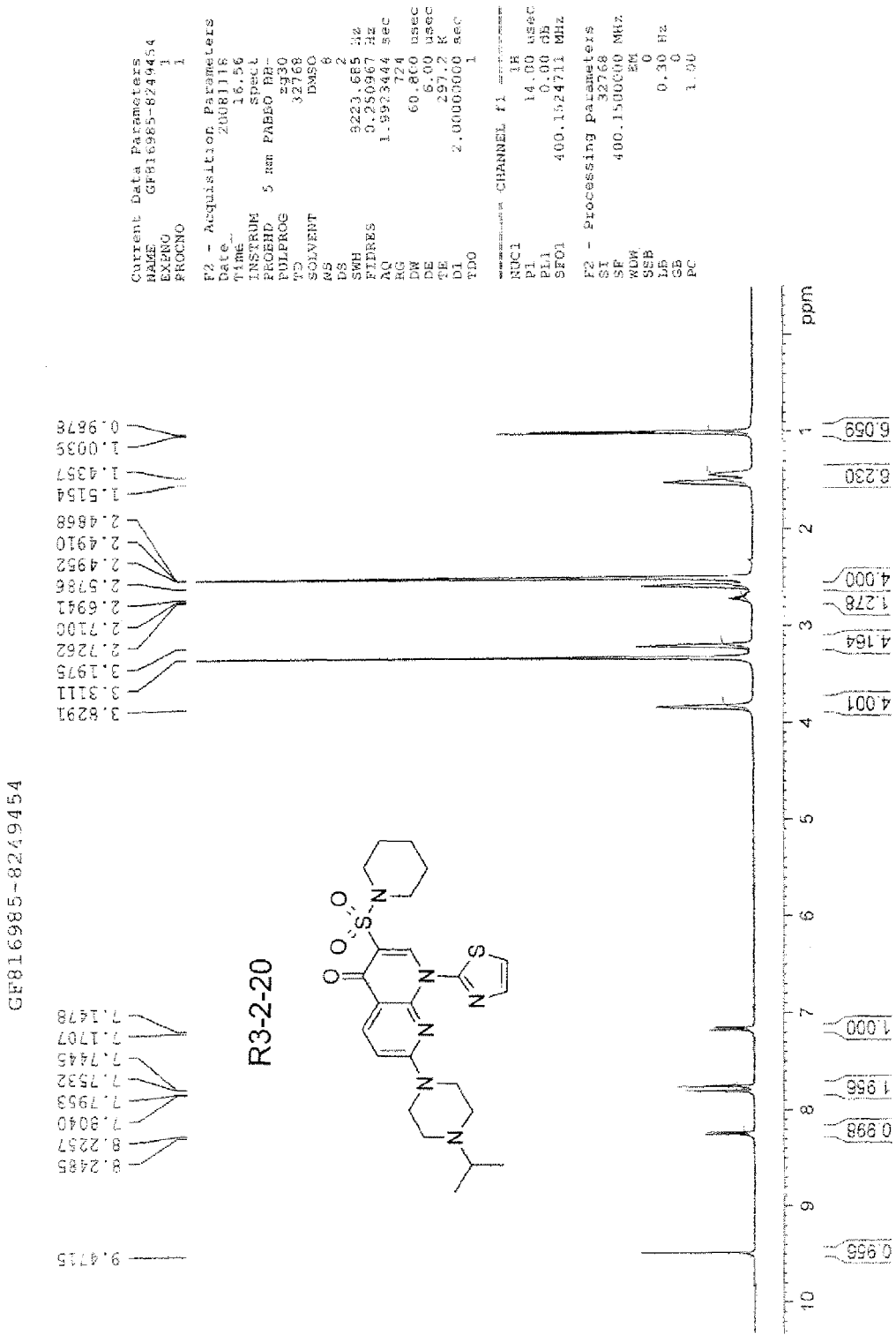

FIG. 20 provides an NMR spectrum for the compound of Example 20.

Figure 21:
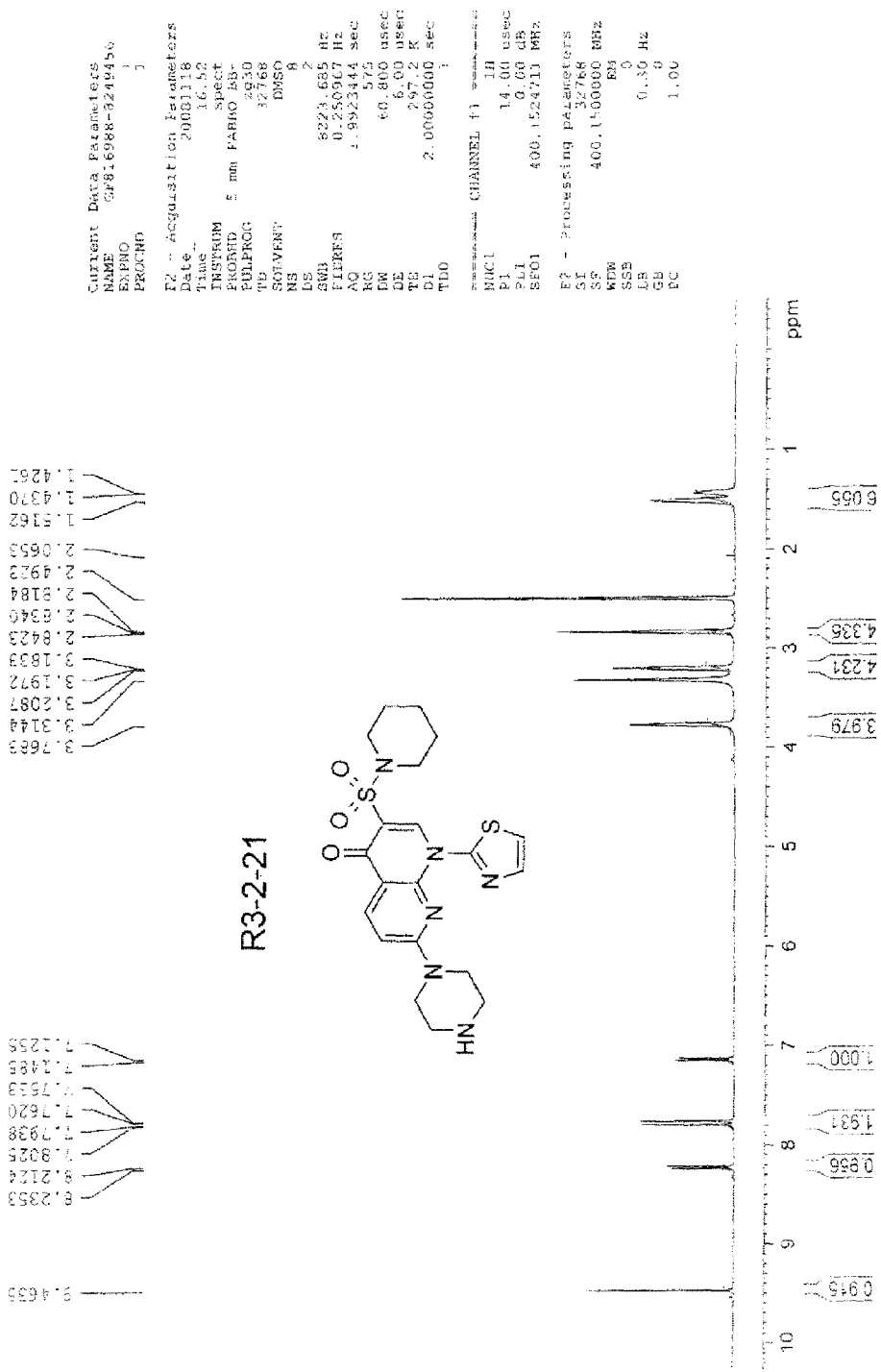

FIG. 21 provides an NMR spectrum for the compound of Example 21.

Figure 22:
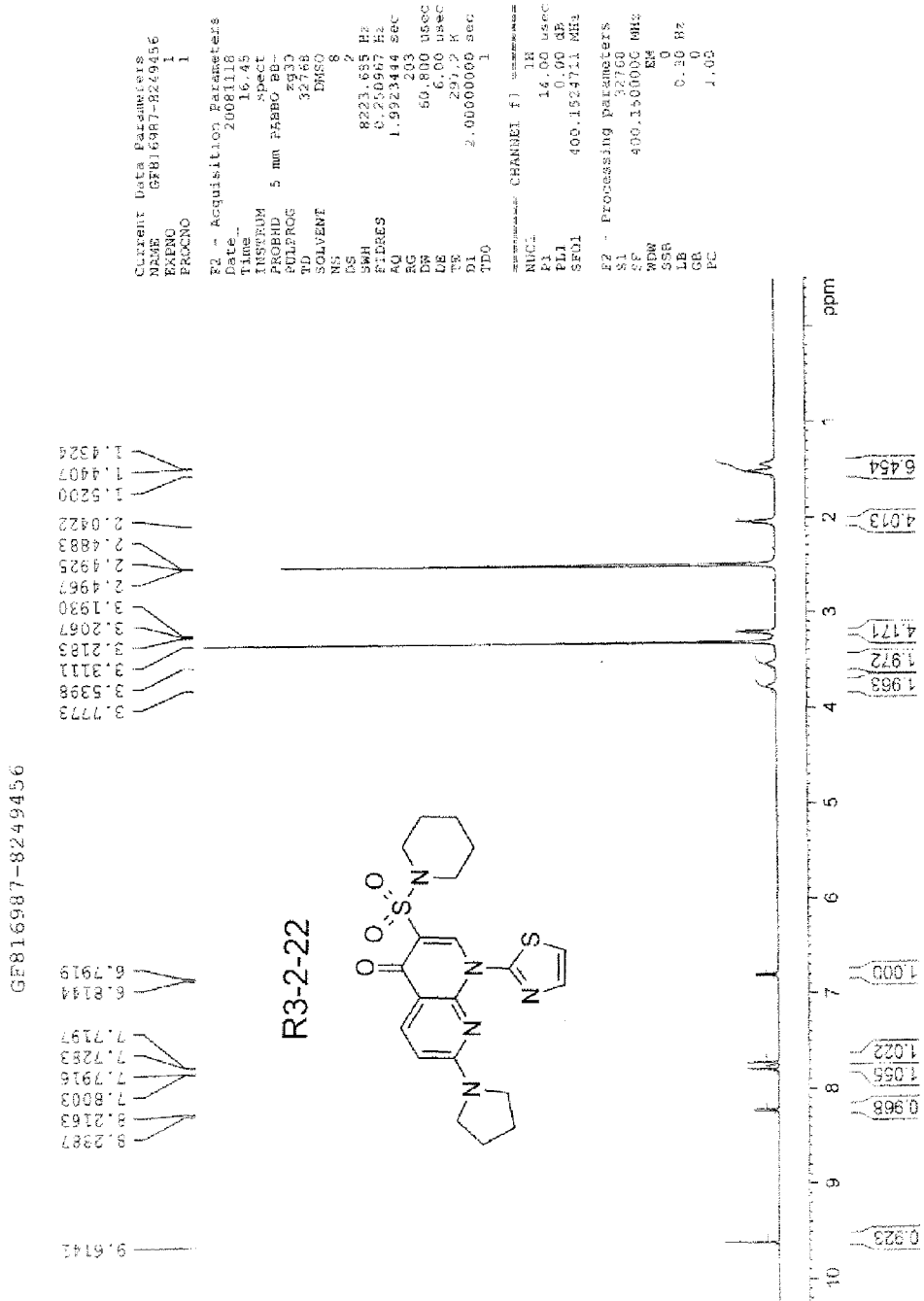

FIG. 22 provides an NMR spectrum for the compound of Example 22.

Figure 23:
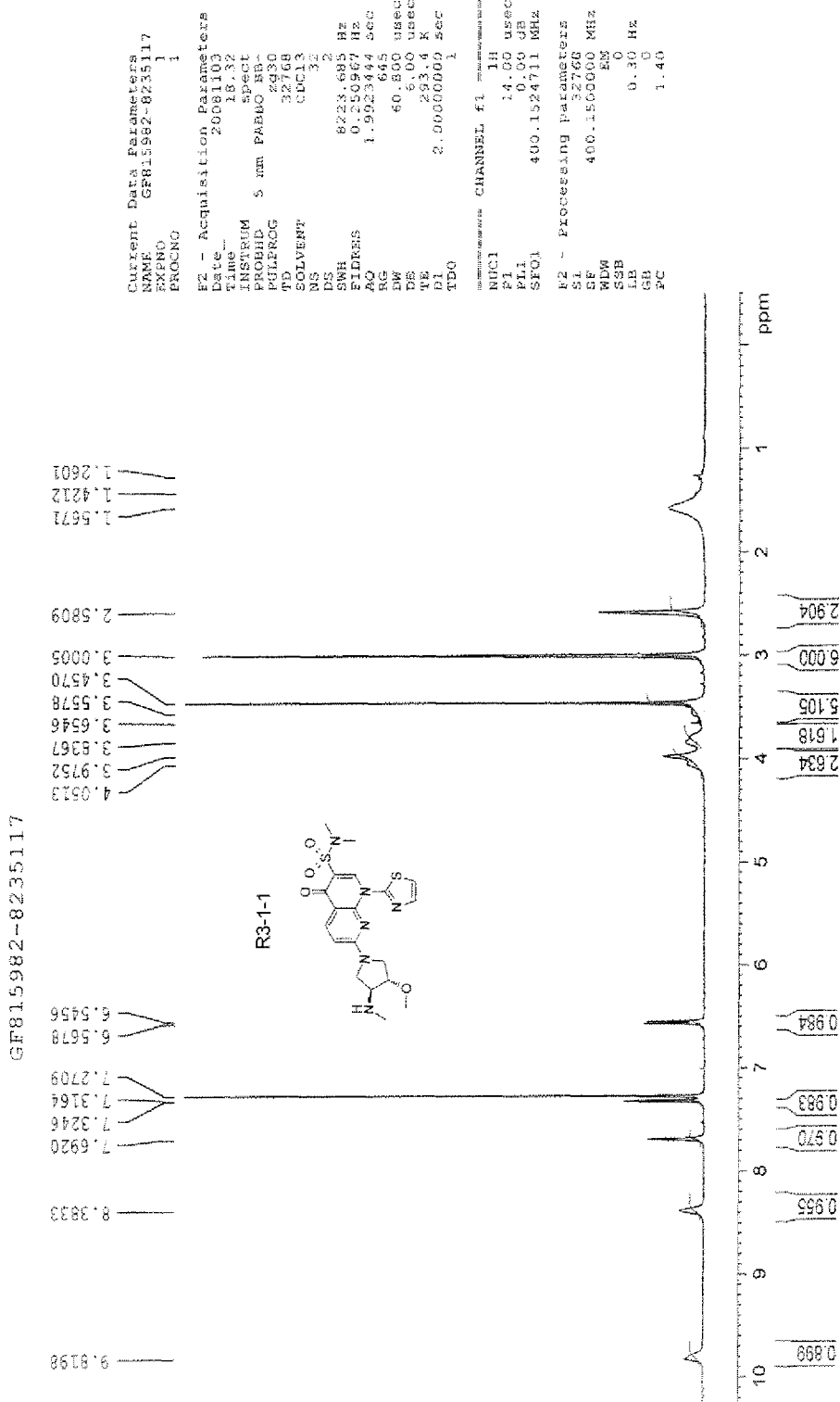

FIG. 23 provides an NMR spectrum for the compound of Example 23.

Figure 24:
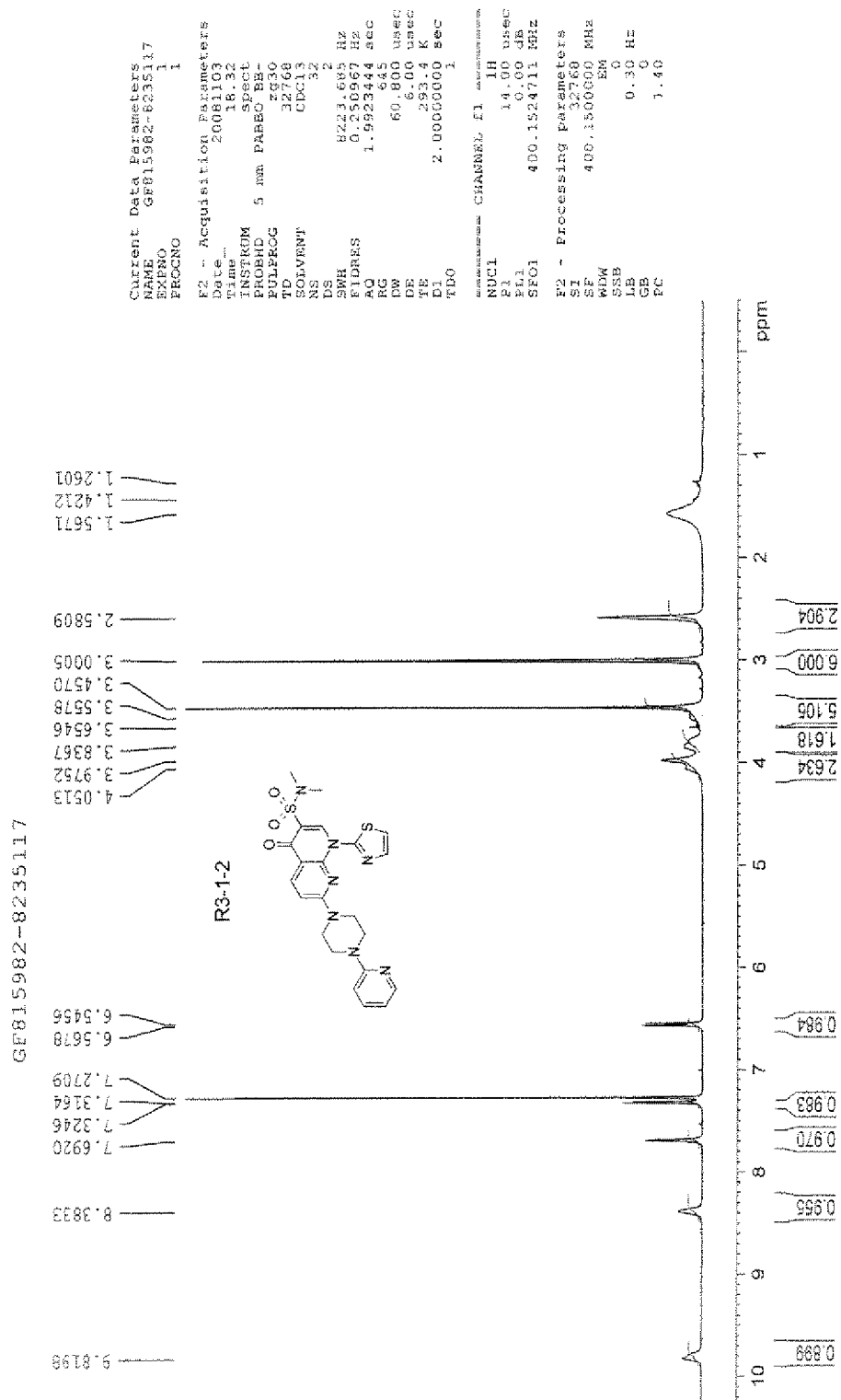

FIG. 24 provides an NMR spectrum for the compound of Example 24.

Figure 25:
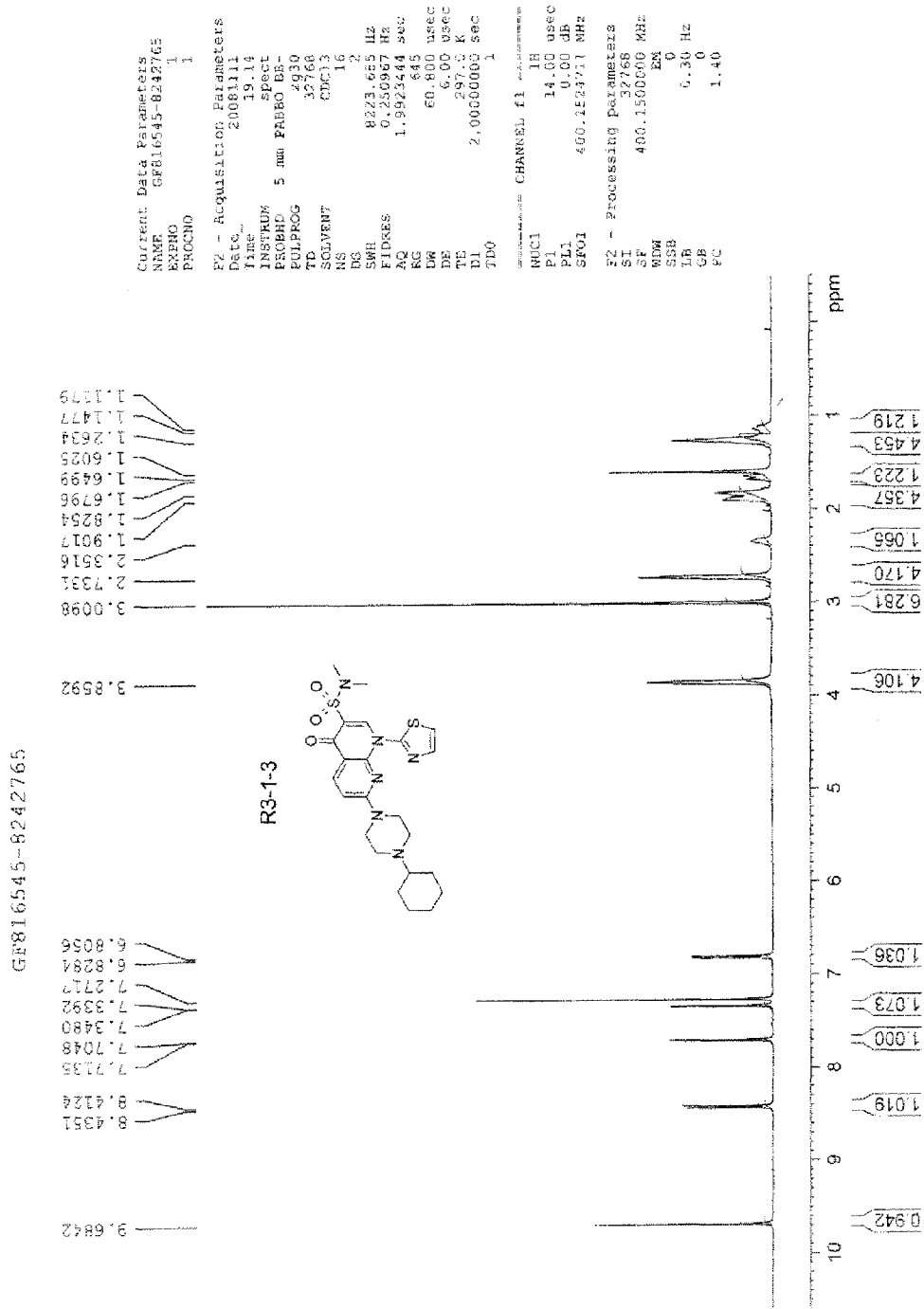

FIG. 25 provides an NMR spectrum for the compound of Example 25.

Figure 26:
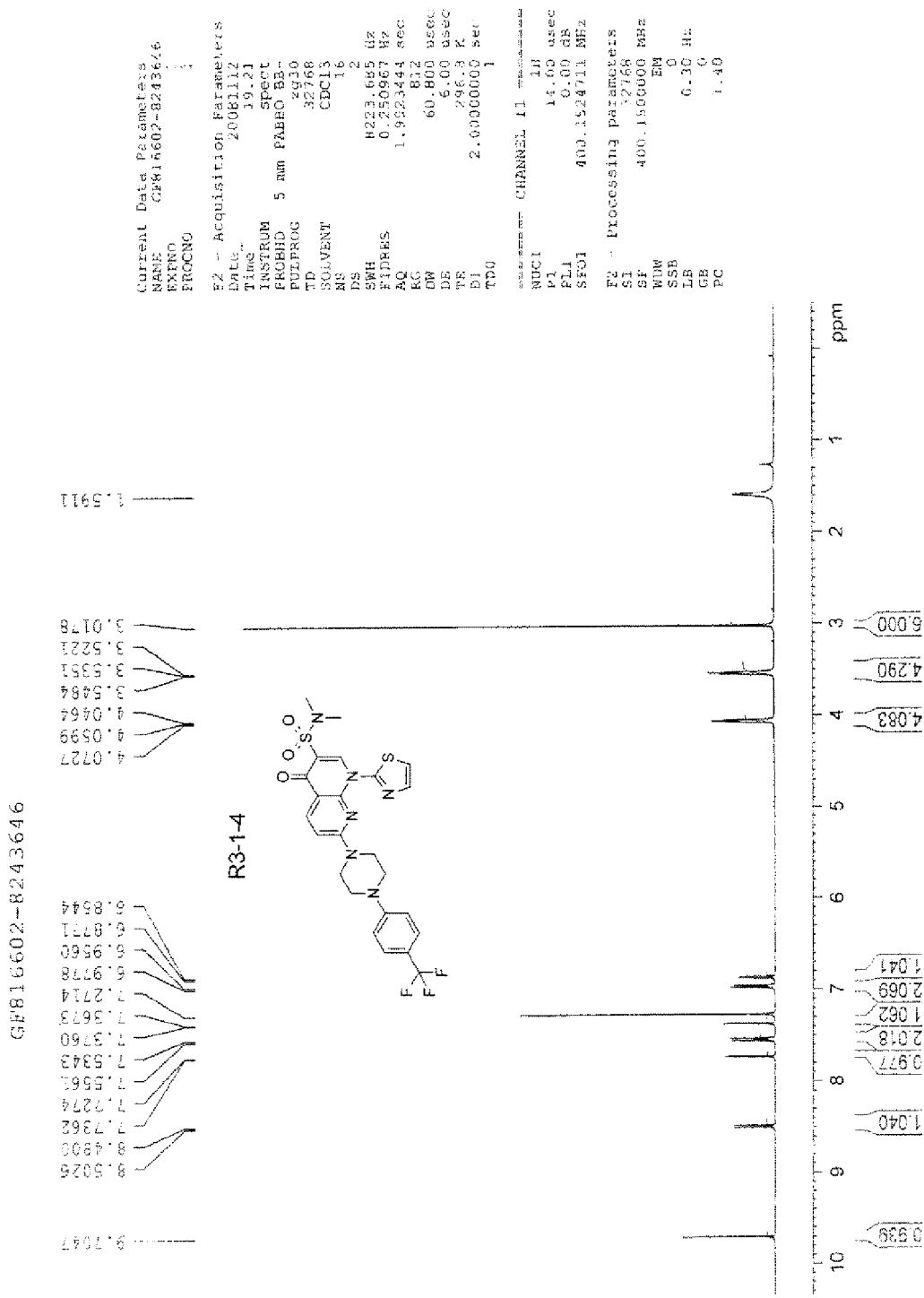

FIG. 26 provides an NMR spectrum for the compound of Example 26.

Figure 27:
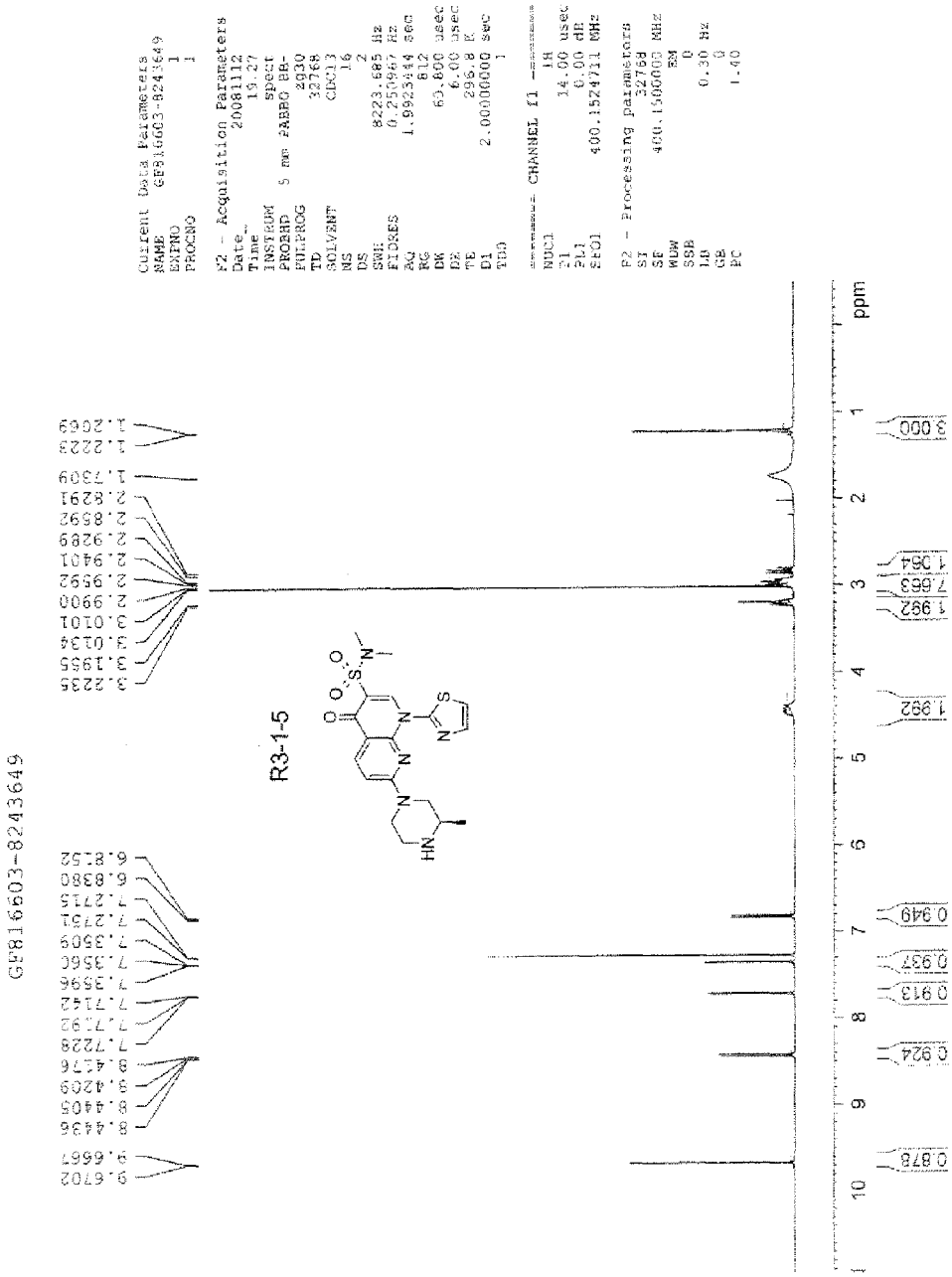

FIG. 27 provides an NMR spectrum for the compound of Example 27.

Figure 28:
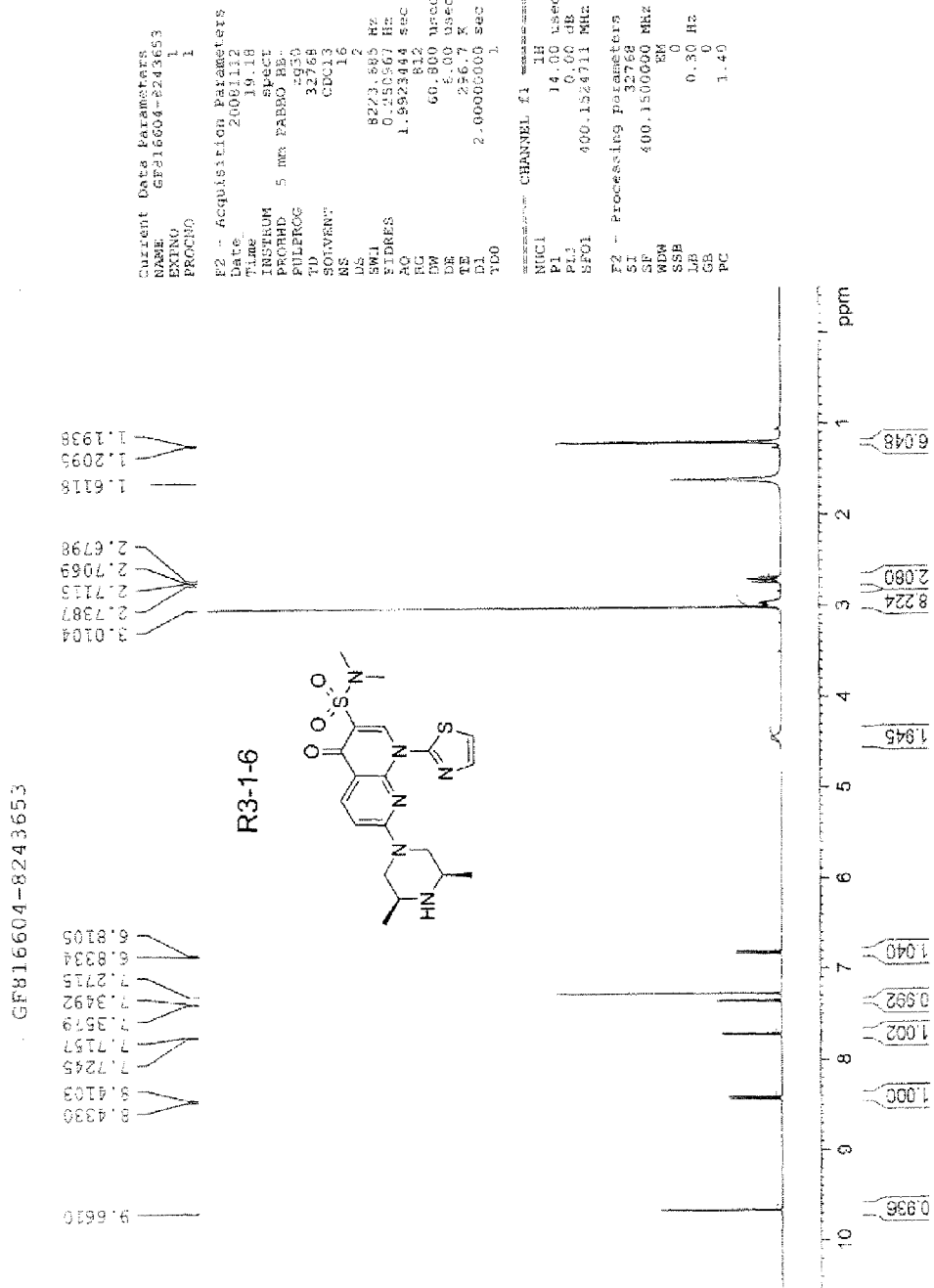
Figure 29:
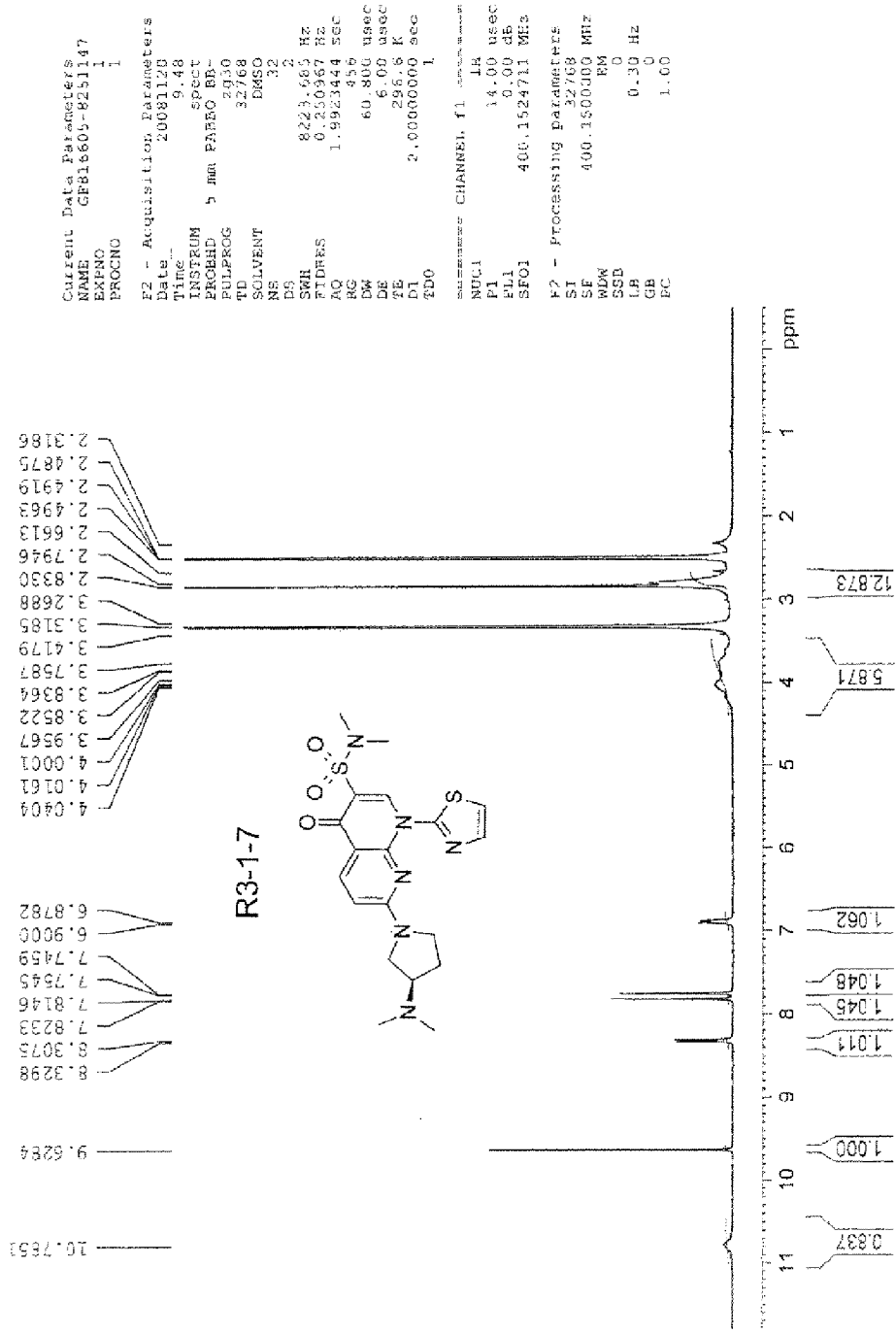
Figure 30:
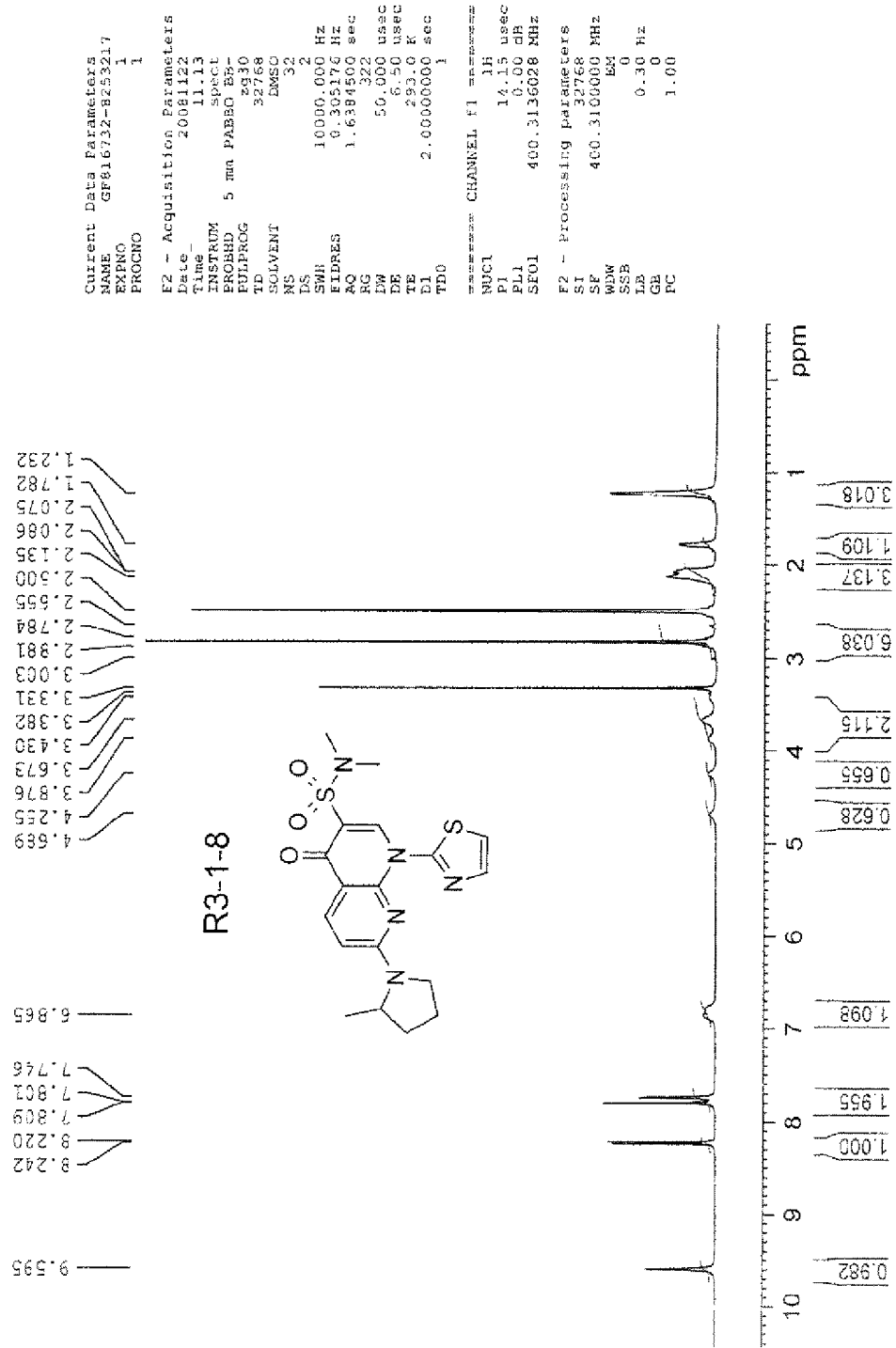
Figure 31:
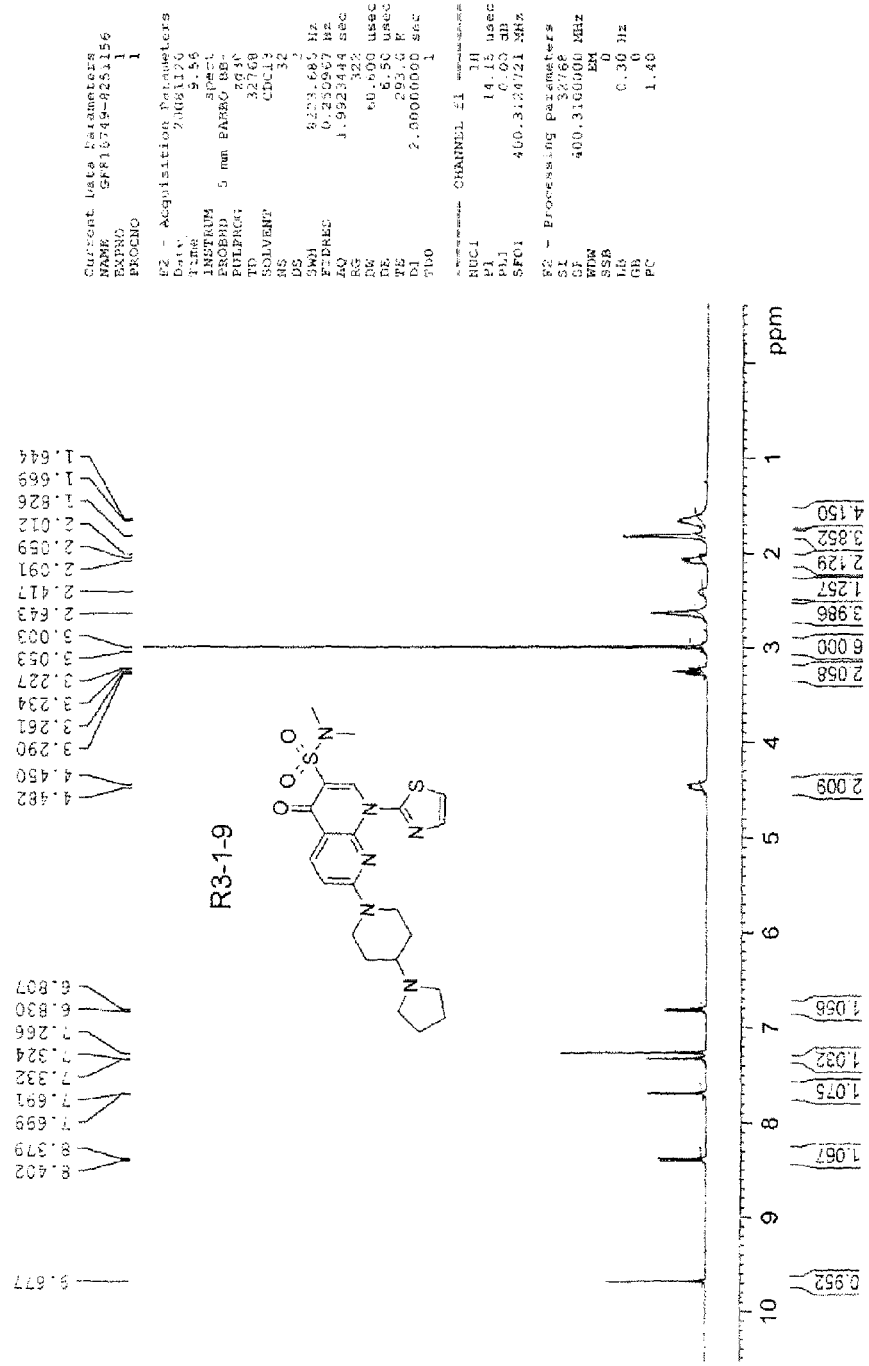
Figure 32:
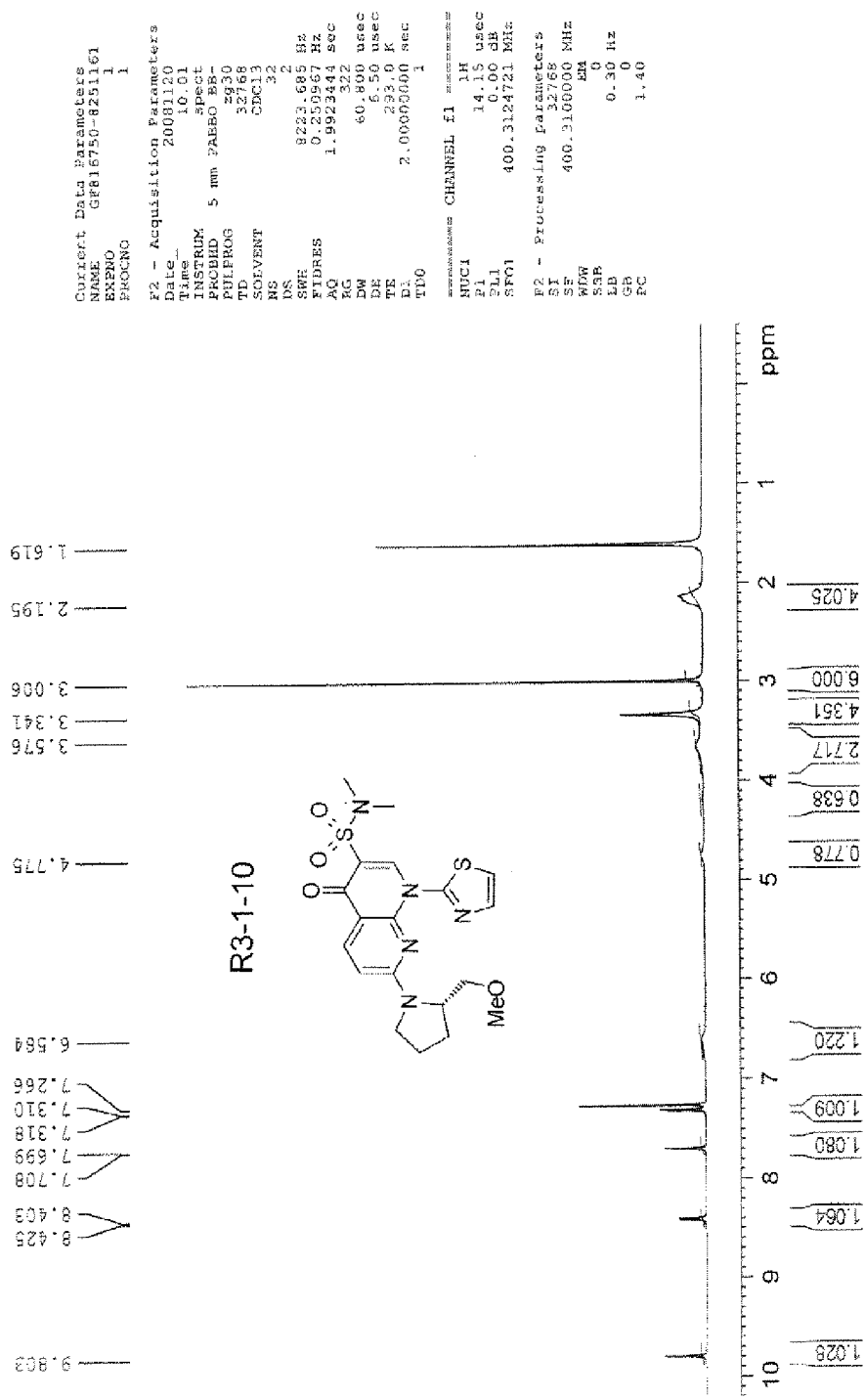
Figure 33:
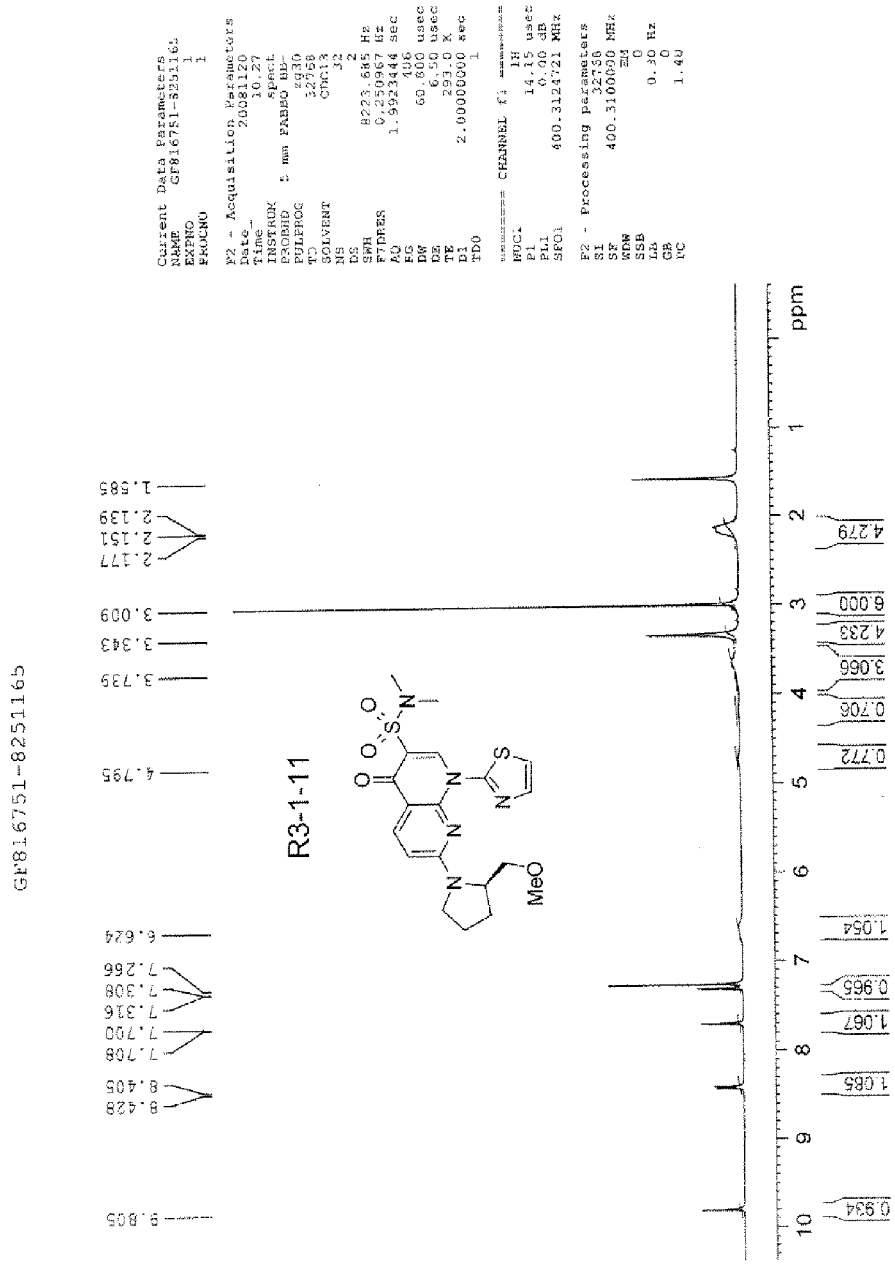
Figure 34:
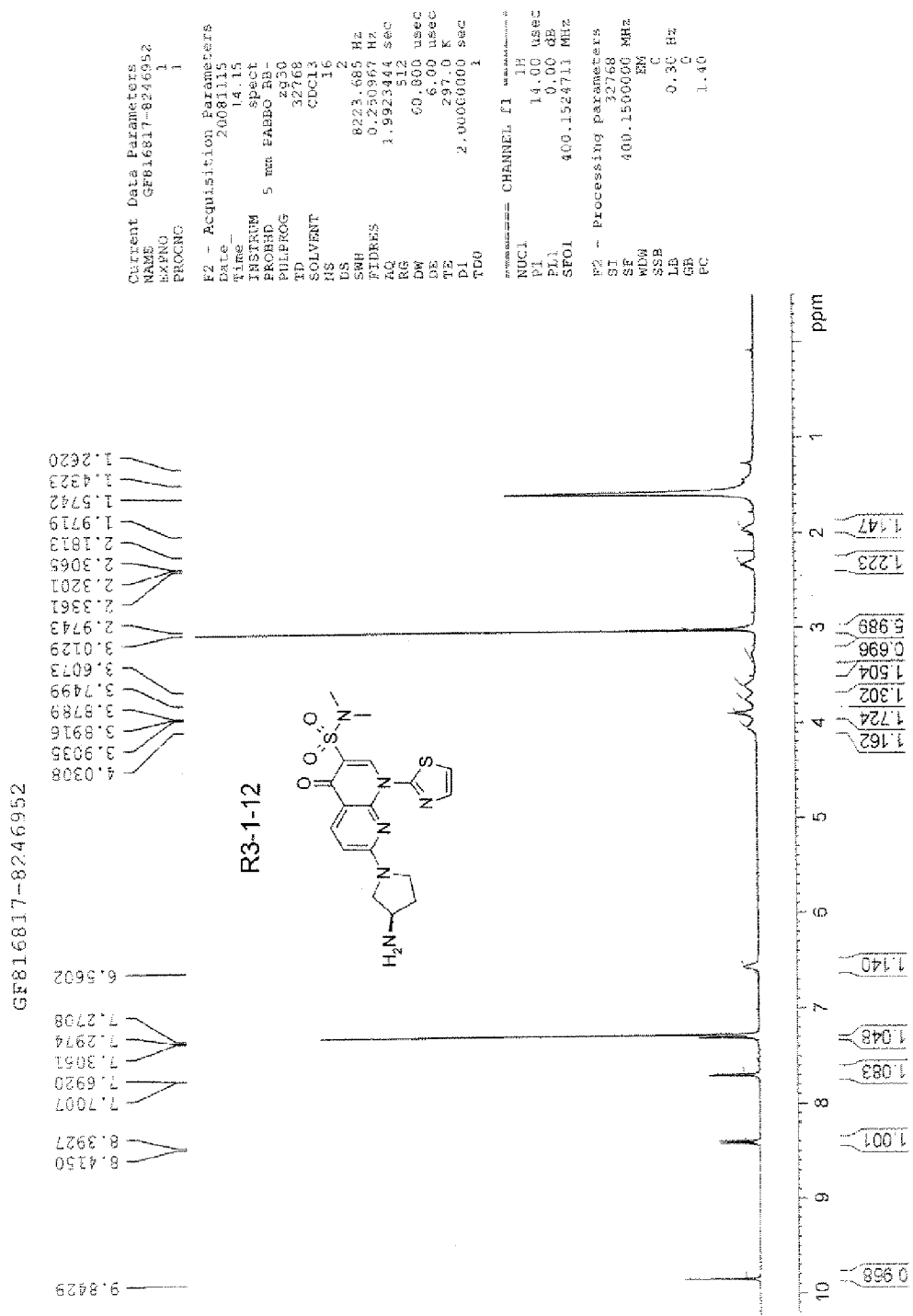
Figure 35:
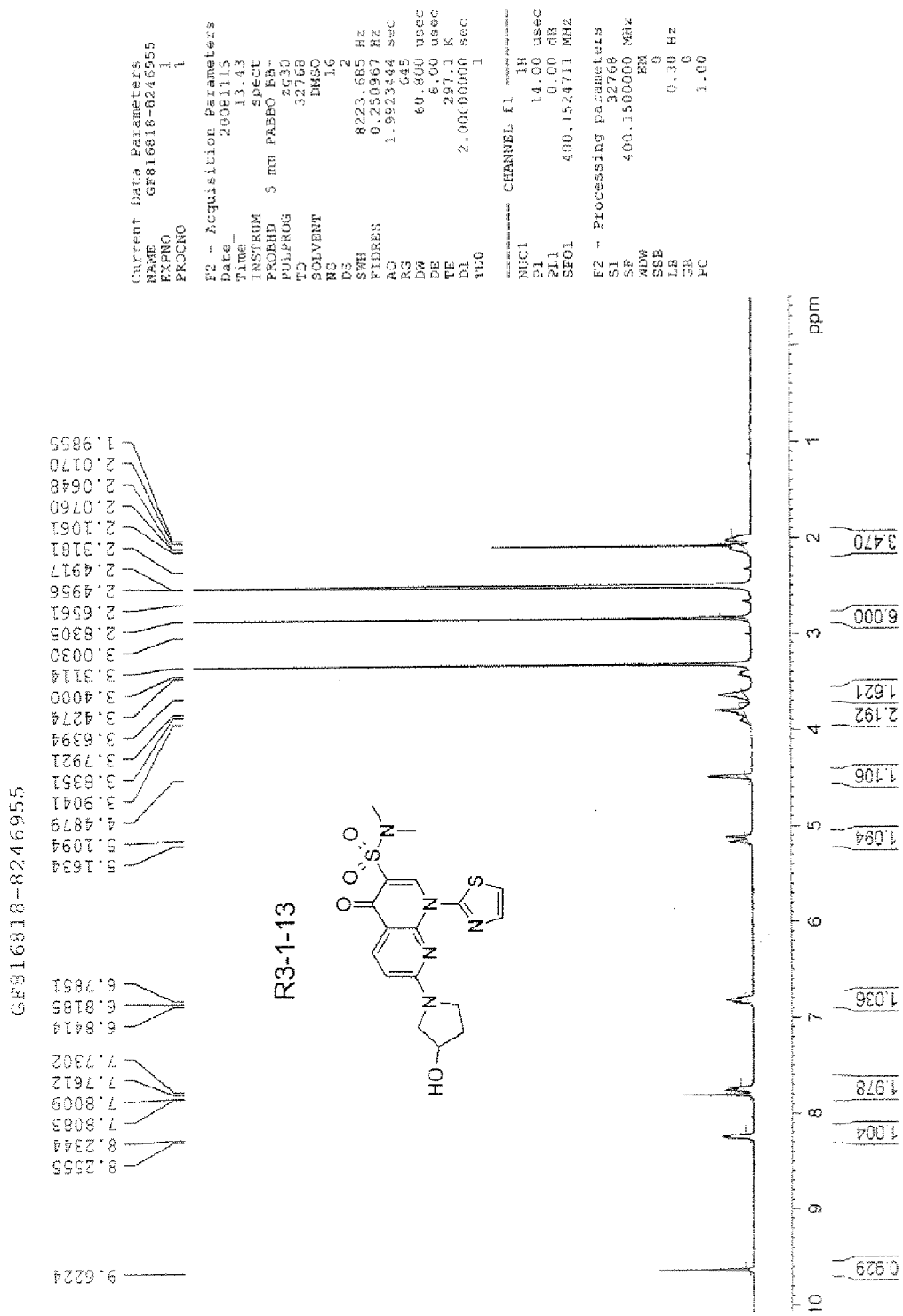
Figure 36:
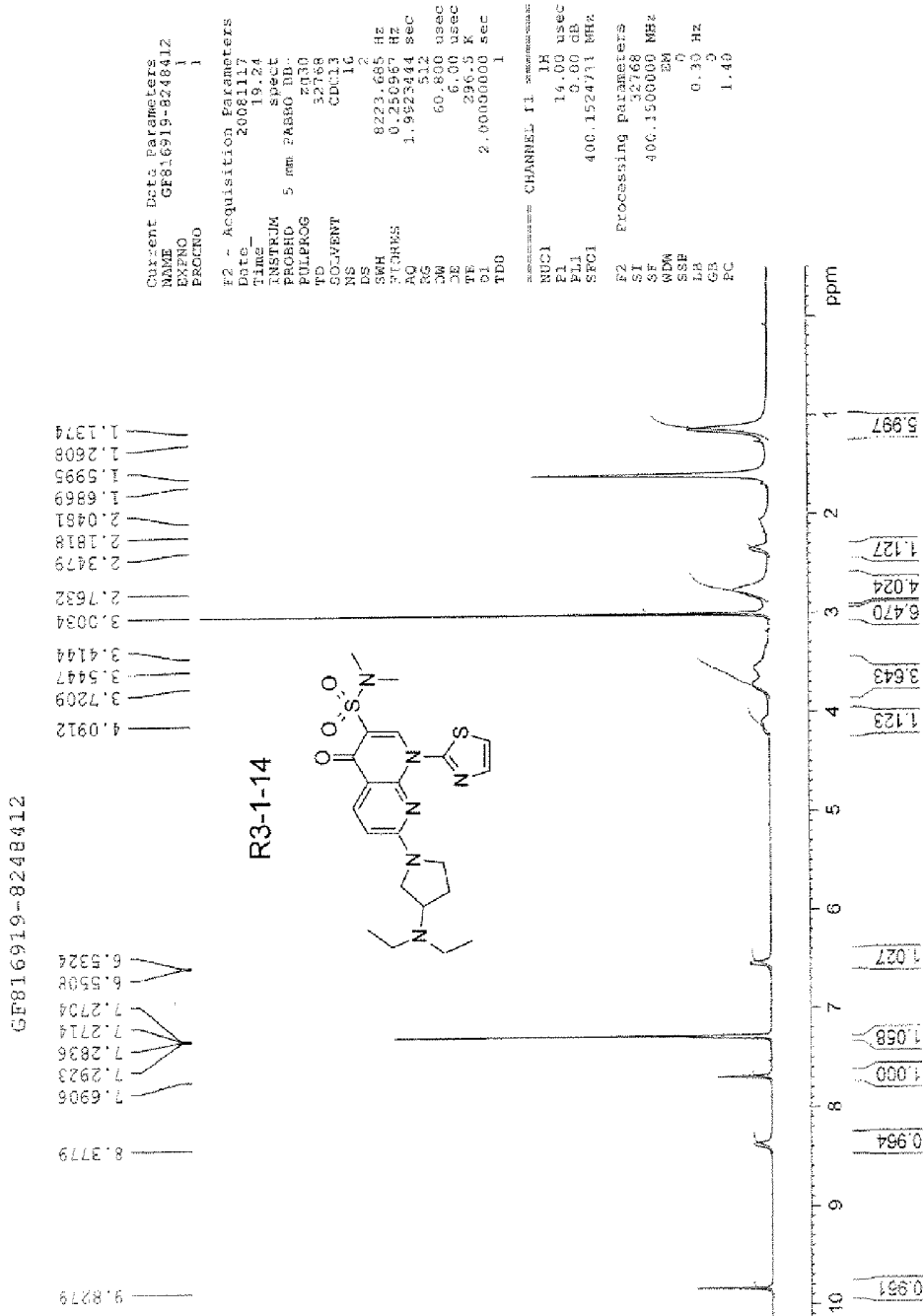
Figure 37:
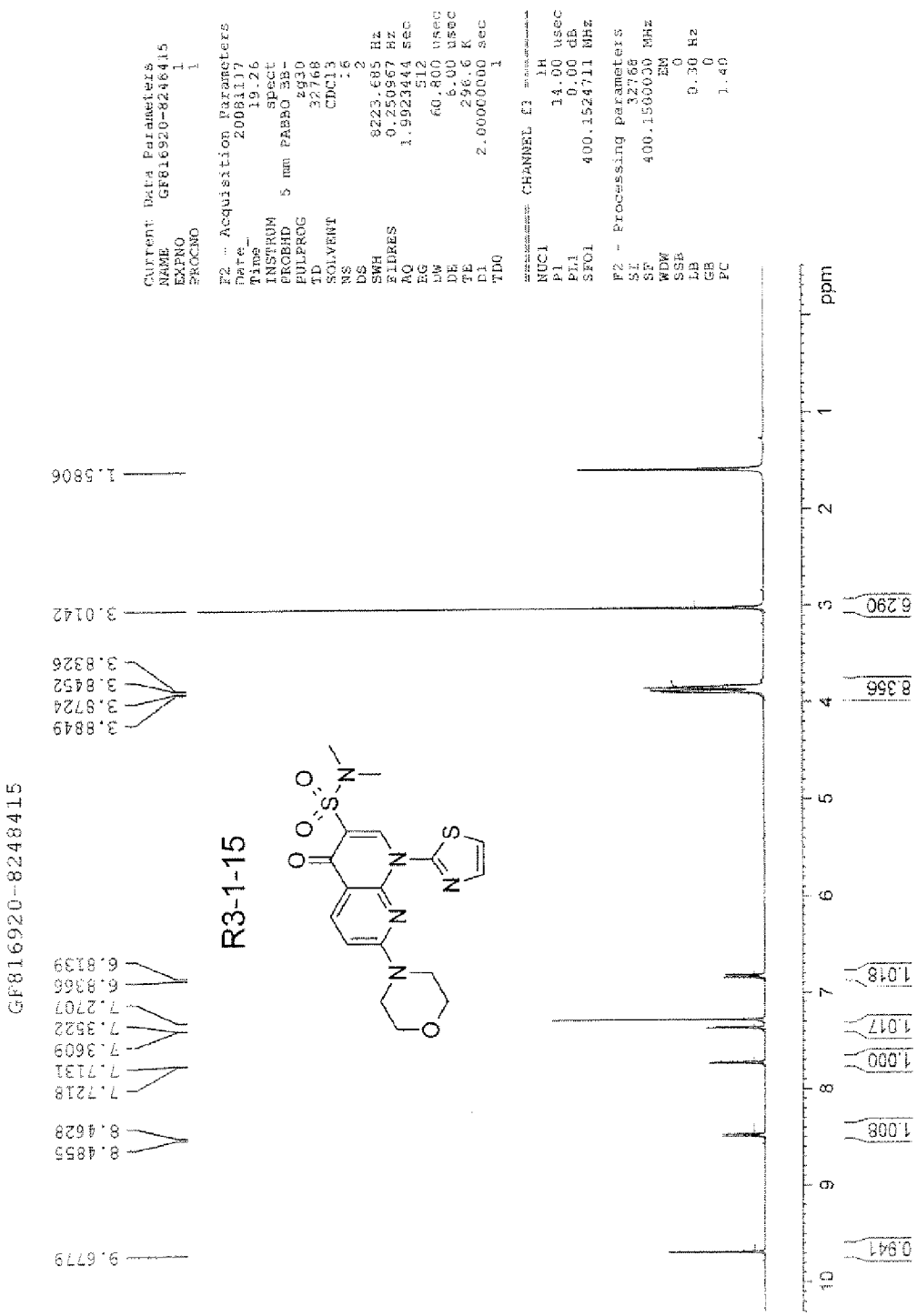
Figure 38:
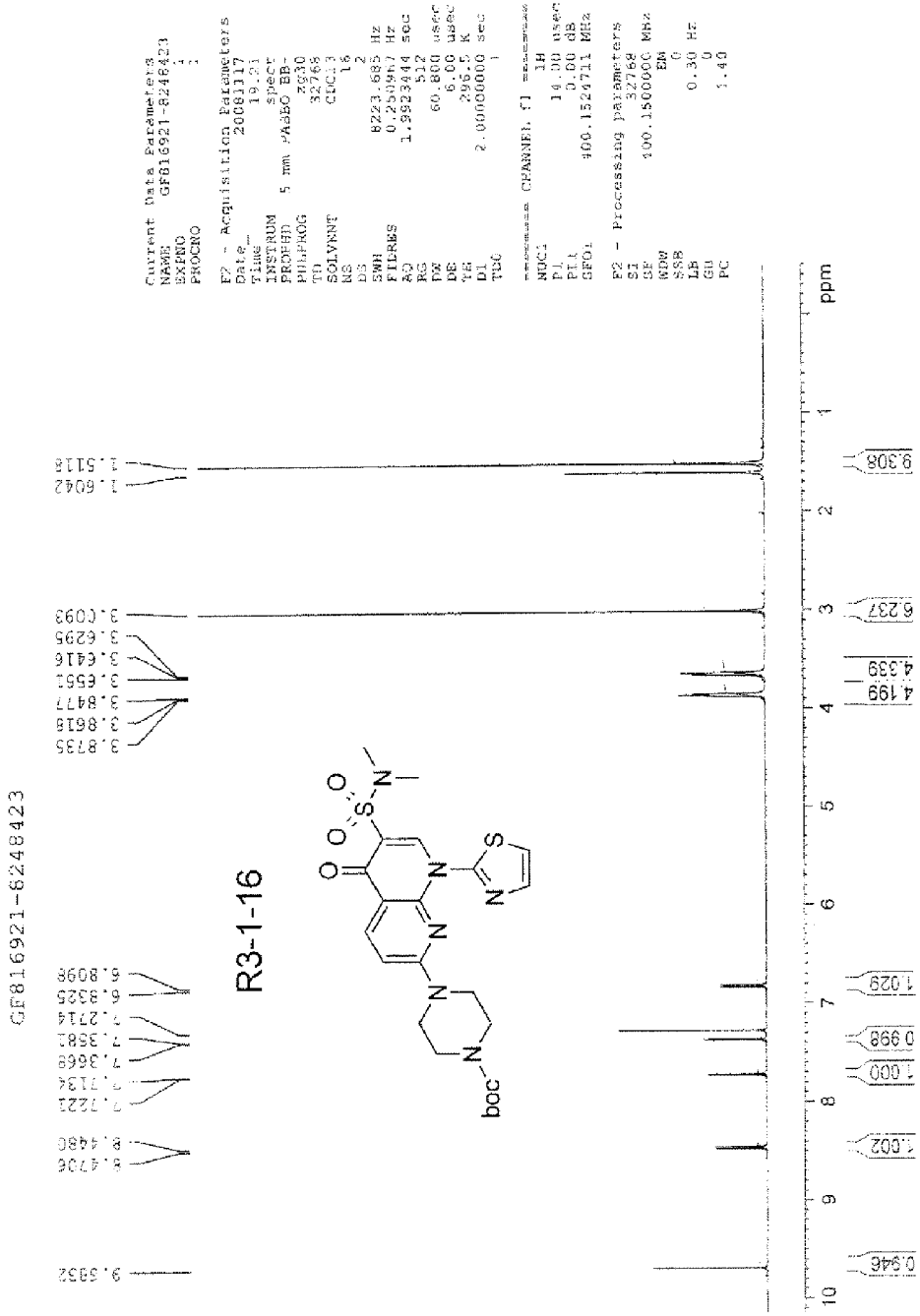
Figure 39:
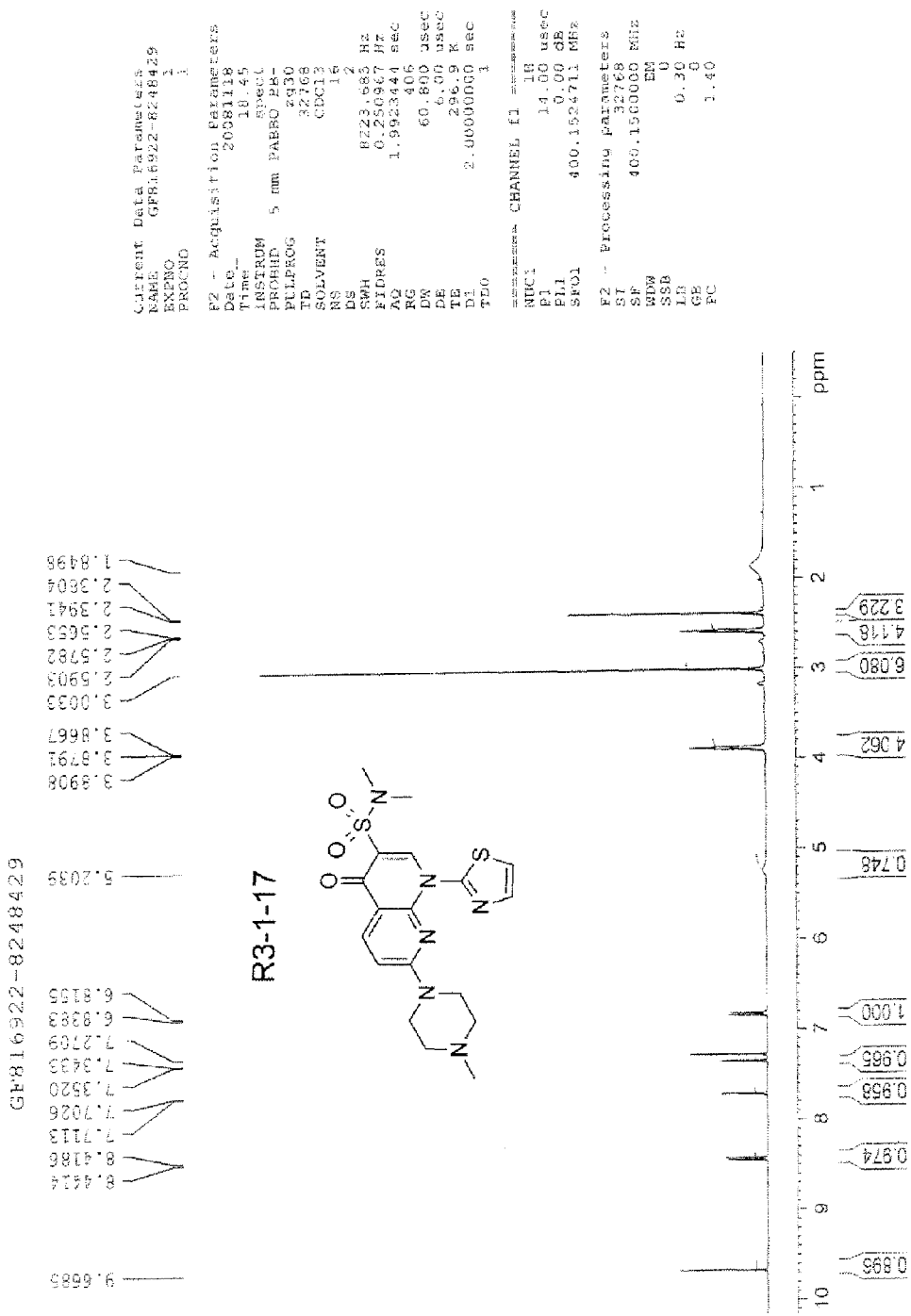
Figure 40:
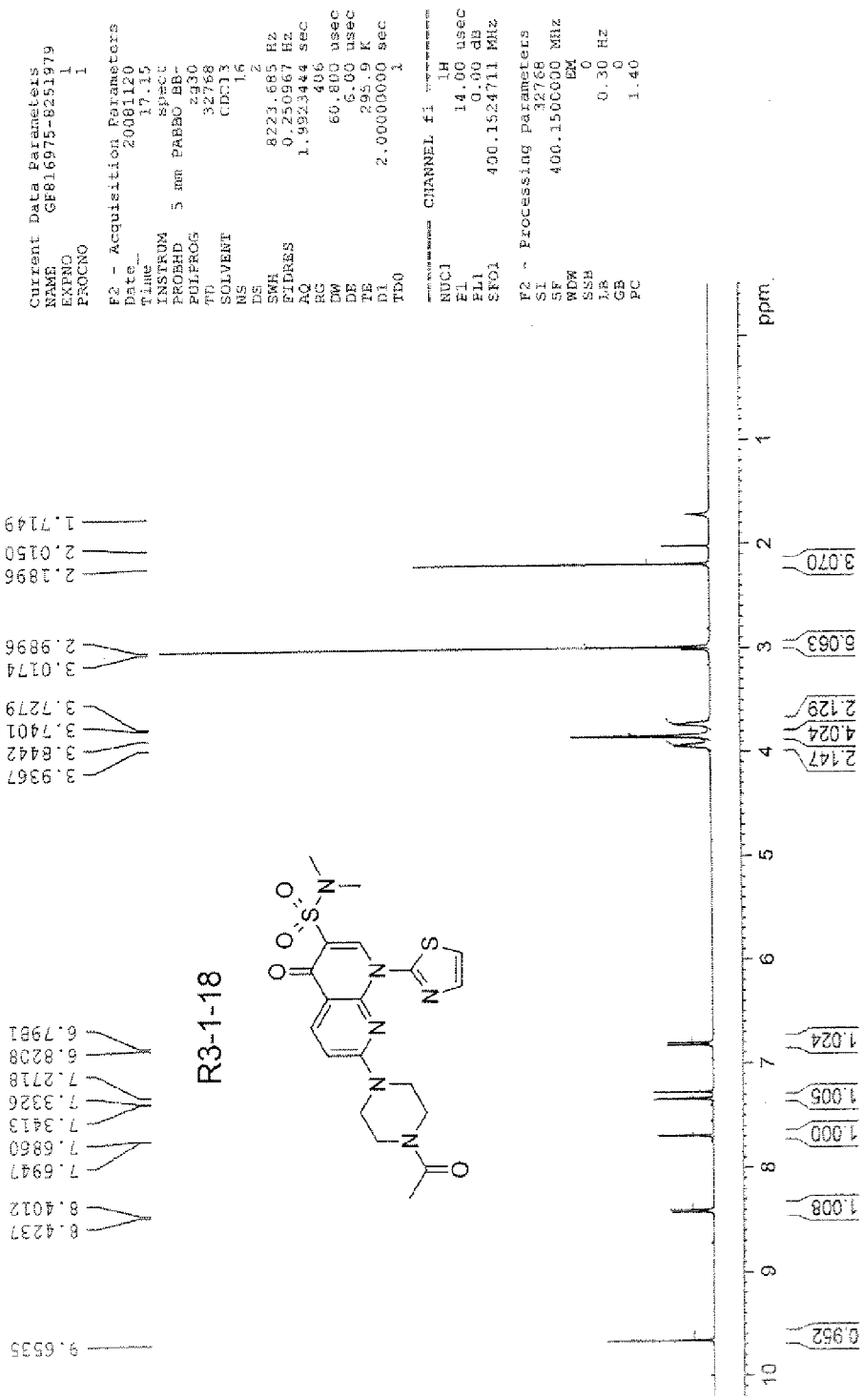
Figure 41:
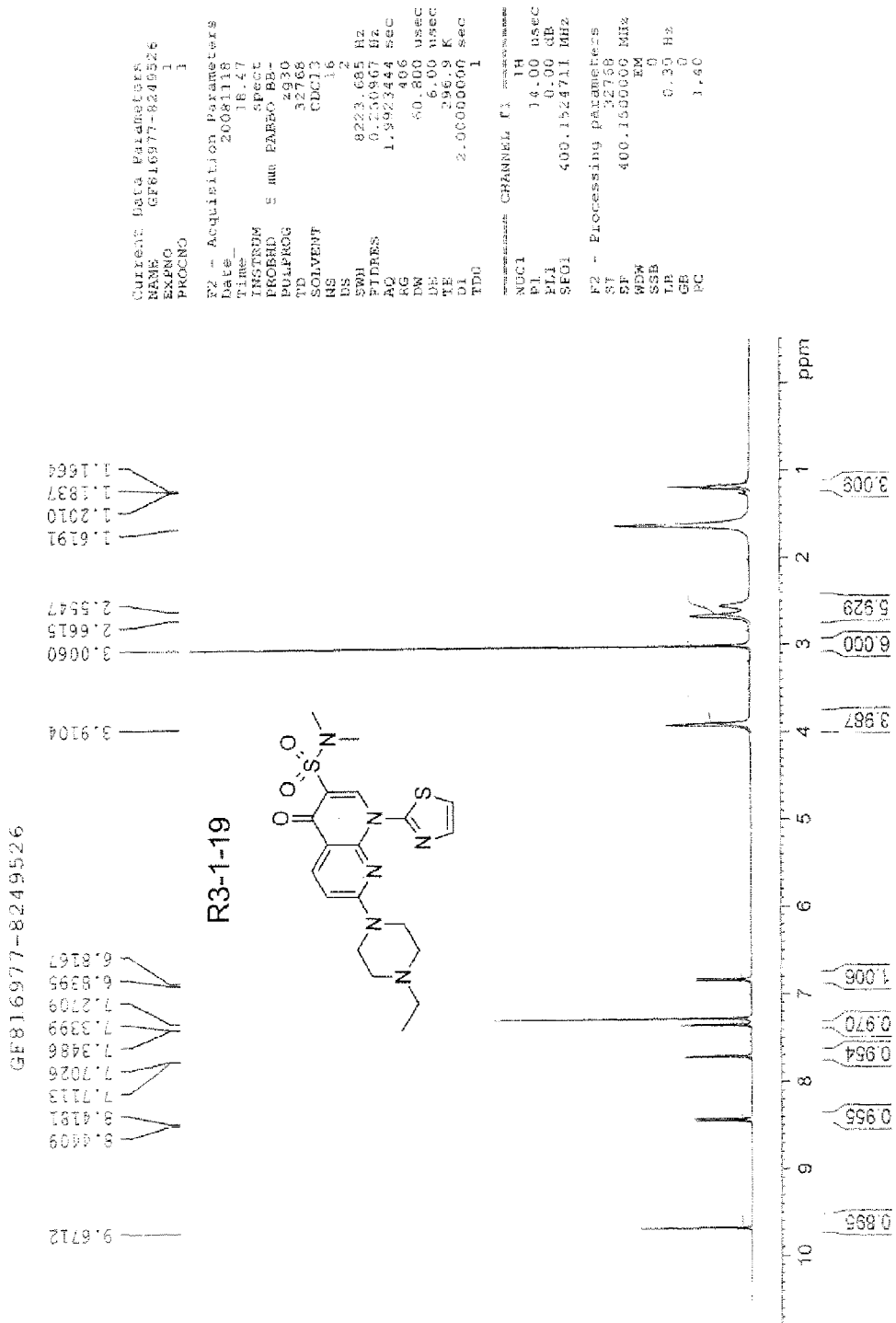
Figure 42:
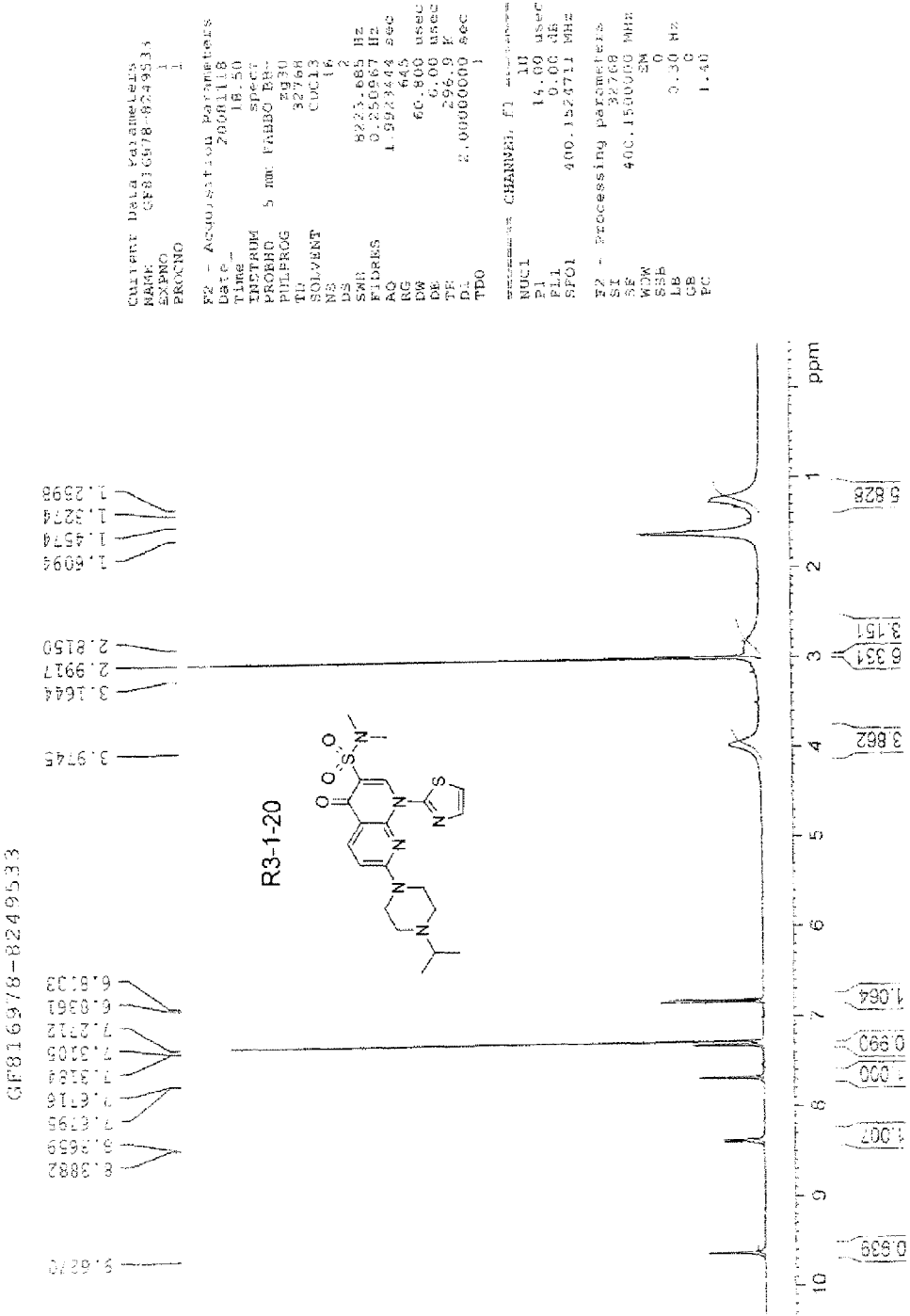
Figure 43:
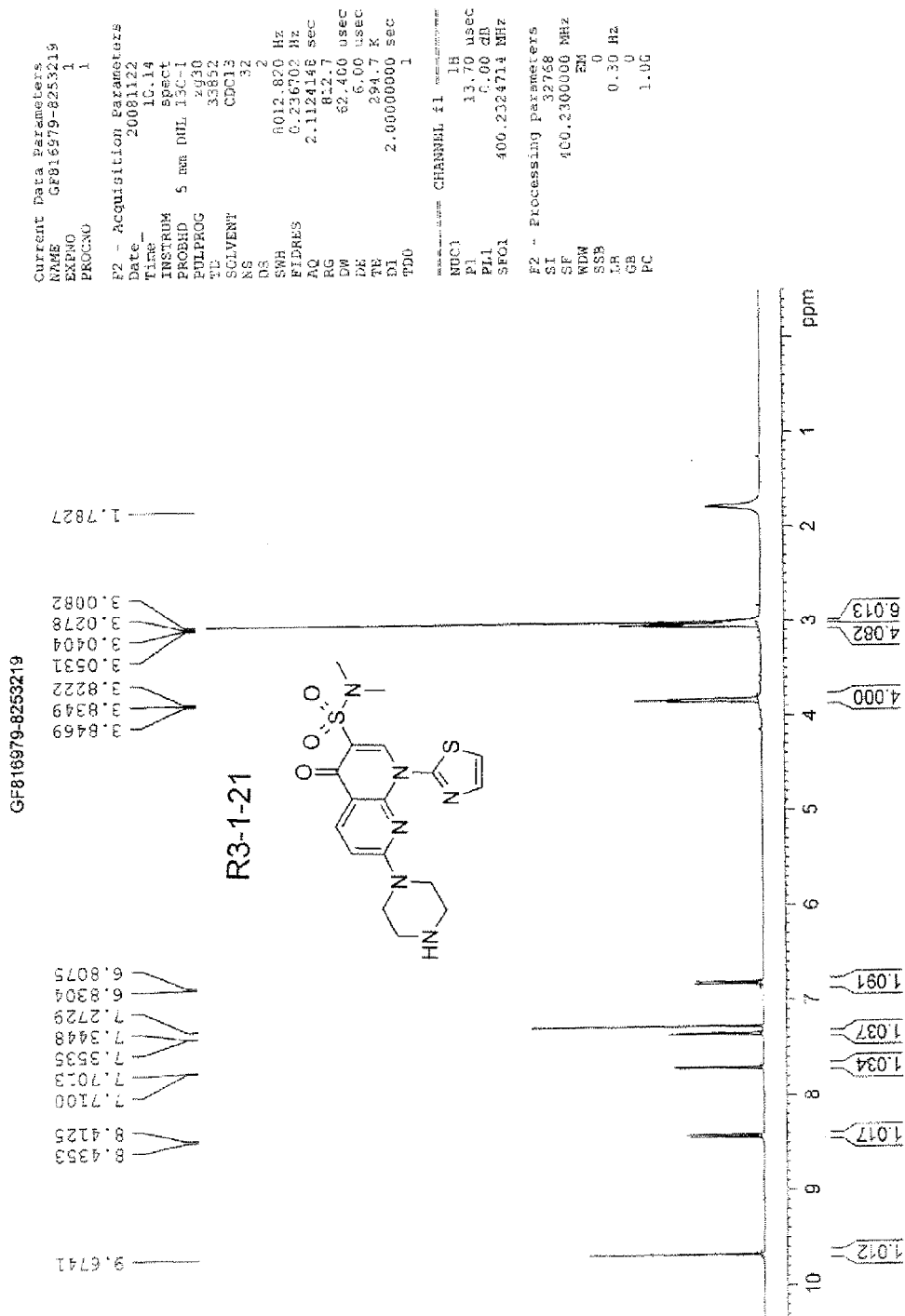
Figure 44:
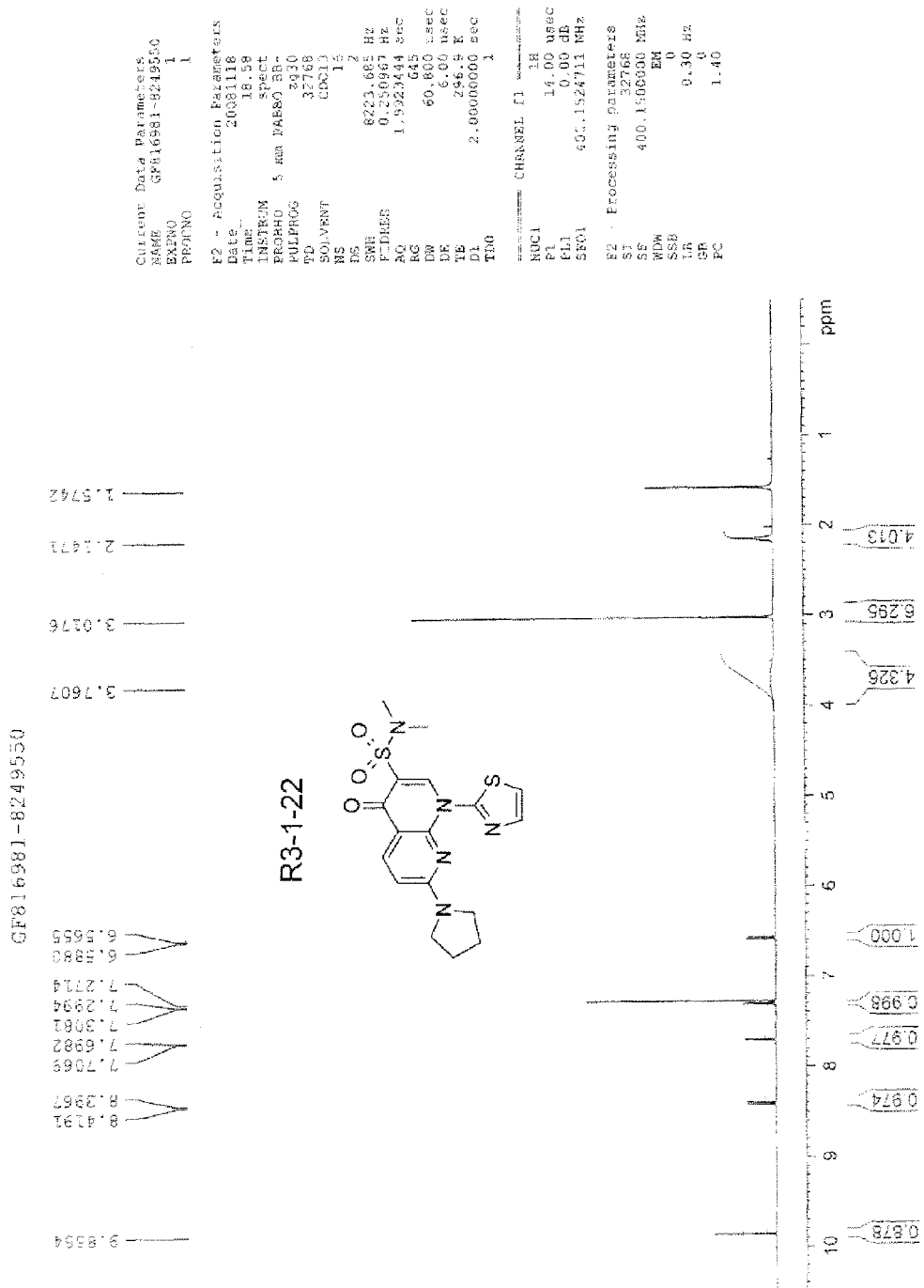

FIG. 28 provides an NMR spectrum for the compound of Example 28.
FIG. 29 provides an NMR spectrum for the compound of Example 29.
FIG. 30 provides an NMR spectrum for the compound of Example 30.
FIG. 31 provides an NMR spectrum for the compound of Example 31.
FIG. 32 provides an NMR spectrum for the compound of Example 32.
FIG. 33 provides an NMR spectrum for the compound of Example 33.
FIG. 34 provides an NMR spectrum for the compound of Example 34.
FIG. 35 provides an NMR spectrum for the compound of Example 35.
FIG. 36 provides an NMR spectrum for the compound of Example 36.
FIG. 37 provides an NMR spectrum for the compound of Example 37.
FIG. 38 provides an NMR spectrum for the compound of Example 38.
FIG. 39 provides an NMR spectrum for the compound of Example 39.
FIG. 40 provides an NMR spectrum for the compound of Example 40.
FIG. 41 provides an NMR spectrum for the compound of Example 41.
FIG. 42 provides an NMR spectrum for the compound of Example 42.
FIG. 43 provides an NMR spectrum for the compound of Example 43.
FIG. 44 provides an NMR spectrum for the compound of Example 44.

6. DETAILED DESCRIPTION

6.1 Definitions

Unless defined otherwise, all technical and scientific terms used herein have the same meaning as is commonly understood by one of ordinary skill in the art. All cited patents, applications, published applications and other publications are incorporated by reference in their entirety. In the event that there more than one definition is given for a term herein, those in this section prevail unless stated otherwise.

As used herein, "SNS-595" or "voreloxin" refers to (+)-1, 4-dihydro-7-[(3S,4S)-3-methoxy-4-(methylamino)-1-pyrrolidinyl]-4-oxo-1-(2-thiazolyl)-1,8-naphthyridine-3-carboxylic acid, and has the following structure:

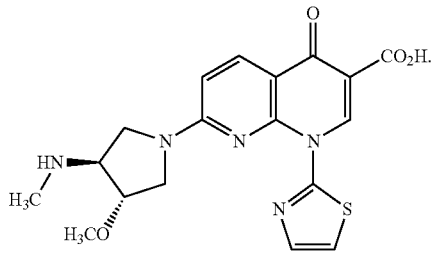 [SMILES: CN[C@H]1CN(c2ccc3c(=O)c(C(=O)O)cn(-c4nccs4)c3n2)C[C@@H]1OC]

As used herein, and unless otherwise indicated, the term "alkyl" refers to a saturated straight chain or branched hydrocarbon. In some embodiments, alkyl groups have 1 to 10, 1 to 6, or 1 to 3 carbon atoms. Representative saturated straight chain alkyl substituents include methyl, ethyl, n-propyl, n-butyl, n-pentyl, and n-hexyl; while saturated branched alkyl substituents include isopropyl, sec-butyl, isobutyl, tert-butyl, isopentyl, 2-methylbutyl, 3-methylbutyl, and the like.

As used herein, and unless otherwise indicated, the term "alkoxy" refers to the group having the formula —OR wherein R is alkyl or haloalkyl.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Cycloalkyl" refers to a monovalent monocyclic or bicyclic hydrocarbon group consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, and the like.

"Halo, "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, fluoromethyl, trifluoromethyl and others.

"Heterocyclyl" refers to a stable 3- to 15-membered aromatic or non-aromatic ring which consists of carbon atoms and from one to five heteroatoms selected from a group consisting of nitrogen, oxygen and sulfur. In one embodiment, the heterocyclic ring may be a monocyclic, bicyclic or tricyclic ring or tetracyclic ring, which may include fused or bridged rings; and the nitrogen or sulfur atoms in the heterocyclic ring may be optionally oxidized; the nitrogen atom may be optionally quaternized; and the heterocyclic ring may be aromatic, or partially or fully saturated. The heterocyclic ring may be attached to the main structure at any heteroatom or carbon atom which results in the creation of a stable compound. Exemplary heterocylic groups include, but are not limited to, morpholinyl, piperidinyl, piperazinyl, pyranyl, pyrrolidinyl, and others.

"Heteroaryl" refers to a heterocyclyl group as defined above which is aromatic. The heteroaryl group may be attached to the main structure at any heteroatom or carbon atom which results in the creation of a stable compound. Examples of such heteroaryl groups include, but are not limited to: pyrrolyl, pyridinyl, pyrimidinyl, and others.

"Aralkyl" refers to a group of the formula —$R_aR_b$ where $R_a$ is an alkyl group as defined above, substituted by $R_b$, an aryl group, as defined above, e.g., benzyl.

"Amine" or "amino" refers to a group having the formula —NR'R" wherein R' and R" are each hydrogen. "Alkylamine" refers to a group having the formula —NR'R" wherein R' is hydrogen or alkyl, and R" is alkyl. Thus, the term alkylamine includes monoalkylamine and dialkylamine.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein and unless otherwise indicated, the terms "treat," "treating" and "treatment" refer to alleviating or reducing the severity of a symptom associated with the disease or condition being treated.

The term "prevention" includes the inhibition of a symptom of the particular disease or disorder. In some embodiments, patients with familial history of cancer are candidates for preventive regimens. Generally, the term "preventing" refers to administration of the drug prior to the onset of symptoms, particularly to patients at risk of cancer.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein "subject" is an animal, typically a mammal, including human, such as a patient.

As used herein, the term "cancer" includes, but is not limited to, solid tumors and blood-borne tumors. Thus, term "cancer" refers to, inter alia, solid cancers and tumors of skin, tissues, and organs, including, but not limited to, cancers of the bladder, bone or blood, brain, breast, cervix, chest, colon, endometrium, esophagus, eye, head, kidney, liver, lung, mouth, neck, ovary, pancreas, prostate, rectum, stomach, testis, throat, and uterus. The term cancer also refers to hematologic or blood-borne cancers and tumors, sometimes referred to as "liquid tumors."

As used herein, "hematologic malignancy" refers to cancer affecting the blood or the body's blood-forming and immune system, i.e., the bone marrow and lymphatic tissue. Such cancers include leukemias, lymphomas (Non-Hodgkin's Lymphoma), Hodgkin's disease (also called Hodgkin's Lymphoma), and myeloma.

The term "leukemia" refers to malignant neoplasms of the blood-forming tissues. Leukemias include, but are not limited to, chronic lymphocytic leukemia, chronic myelocytic leukemia, acute lymphoblastic leukemia, acute myelogenous leukemia, acute myeloblastic leukemia, and hairy cell leukemia. The leukemia can be relapsed or refractory or resistant to conventional therapy.

As used herein "T-cell leukemia" refers to a disease in which certain cells of the lymphoid system called T lymphocytes or T cells are malignant. T cells are white blood cells that normally can attack virus-infected cells, foreign cells and cancer cells and produce substances that regulate the immune response.

The term "relapsed" refers to condition where signs of symptoms of the cancer return after a period of improvement.

The terms "refractory" and "resistant" refer to conditions where the cancer does not respond, or is resistant, to another therapy.

As used herein, the $IC_{50}$ refers to an amount, concentration or dosage of a particular test compound that achieves a 50% inhibition of a maximal response in an in vitro assay—such as a biochemical or enzymatic assay—that measures such response.

As used herein, and unless otherwise specified, the terms "therapeutically effective amount" and "effective amount" refer to an amount of a compound sufficient to provide a therapeutic benefit in the treatment, prevention, and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent. It may be recognized that a therapeutically effective amount of a compound may achieve different results when administered to different patients. In some cases, an amount of a compound that produces therapeutic benefit to one patient may yield little or no benefit for another patient, but is still considered a therapeutically effective amount. In some embodiments, a therapeutically effective amount of an active compound is an amount determined by the US Food and Drug Administration (or a correlative organization in another country or region) to be safe and effective in the treatment of a specified disease or disorder in a human patient.

As used herein and unless otherwise indicated, the term "pharmaceutically acceptable salt" includes, but is not limited to, salts of acidic or basic groups that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate (methylenesulfonate), methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts. General information regarding pharmaceutically acceptable salts may be found in Stahl P H, and Wermuth C G, eds. (2002) *Handbook of Pharmaceutical Salts Properties, Selection and Use* Wiley-VCH/VHCA Weinheim/Zürich.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein and unless otherwise indicated, the term "hydrate" means a compound provided herein or a salt thereof that further includes a stoichiometric or non-stoichiometric amount of water bound by non-covalent intermolecular forces.

The terms "co-administration" and "in combination with" include the administration of two therapeutic agents (for example, a compound of Formula I or Formula II and another anti-cancer agent or second agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents or manages an adverse effect from treatment with a compound of Formula I or Formula II.

6.2 Compounds

In certain embodiments, provided herein are compounds of Formula I,

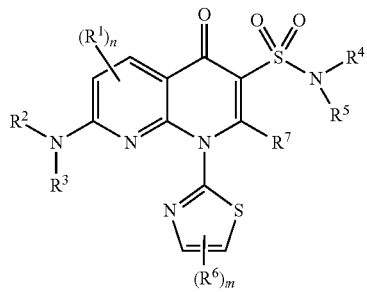

wherein $R^1$ is halo or alkyl;

$R^2$ and $R^3$ together with the nitrogen atom on which they are substituted form a substituted or unsubstituted heterocyclic ring, where substituents when present are selected from one, two or three $Q^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;

$R^4$ and $R^5$ are selected as follows:
i) $R^4$ and $R^5$ are each alkyl,
ii) $R^4$ and $R^5$ together with the nitrogen atom on which they are substituted form a substituted or unsubstituted heterocyclic ring; where substituents when present are one or two groups selected from halo and alkyl;

$R^6$ is halo, or alkyl;
$R^7$ is hydrogen, halo or alkyl;
n is 0 or 1; and
m is 0 or 1.

In certain embodiments, n is 0. In one embodiment, m is 0. In one embodiment, $R^7$ is hydrogen. In certain embodiments, n is 0, m is 0, and $R^7$ is hydrogen.

In certain embodiments according to Formula I, $R^2$ and $R^3$ together with the nitrogen atom on which they are substituted form a substituted or unsubstituted heterocyclic ring, where substituents when present are selected from one, two or three $Q^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl. In certain embodiments according to Formula I, $Q^1$ group is selected from methyl, ethyl, isopropyl, trifluoromethyl, amino, methylamino, dimethylamino, diethylamino, methoxy, methoxymethyl, hydroxyl, phenyl, trifluoromethylphenyl, cyclohexyl, piperidinyl, pyrrolidinyl, methylcarbonyl, and tert-butyloxycarbonyl. In one embodiment, $R^4$ and $R^5$ are each methyl. In one embodiment, $R^4$ and $R^5$ together with the nitrogen atom on which they are substituted form a substituted or unsubstituted heterocyclic ring. In one embodiment, $R^4$ and $R^5$ together with the nitrogen atom on which they are substituted form a piperidinyl ring.

In certain embodiments according to Formula I, $R^2$ and $R^3$ together with the nitrogen atom on which they are substituted form a substituted or unsubstituted 5 or 6 membered heterocyclic ring, where substituents when present are selected from one, two or three $Q^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl. In certain embodiments according to Formula I, $Q^1$ group is selected from methyl, ethyl, isopropyl, trifluoromethyl, amino, methylamino, dimethylamino, diethylamino, methoxy, methoxymethyl, hydroxyl, phenyl, trifluoromethylphenyl, cyclohexyl, piperidinyl, pyrrolidinyl, methylcarbonyl, and tert-butyloxycarbonyl. In one embodiment, $R^4$ and $R^5$ are each methyl. In one embodiment, $R^4$ and $R^5$ together with the nitrogen atom on which they are substituted form a substituted or unsubstituted heterocyclic ring. In one embodiment, $R^4$ and $R^5$ together with the nitrogen atom on which they are substituted form a piperidinyl ring.

In certain embodiments according to Formula I, $R^2$ and $R^3$ together with the nitrogen atom on which they are substituted form pyrrolidinyl, piperidinyl, piperazinyl or morpholinyl ring, where substituents when present are selected from one, two or three $Q^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl. In certain embodiments according to Formula I, $Q^1$ group is selected from methyl, ethyl, isopropyl, trifluoromethyl, amino, methylamino, dimethylamino, diethylamino, methoxy, methoxymethyl, hydroxyl, phenyl, trifluoromethylphenyl, cyclohexyl, piperidinyl, pyrrolidinyl, methylcarbonyl, and tert-butyloxycarbonyl. In one embodiment, $R^4$ and $R^5$ are each methyl. In one embodiment, $R^4$ and $R^5$ together with the nitrogen atom on which they are substituted form a substituted or unsubstituted heterocyclic ring. In one embodiment, $R^4$ and $R^5$ together with the nitrogen atom on which they are substituted form a piperidinyl ring.

In certain embodiments according to Formula I, $Q^1$ group is selected from methyl, ethyl, isopropyl, trifluoromethyl, amino, methylamino, dimethylamino, diethylamino, methoxy, methoxymethyl, hydroxyl, phenyl, trifluoromethylphenyl, cyclohexyl, piperidinyl, pyrrolidinyl, methylcarbonyl, and tert-butyloxycarbonyl. In one embodiment, $R^4$ and $R^5$ are each methyl. In one embodiment, $R^4$ and $R^5$ together with the nitrogen atom on which they are substituted form a substituted or unsubstituted heterocyclic ring. In one embodiment, $R^4$ and $R^5$ together with the nitrogen atom on which they are substituted form a piperidinyl ring.

In one embodiment, $R^4$ and $R^5$ are each methyl.

In one embodiment, $R^4$ and $R^5$ together with the nitrogen atom on which they are substituted form a substituted or unsubstituted heterocyclic ring.

In one embodiment, $R^4$ and $R^5$ together with the nitrogen atom on which they are substituted form a piperidinyl ring.

In one embodiment, provided herein are of compounds Formula IA

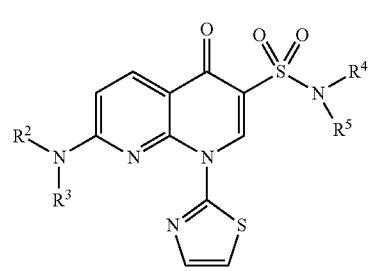

and pharmaceutically acceptable salts, solvates (e.g., hydrates), or clathrates thereof; wherein $R^2$ and $R^3$ together with the nitrogen atom on which they are substituted form a substituted or unsubstituted heterocyclic ring, where substituents when present are selected from one, two or three $Q^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;

$R^4$ and $R^5$ are selected as follows:
i) $R^4$ and $R^5$ are each alkyl; or
ii) $R^4$ and $R^5$ together with the nitrogen atom on which they are substituted form an unsubstituted heterocyclic ring.

In another embodiment, provided herein are compounds of Formula IB:

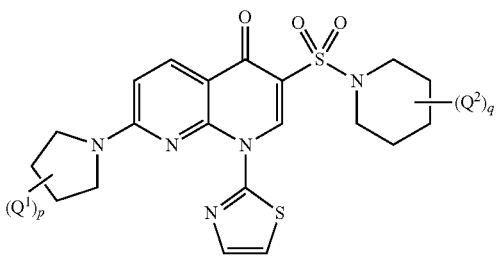

IB and pharmaceutically acceptable salts, solvates (e.g., hydrates), and clathrates, thereof, wherein p is 0 to 3, q is 0 or 1, and the other recited variables are as described elsewhere herein. In one embodiment, p is 0, 1 or 2; q is 0; and $Q^1$ is amino, alkylamino, hydroxyl, alkoxy, or alkoxyalkyl.

In one embodiment, provided herein are compounds of Formula IC:

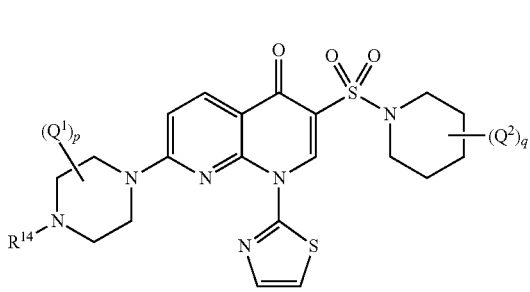

IC and pharmaceutically acceptable salts, solvates (e.g., hydrates), and clathrates, thereof, wherein $R^{14}$ is hydrogen, alkyl, haloalkyl, aryl, arylalkyl, alkylaryl, haloalkylaryl, alkylcarbonyl, cycloalkyl, haloalkylaryl, heteroaryl, heterocyclyl or alkyloxycarbonyl, and the other recited variables are as described elsewhere herein. In one embodiment, $R^{14}$ is hydrogen, methyl, ethyl, isopropyl, trifluoromethyl, phenyl, methylcarbonyl, cyclohexyl, trifluoromethylphenyl, pyridinyl, pyrrolidinyl, piperidinyl or tert-butyloxycarbonyl, $Q^1$ is methyl, p is 0, 1 or 2, and q is 0.

In another aspect, the compounds provided herein are of Formula ID:

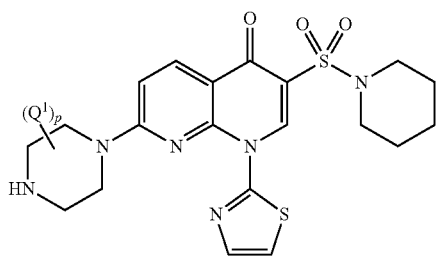

ID and pharmaceutically acceptable salts, solvates (e.g., hydrates), and clathrates thereof, wherein the variables are as described elsewhere herein.

In one embodiment, provided herein are compounds of Formula IE:

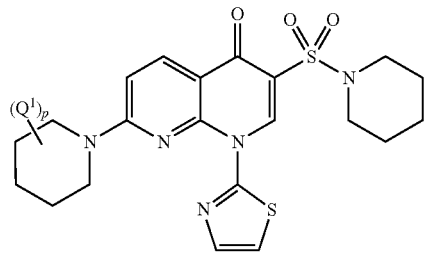

IE and pharmaceutically acceptable salts, solvates (e.g., hydrates), clathrates, esters, and prodrugs thereof, wherein the recited variables are as described elsewhere herein.

In another embodiment, provided herein are compounds of Formula IF:

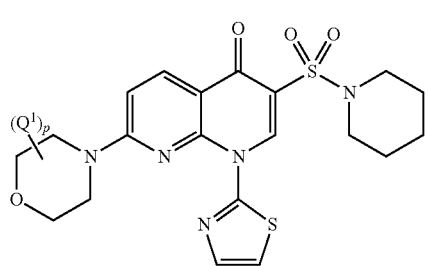

IF and pharmaceutically acceptable salts, solvates (e.g., hydrates), and clathrates thereof, wherein the recited variables are as described elsewhere herein.

In another embodiment, provided herein are compounds of Formula IG:

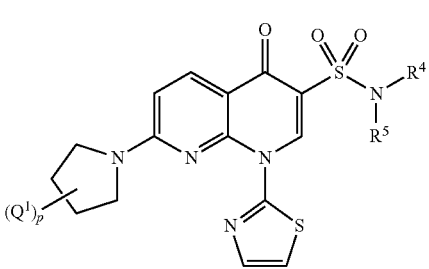

IG and pharmaceutically acceptable salts, solvates (e.g., hydrates), and clathrates, thereof, wherein p is 0 to 3, q is 0 or 1, and the other recited variables are as described elsewhere herein. In one embodiment, p is 0, 1 or 2; and $Q^1$ is amino, alkylamino, hydroxyl, alkoxy, or alkoxyalkyl; and $R^4$ and $R^5$ are each methyl.

In another embodiment, provided herein are compounds of Formula IH:

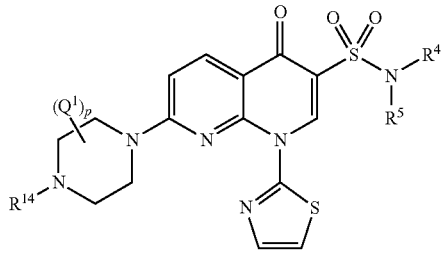

and pharmaceutically acceptable salts, solvates (e.g., hydrates), and clathrates, thereof, wherein $R^{14}$ is hydrogen, alkyl, haloalkyl, aryl, arylalkyl, alkylaryl, haloalkylaryl, alkylcarbonyl, cycloalkyl, haloalkylaryl, heteroaryl, heterocyclyl or alkyloxycarbonyl; $R^4$ and $R^5$ are each methyl; and the other recited variables are as described elsewhere herein. In one embodiment, $R^{14}$ is hydrogen, methyl, ethyl, isopropyl, trifluoromethyl, phenyl, methylcarbonyl, cyclohexyl, trifluoromethylphenyl, pyridinyl, pyrrolidinyl, piperidinyl or tert-butyloxycarbonyl, $Q^1$ is methyl, p is 0, 1 or 2, and $R^4$ and $R^5$ are each methyl.

In certain embodiments, provided herein are compounds of Formula II:

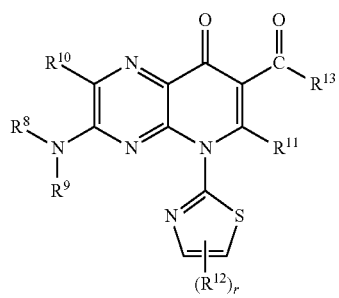

wherein $R^{10}$ and $R^{11}$ are each independently hydrogen, halo or alkyl;

$R^8$ and $R^9$ together with the nitrogen atom on which they are substituted form a substituted or unsubstituted heterocyclic ring, where substituents when present are selected from one or more $Q^3$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;

$R^{12}$ is halo or alkyl;

$R^{13}$ is hydroxyl or alkoxy; and r is 0 or 1.

In certain embodiments according to Formula II, $R^8$ and $R^9$ together with the nitrogen atom on which they are substituted form a substituted or unsubstituted heterocyclic ring, where substituents when present are selected from one, two or three $Q^3$ groups selected from alkyl, amino, alkylamino, alkoxy, hydroxyl, halo, haloalkyl, cycloalkyl, aryl, arylalkyl, haloalkylaryl, heterocyclyl, heteroaryl, alkoxyalkyl, alkylcarbonyl, and alkoxycarbonyl. In one embodiment, $Q^3$ group is selected from methyl, ethyl, isopropyl, trifluoromethyl, phenyl, trifluoromethylphenyl, amino, methylamino, dimethylamino, diethylamino, methoxy, methoxymethyl, hydroxyl, cyclohexyl, piperidinyl, pyrrolidinyl, methylcarbonyl, and tert-butyloxycarbonyl. In one embodiment, $R^{10}$ and $R^{11}$ are each hydrogen. In one embodiment, r is 0.

In certain embodiments according to Formula II, $R^8$ and $R^9$ together with the nitrogen atom on which they are substituted form a substituted or unsubstituted 5 or 6 membered heterocyclic ring, where substituents when present are selected from one, two or three $Q^3$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl. In one embodiment, $Q^3$ group is selected from methyl, ethyl, isopropyl, trifluoromethyl, phenyl, trifluoromethylphenyl, amino, methylamino, dimethylamino, diethylamino, methoxy, methoxymethyl, hydroxyl, cyclohexyl, piperidinyl, pyrrolidinyl, methylcarbonyl, and tert-butyloxycarbonyl. In one embodiment, $R^{10}$ and $R^{11}$ are each hydrogen. In one embodiment, r is 0.

In certain embodiments according to Formula II, $R^8$ and $R^9$ together with the nitrogen atom on which they are substituted form pyrrolidinyl, piperidinyl, piperazinyl or morpholinyl ring, where substituents when present are selected from one, two or three $Q^3$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl. In one embodiment, $Q^3$ group is selected from methyl, ethyl, isopropyl, trifluoromethyl, phenyl, trifluoromethylphenyl, amino, methylamino, dimethylamino, diethylamino, methoxy, methoxymethyl, hydroxyl, cyclohexyl, piperidinyl, pyrrolidinyl, methylcarbonyl, and tert-butyloxycarbonyl. In one embodiment, $R^{10}$ and $R^{11}$ are each hydrogen. In one embodiment, r is 0.

In one embodiment, $Q^3$ group is selected from methyl, ethyl, isopropyl, trifluoromethyl, phenyl, trifluoromethylphenyl, amino, methylamino, dimethylamino, diethylamino, methoxy, methoxymethyl, hydroxyl, cyclohexyl, piperidinyl, pyrrolidinyl, methylcarbonyl, and tert-butyloxycarbonyl. In one embodiment, $R^{10}$ and $R^{11}$ are each hydrogen. In one embodiment, r is 0.

In one embodiment, $R^{10}$ and $R^{11}$ are each hydrogen.

In one embodiment, r is 0.

In one embodiment, provided herein are compounds of Formula IIA:

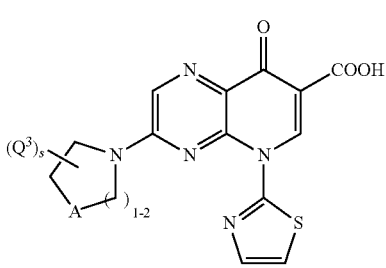

and pharmaceutically acceptable salts, solvates (e.g., hydrates), and clathrates thereof, wherein A is N or CH; s is 0, 1, 2 or 3; and $Q^3$ is selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl.

In one embodiment, provided herein are compounds of Formula IIB:

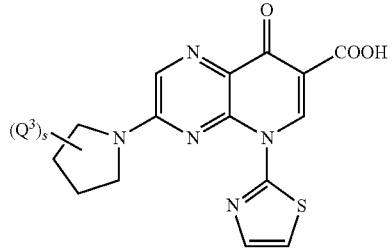

and pharmaceutically acceptable salts, solvates (e.g., hydrates), clathrates, esters, and prodrugs thereof, wherein $Q^3$ is selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl; and s is 0, 1, or 2.

In one embodiment, provided herein are compounds of Formula IIC:

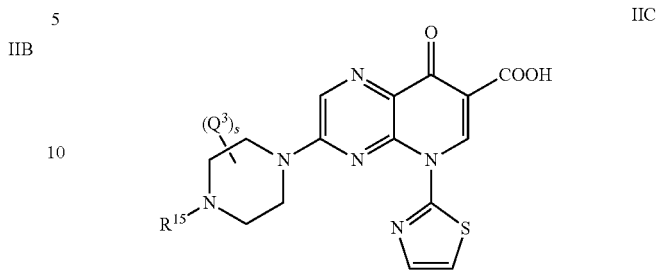

and pharmaceutically acceptable salts, solvates (e.g., hydrates), and clathrates thereof, wherein $R^{15}$ is hydrogen, alkyl, haloalkyl, aryl, arylalkyl, alkylaryl, haloalkylaryl, alkylcarbonyl, cycloalkyl, haloalkylaryl, heteroaryl, heterocyclyl or alkyloxycarbonyl, and the other recited variables are as described elsewhere herein. In one embodiment, $R^{15}$ is hydrogen, methyl, ethyl, isopropyl, trifluoromethyl, phenyl, methylcarbonyl, cyclohexyl, trifluoromethylphenyl, pyridinyl, pyrrolidinyl, piperidinyl or tert-butyloxycarbonyl, $Q^3$ is methyl; and s is 0, 1 or 2.

In one embodiment, provided herein is a compound selected from Tables I, II or III.

TABLE I

| Structure | $IC_{50}$ A549 (μM) | $IC_{50}$ HL60 (μM) |
|---|---|---|
| 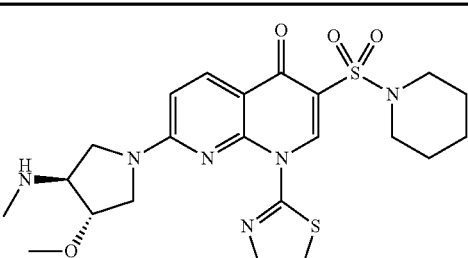 | A | A |
| 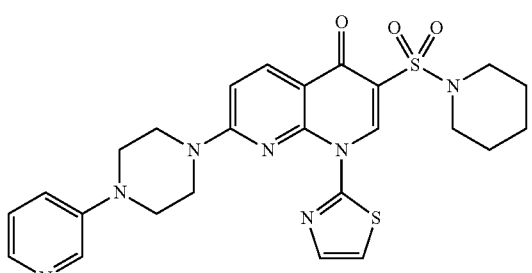 | A | B |
| 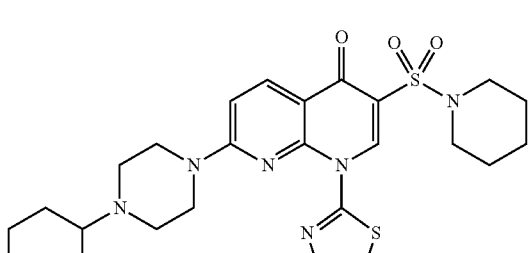 | A | A |

TABLE I-continued

| Structure | IC$_{50}$ A549 (μM) | IC$_{50}$ HL60 (μM) |
|---|---|---|
| (structure) | A | ND |
| (structure) | A | A |
| (structure) | A | A |
| (structure) | A | A |
| (structure) | ND | ND |

TABLE I-continued

| Structure | IC$_{50}$ A549 (μM) | IC$_{50}$ HL60 (μM) |
|---|---|---|
| | A | A |
| | B | C |
| | B | C |
| | A | A |
| | A | C |

TABLE I-continued

| Structure | IC$_{50}$ A549 (μM) | IC$_{50}$ HL60 (μM) |
|---|---|---|
| (7-(3-(diethylamino)pyrrolidin-1-yl)-4-oxo-1-(thiazol-2-yl)-N-piperidinyl-1,8-naphthyridine-3-sulfonamide) | A | A |
| (7-morpholino-4-oxo-1-(thiazol-2-yl)-N-piperidinyl-1,8-naphthyridine-3-sulfonamide) | B | C |
| (7-(4-boc-piperazin-1-yl)-4-oxo-1-(thiazol-2-yl)-N-piperidinyl-1,8-naphthyridine-3-sulfonamide) | ND | ND |
| (7-(4-methylpiperazin-1-yl)-4-oxo-1-(thiazol-2-yl)-N-piperidinyl-1,8-naphthyridine-3-sulfonamide) | A | C |
| (7-(4-acetylpiperazin-1-yl)-4-oxo-1-(thiazol-2-yl)-N-piperidinyl-1,8-naphthyridine-3-sulfonamide) | ND | ND |
| (7-(4-ethylpiperazin-1-yl)-4-oxo-1-(thiazol-2-yl)-N-piperidinyl-1,8-naphthyridine-3-sulfonamide) | ND | ND |

TABLE I-continued

| Structure | IC$_{50}$ A549 (μM) | IC$_{50}$ HL60 (μM) |
|---|---|---|
| [structure] | ND | ND |
| [structure] | A | A |
| [structure] | A | C |

TABLE II

| Structure | IC$_{50}$ A549 (μM) | IC$_{50}$ HL60 (μM) |
|---|---|---|
| [structure] | A | A |
| [structure] | C | C |

TABLE II-continued

| Structure | IC$_{50}$ A549 (μM) | IC$_{50}$ HL60 (μM) |
|---|---|---|
| [4-oxo-7-(4-cyclohexylpiperazin-1-yl)-1-(thiazol-2-yl)-1,8-naphthyridine-3-sulfonic acid dimethylamide] | A | B |
| [4-oxo-7-(4-(4-trifluoromethylphenyl)piperazin-1-yl)-1-(thiazol-2-yl)-1,8-naphthyridine-3-sulfonic acid dimethylamide] | ND | ND |
| [4-oxo-7-((S)-3-methylpiperazin-1-yl)-1-(thiazol-2-yl)-1,8-naphthyridine-3-sulfonic acid dimethylamide] | B | C |
| [4-oxo-7-((3R,5S)-3,5-dimethylpiperazin-1-yl)-1-(thiazol-2-yl)-1,8-naphthyridine-3-sulfonic acid dimethylamide] | B | B |
| [4-oxo-7-((S)-3-dimethylaminopyrrolidin-1-yl)-1-(thiazol-2-yl)-1,8-naphthyridine-3-sulfonic acid dimethylamide] | A | B |

TABLE II-continued

| Structure | IC$_{50}$ A549 (μM) | IC$_{50}$ HL60 (μM) |
|---|---|---|
| (2-methylpyrrolidinyl naphthyridinone thiazole sulfonamide) | ND | ND |
| (4-pyrrolidinylpiperidinyl naphthyridinone thiazole sulfonamide) | B | B |
| ((S)-2-methoxymethylpyrrolidinyl naphthyridinone thiazole sulfonamide) | C | C |
| ((R)-2-methoxymethylpyrrolidinyl naphthyridinone thiazole sulfonamide) | ND | ND |
| ((S)-3-aminopyrrolidinyl naphthyridinone thiazole sulfonamide) | A | A |
| (3-hydroxypyrrolidinyl naphthyridinone thiazole sulfonamide) | ND | ND |

TABLE II-continued

| Structure | IC$_{50}$ A549 (μM) | IC$_{50}$ HL60 (μM) |
|---|---|---|
| (diethylamino-pyrrolidinyl naphthyridinone sulfonamide thiazole) | ND | ND |
| (morpholino naphthyridinone sulfonamide thiazole) | C | C |
| (boc-piperazinyl naphthyridinone sulfonamide thiazole) | ND | ND |
| (methylpiperazinyl naphthyridinone sulfonamide thiazole) | ND | ND |
| (acetylpiperazinyl naphthyridinone sulfonamide thiazole) | ND | ND |
| (ethylpiperazinyl naphthyridinone sulfonamide thiazole) | ND | ND |

TABLE II-continued

| Structure | IC$_{50}$ A549 (μM) | IC$_{50}$ HL60 (μM) |
|---|---|---|
| (structure) | ND | ND |
| (structure) | B | B |
| (structure) | A | C |

TABLE III

| Structure | IC$_{50}$ A549 (μM) | IC$_{50}$ HL60 (μM) |
|---|---|---|
| (structure) | C | C |
| (structure) | C | C |

TABLE III-continued

| Structure | IC$_{50}$ A549 (μM) | IC$_{50}$ HL60 (μM) |
|---|---|---|
| | C | C |
| | C | C |
| | C | C |
| | C | C |
| | B | B |
| | B | C |

TABLE III-continued

| Structure | IC$_{50}$ A549 (μM) | IC$_{50}$ HL60 (μM) |
|---|---|---|
| [structure] | C | C |
| [structure] | C | C |
| [structure] | C | C |
| [structure] | C | C |
| [structure] | ND | ND |
| [structure] | C | C |

TABLE III-continued

| Structure | IC$_{50}$ A549 (μM) | IC$_{50}$ HL60 (μM) |
|---|---|---|
| *(structure)* | C | C |
| *(structure)* | C | C |
| *(structure)* | C | C |
| *(structure)* | ND | ND |
| *(structure)* | ND | ND |

TABLE III-continued

| Structure | IC$_{50}$ A549 (μM) | IC$_{50}$ HL60 (μM) |
|---|---|---|
| | C | C |
| | C | C |
| 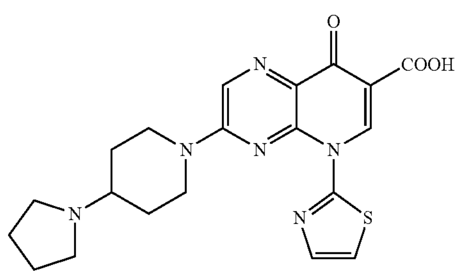 [SMILES: O=C(O)c1cn(-c2nccs2)c2nc(N3CCC(N4CCCC4)CC3)cnc2c1=O] | ND | ND |
| | C | C |

In Tables I, II and III, the $IC_{50}$ in MTT assays in A549 and HL60 cell lines is represented as follows: A<3 μM; 3 μM≦B≦10 μM; C>10 μM; and ND=no data.

6.3 Methods of Preparation

A general method for preparation of the compounds of Formula I or Formula II is described below and exemplary methods are described in the Examples section. Other compounds can be prepared using similar reactions and modifications thereof.

General Procedure for Preparing Compounds of Formula I and II

Scheme 1

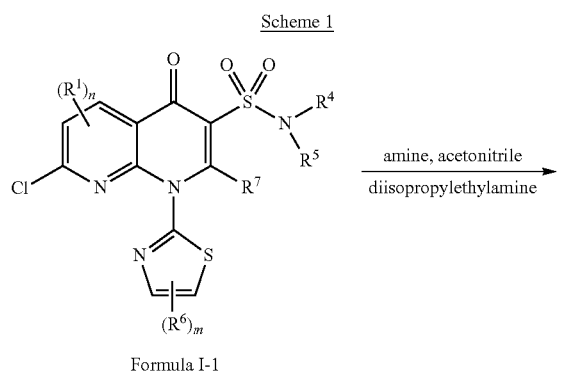

Formula I-1

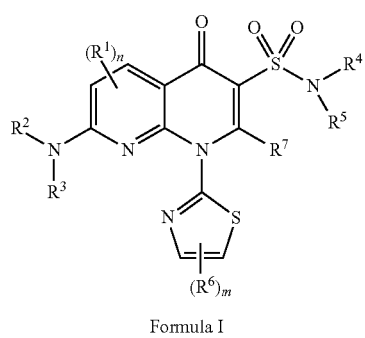

Formula I where $R^1$, $R^2$, $R^3$, $R^4$, $R^5$, $R^6$, $R^7$, m and n are as described elsewhere herein.

Scheme 2

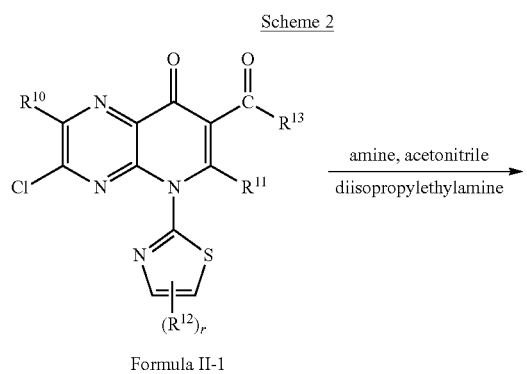

Formula II-1

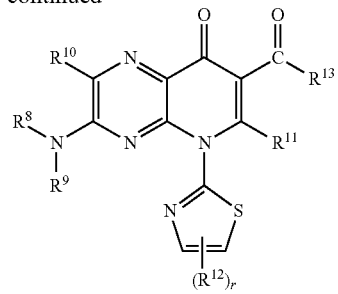

Formula II where $R^8$, $R^9$, $R^{10}$, $R^{11}$, $R^{12}$, $R^{13}$, and r are as described elsewhere herein.

Compounds of Formula I and Formula II can be prepared by reacting compounds of Formula I-1 and Formula II-1, respectively, with a suitable amine or a salt thereof under basic condition in a suitable solvent, such as, acetonitrile. Any suitable base can be used in the reaction. Exemplary bases include diisopropylethylamine, triethylamine etc.

The starting materials can be prepared by methods described in the Examples section, routine modifications of the exemplary methods or routine methods known to one of skill in the art.

6.4 Evaluation of the Activity of the Compounds

Standard physiological, pharmacological and biochemical procedures are available to evaluate the compounds for their biological activity.

Such assays include, for example, biochemical assays such as binding assays, radioactivity incorporation assays, as well as a variety of cell based assays.

Exemplary assays include MTT cell proliferation assay in A549 (Human lung adenocarcinoma epithelial cell line), and HL60 (Human promyelocytic leukemia cells) cell lines. Suitable cells include those derived through cell culture from patient samples (cancer cell lines) as well as cells derived using routine molecular biology techniques, e.g., retroviral transduction, transfection, mutagenesis, etc.

In an exemplary MTT assay, approximately 1,000 cells (A549 or HL60) are plated into each well of a 96-well plate. Cells are treated in duplicate with test compounds in a dose titration manner, typically 3-fold dilutions, eleven points per assay, with starting concentrations of 20 or 10 μM) or with DMSO-control (0.2% final concentration). Cells are treated for 72 hours (hr) or 96 hr before being analyzed by the MTT method. After 72 hr or 96 hr of compound treatment, 10 μL of MTT dye solution (5 mg/mL MTT dye [Sigma #M2128] in water) is added to each well and incubated at 37° C. for 2 hr. Following incubation, 100 μL of lysis buffer (10% SDS, 0.01 N HCl in water) is added to each well and incubated overnight at 37° C. The plate is analyzed the following day using a colorimetric plate reader at 595 nm wavelength. Values obtained for treatment samples are normalized to control samples.

The effects of the tested compounds on proliferation in the various cell lines are provided in Tables I, II and III.

In certain embodiments, the compounds provided herein were found to have $IC_{50}$ of less than about 20 μM in MTT cell proliferation assay in A549 and/or HL60 cell lines. In another embodiment, the compounds provided herein were found to have $IC_{50}$ of less than about 10 μM in MTT cell proliferation assay in A549 and/or HL60 cell lines. In another embodiment, the compounds provided herein were found to have $IC_{50}$ of less than about 5 µM, 4 µM, 3 µM, 2 µM, 1 µM, 0.5 µM or 0.3 µM in MTT cell proliferation assay in A549 and/or HL60 cell lines.

6.5 Methods of Use

Provided herein are methods of treating, preventing, and/or managing various cancers using a compound of Formula I or Formula II provided herein, or a pharmaceutically acceptable salt, solvate (e.g., hydrate), clathrate, ester, prodrug or stereoisomer thereof. Examples of cancers include solid tumors and hematologic cancers.

6.5.1 Solid Tumors

Accordingly, provided herein are methods of treating, managing, or preventing cancers, comprising administering a dose of about 1 mg/m$^2$ to about 150 mg/m$^2$ of a compound of Formula I or Formula II to a subject in need of such treatment, management or prevention. The cancer types include, but are not limited to, bladder cancer, brain cancer, breast cancer, cervical cancer, colon cancer (including colorectal cancer), esophageal cancer, head and neck cancer, liver cancer, lung cancer (both small cell and non-small cell), melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. In one embodiment, the methods encompass treating, preventing or managing colon cancer, pancreatic cancer, breast cancer, mesothelioma, cholangiocarcinoma, leiomyosarcoma, liposarcoma, melanoma, nasopharyngeal, neuroendocrine, ovarian cancer, renal cancer, salivary gland cancer, small cell lung cancer, or spindle cell carcinoma.

In one embodiment, the cancer is relapsed. In one embodiment, the cancer is refractory. In one embodiment, the cancer is resistant to conventional therapy.

6.5.2 Leukemias

The methods provided herein encompass treating, preventing or managing hematologic malignancies, including, but not limited to leukemias, lymphomas, and myeloma. The various forms of leukemias include, but are not limited to, chronic lymphocytic leukemia, chronic myeloid leukemia, acute lymphocytic leukemia, acute myelogenous leukemia, acute myeloblastic leukemia, and hairy cell leukemia. The leukemia can be relapsed or refractory or resistant to another treatment. In certain embodiments, the hematologic malignancy is promyelocytic leukemia, T-cell leukemia, or lymphoblastic leukemia.

The methods provided herein encompass treating patients who have been previously treated for cancer, but are non-responsive to standard therapies, as well as those who have not previously been treated. Also encompassed are methods of treating patients regardless of patient's age, although some diseases or disorders are more common in certain age groups. Further provided are methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In other embodiments, a compound of Formula I or Formula II is administered in combination with another drug ("second active agent") or another therapy for treating, managing, or preventing cancer. Second active agents include small molecules and large molecules (e.g., proteins and antibodies), examples of which are provided herein, as well as stem cells or cord blood. Methods, or therapies, that can be used in combination with the administration of an a compound of Formula I or Formula II include, but are not limited to, surgery, immunotherapy, biological therapy, radiation therapy and other non-drug based therapies presently used to treat, prevent or manage cancer. Various dosing regimens for administration of a compound of Formula I or Formula II alone and/or in combination therapy are discussed herein.

Also provided are pharmaceutical compositions (e.g., single unit dosage forms) that can be used in methods disclosed herein. Particular pharmaceutical compositions comprise a compound of Formula I or Formula II and a second active agent.

6.6 Doses and Dosing Regimens

In one embodiment, the methods of treating, preventing or managing cancers provided herein comprise administering to a patient a compound of Formula I, alone or in combination with a second active agent, on the basis of body surface area (BSA). Body surface area can be calculated, for example, with the Mosteller formula wherein:

$$BSA\ (m^2) = [(height\ (cm) \times weight\ (kg))/3600]^{1/2}.$$

In one embodiment, a compound of Formula I or Formula II may be administered orally or intravenously and in single or divided daily doses in an amount of about 1 to about 500 mg/m$^2$, 1 to about 300 mg/m$^2$, 10 mg/m$^2$ to 300 mg/m$^2$, 20 mg/m$^2$ to 150 mg/m$^2$ or 10 mg/m$^2$ to 120 mg/m$^2$.

In certain embodiments, the administered dose of a compound of Formula I or Formula II can be delivered as a single dose such as, for example, an IV push of 10-15 minutes duration (e.g., a single bolus IV injection) or over time such as, for example, a 24-hour period (e.g., continuous infusion over time or divided bolus doses over time) and is repeated as necessary, for example, until the patient experiences stable disease or regression or until the patient experiences disease progression or unacceptable toxicity. Stable disease or lack thereof is determined by methods known in the art, such as evaluation of patient symptoms, physical examination and other commonly accepted evaluation modalities. For example, stable disease for solid tumors generally means that the perpendicular diameter of measurable lesions has not increased by 25% or more from the last measurement. See e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The amount of the pharmaceutical composition administered according to the methods provided herein will depend on the subject being treated, the severity of the disorder or symptom of the disorder, the manner of administration, the frequency of administration and the judgment of the prescribing physician.

In some embodiments, the frequency of administration of a compound of Formula I or Formula II is in the range of about a daily dose to about a monthly dose. In certain embodiments, administration is once per day, once every other day, twice per week (e.g., dosing on days 1, 4, 8 and 11), once every week, once every two weeks, once every three weeks, or once every four weeks. In one embodiment, the pharmaceutical composition provided herein is administered weekly.

In certain embodiments, a compound of Formula I or Formula II is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one embodiment, a compound of Formula I or Formula II is administered weekly in a single or divided doses in a three to six week cycle with a rest period of about 1 to about 30 days. In another embodiment, a compound of Formula I or Formula II is administered weekly in a single or divided doses for one week, two weeks, three weeks, four weeks, five weeks or six weeks with a rest period of 1, 3, 5, 7, 9, 12, 14, 16, 18, 20, 22, 24, 26, 28, 29 or 30 days. In some embodiments, the waiting period is 7 days. In some embodiments, the waiting period is 14 days. In some embodiments, the waiting period is 28 days. In one embodiment, the waiting period is until there is sufficient bone marrow recovery. The frequency, number and length of dosing cycles can be increased or decreased. Thus, another embodiment encompasses the administration of a compound of Formula I or Formula II for more cycles than are typical when it is administered alone.

6.7 Combination Therapy

In the methods and compositions provided herein, a compound of Formula I or Formula II can be used with or combined with other pharmacologically active compounds ("second active agents"). It is believed that certain combinations work synergistically in the treatment of particular types of cancers. A compound of Formula I or Formula II can also work to alleviate adverse effects associated with certain second active agents, and some second active agents can be used to alleviate adverse effects associated with a compound of Formula I or II.

6.7.1 Other Active Agents

One or more other active agents can be used in the methods and compositions provided herein together with a compound of Formula I or Formula II. Other active agents can be large molecules (e.g., antibodies or other proteins) or small molecules (e.g., synthetic inorganic, organometallic or organic molecules).

Recombinant and mutated forms of GM-CSF can be prepared as described in U.S. Pat. Nos. 5,391,485; 5,393,870 and 5,229,496, all of which are incorporated herein by reference. Recombinant and mutated forms of G-CSF can be prepared as described in U.S. Pat. Nos. 4,810,643; 4,999,291; 5,528,823 and 5,580,755, all of which are incorporated herein by reference.

Also provided for use in combination with a compound of Formula I or Formula II are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Large molecule active agents may be administered in the form of anti-cancer vaccines. For example, vaccines that secrete or cause the secretion of, cytokines such as IL-2, G-CSF, and GM-CSF can be used in the methods and pharmaceutical compositions provided. See, e.g., Emens, L. A. et al., Curr. Opinion Mol. Ther. 3(1):77-84 (2001).

In certain embodiments, the second agent may be an agent that mediates its cytotoxicity through the DNA-PK pathway. Examples of such agents include compounds that inhibit non-homologous endjoining repair such as DNA-PK inhibitors. As used herein, and unless otherwise indicated, the term "DNA-PK inhibitor" means an agent that inhibits or interferes with a signaling pathway mediated by DNA-PK. The inhibition of the activity of DNA-PK may be direct (e.g., a catalytic inhibitor of DNA-PK itself) or indirect (e.g., an agent that interferes with the formation of the active DNA-PK complex (DNA-PK, Ku70 and Ku80)). In one embodiment, the second agent is SNS-595. Other examples include, but are not limited to, ligase IV inhibitors and apoptosis enhancing agents such as, but not limited to, caspase-9 activators, caspase-3 activators, and HSP90 inhibitors.

Second agents that are small molecules can also be used to alleviate adverse effects associated with the administration of a compound of Formula I or II. However, like some large molecules, many are believed to be capable of providing a synergistic effect when administered with (e.g., before, after or simultaneously) a compound of Formula I or II. Examples of small molecule second active agents include, but are not limited to, anti-cancer agents, antibiotics, immunosuppressive agents, and steroids.

Examples of anti-cancer second agents include, but are not limited to, alkylating agents, anti-neoplastic agents, anti-metabolites (e.g., folate analogs, purine analogs, adenosine analogs, pyrimidine analogs, and substituted ureas), platinum coordination complexes, topoisomerase II inhibitors, and radiation.

It will also be appreciated that a compound of Formula I or Formula II and pharmaceutically acceptable compositions comprising a compound of Formula I or Formula II can be employed in complementary combination therapies with second agents or medical procedures. Thus, a compound of Formula I or Formula II and pharmaceutically acceptable compositions thereof can be administered concurrently with, prior to, or subsequent to, one or more other desired active agents or medical procedures. The particular combination of therapies (agents or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a compound of Formula I or Formula II may be administered concurrently with another active agent used to treat the same disorder), or they may achieve different effects (e.g., control of any adverse effects). Non-limiting examples of such agents and procedures include surgery, radiotherapy (e.g., gamma-radiation, neutron beam radiotherapy, electron beam radiotherapy, proton therapy, brachytherapy, and systemic radioisotopes), endocrine therapy, biologic response modifiers (interferons, interleukins, and tumor necrosis factor (TNF) to name a few examples), hyperthermia and cryotherapy, agents to attenuate any adverse effects (e.g., antiemetic agents), and other approved chemotherapeutic anticancer second agents.

Examples of chemotherapeutic anticancer agents that may be used as second agents in combination with a compound of Formula I or Formula II include, but are not limited to, alkylating agents (e.g., mechlorethamine, chlorambucil, cyclophosphamide, melphalan, ifosfamide), antimetabolites (e.g., methotrexate), aurora kinase inhibitors (e.g., SNS-314, AZD-1152, PHA-739358, AT-9283), purine antagonists and pyrimidine antagonists (e.g., 5-fluorouracil (5-FU), gemcitabine), spindle poisons (e.g., vinca alkaloids such as vinblastine, vincristine, vinorelbine), mitotic inhibitors (e.g., taxanes such as paclitaxel, docetaxel, taxotere), topoisomerase II inhibitors or poisons (e.g., epipodophyllotoxins such as etoposide, teniposide; anthracyclines such as doxorubicin, daunorubicin, idarubicin), topoisomerase I inhibitors (e.g., irinotecan, topotecan, camptothecin), anti-neoplastic antibiotics (e.g., bleomycin, mitomycin, aphidicolin; anthracenediones such as mitoxantrone), nitrosoureas (e.g., carmustine, lomustine), inorganic ions (e.g., platinum complexes such as cisplatin, carboplatin, oxaliplatin), enzymes (e.g., asparaginase), hormones and hormone analogs (e.g., tamoxifen, leuprolide, flutamide, megestrol), EGFR (Her1, ErbB-1) inhibitors (e.g., gefitinib, erlotinib, lapatinib, BMS-599626, BMS-690514, PF-00299804, XL-647, BIBW-2992, ARRY-334543), HER antibodies (e.g., cetuximab, panitumumab, trastuzumab), CD20 antibodies (e.g., rituximab, ofatumumab), antibody derivatives (e.g., ranibizumab), IMIDs (e.g., thalidomide, lenalidomide), HDAC inhibitors (e.g., vorinostat, belinostat, panobinostat, ITF-2357, SNDX-275, CI-994, apicidin, depsipeptide, trapoxin, depeudecin, SK-7068, phenylbutyrate, valproic acid), Bcl-2 inhibitors (e.g., oblimersen, obatoclax), VEGFR-inhibitors (e.g., sorafenib, sunitinib, vatalanib, AMG-706, CP-547632, pazopanib, ABT-869, cediranib), VEGF traps (e.g., aflibercept), anti-VEGF antibodies (e.g., bevacizumab), proteasome inhibitors (e.g., bortezomib), cyclin-dependent kinase (cdk) inhibitors (e.g., SNS-032, seliciclib), aromatase inhibitors (e.g., anastrozole, exemestane, letrozole), mTOR inhibitors (e.g., temsirolimus, rapamycin, everolimus, deforolimus), Akt inhibitors (e.g., perifosine, GSK-690693), Src inhibitors (e.g., dasatinib, bosutinib, XL-999, AZD-0530, KX010107), DNA methyltransferase inhibitors (e.g., 5-azacitidine, 5-aza-2'-deoxycitidine), cMET inhibitors (e.g., XL-880, ARQ-197, PF-02341066, JNJ-388, MGCD-265, SU-11724, PHA-665752, OA-5D5), farnesyl transferase inhibitors (e.g., tipifamib, lonafamib; BMS-214662), FTS inhibitors (e.g., tipifarnib, lonafarnib, BMS-214662), Raf inhibitors (sorafenib, RAF-265, XL-281, PLX-4032), MEK inhibitors (e.g., AZD-6244, RDEA-119, XL-518), IGF-1R antibodies (e.g., CP-721871, AMG-479, IMC-A12, R1507, BIIB022), IGF-1R inhibitors (e.g., XL-228, OSI-906, nordihydroguareacetic acid), HGF antibodies (e.g., AMG-102), PI3K inhibitors (e.g., PI-103, BGT-226, BEZ-235, XL-765, XL-147), HSP90 inhibitors (e.g., tanespimycin, retaspimycin, geldanamycin derivatives such as 17-AAG and 17-DMAG), TRAIL agonists (e.g., mapatumumab, AMG-655), survivin antagonists (e.g., YM-155, LY-2181308), PARP inhibitors (e.g., AG-014699, BSI-201), trabectidin, and dexamethasone. See, Ma W W and Adjei A A, *CA Cancer J Clin* 2009, 59:111-37 for more information on agents in development for cancer therapy.

Some specific anticancer agents that can be used as second agents in combination with a compound of Formula I or Formula II include, but are not limited to: azacitidine (5-azacitidine; e.g., Vidaza®); bortezomib (e.g., Velcade®); capecitabine (e.g., Xeloda®); carboplatin (e.g., Paraplatin®); cisplatin (e.g., Platinol®); cyclophosphamide (e.g., Cytoxan®, Neosar®); cytarabine (e.g., Cytosar®), cytarabine liposomal (e.g., DepoCyt®), cytarabine ocfosfate or other formulations of the active moiety; doxorubicin, doxorubicin hydrochloride (e.g., Adriamycin®), liposomal doxorubicin hydrochloride (e.g., Doxil®); fludarabine, fludarabine phosphate (Fludara®); 5-fluorouracil (e.g., Adrucil®); gefitinib (e.g., Iressa®); gemcitabine hydrochloride (e.g., Gemzar®); irinotecan (CPT-11, camptothecin-11), irinotecan hydrochloride (e.g., Camptosar®); lenalidomide (e.g., Revlimid®); melphalan (e.g., Alkeran®); paclitaxel (e.g., Taxol paclitaxel protein-bound (e.g., Abraxane®); rituximab (e.g., Rituxan®); vorinostat (e.g., Zolinza®).

Other anticancer agents that can be used as second agents in combination with a compound of Formula I or Formula II include, but are not limited to: α5β1 antibodies such as volociximab; αvβ3 antagonists such as vitaxin and cilengitide; acivicin; aclarubicin; acodazole hydrochloride; acronine; adalimumab (e.g., Humira®); adozelesin; alitretinoin (e.g., Panretin®); altretamine (hexamethylmelamine; e.g., Hexylen®); ambomycin; ametantrone acetate; aminoglutethimide (e.g., Cytadren®); amonafide malate (e.g., Xanafide®); amsacrine; anastrozole (e.g., Arimidex®); anthramycin; asparaginase (e.g., Kidrolase®, Elspar®); asperlin; azetepa; azotomycin; batimastat; benzodepa; bevacizumab (e.g., Avastin®); bexarotene (e.g., Targetin®); bicalutamide (e.g., Casodex®); bisantrene hydrochloride; bisnafide dimesylate; bizelesin; bleomycin sulfate (e.g., Blenoxane®); brequinar sodium; bropirimine; busulfan (e.g., Busulfex®, Myleran®); ; CD23 antibodies such as lumiliximab; CD52 antibodies such as alemtuzumab (e.g., Campath®); CD80 antibodies such as galiximab; cactinomycin; calusterone; caracemide; carbetimer; carmustine (e.g., BiCNU®); carmustine implant (e.g., Gliadel® wafer); carubicin hydrochloride; carzelesin; cedefingol; celecoxib (COX-2 inhibitor, e.g., Celebrex®); chlorambucil (e.g., Leukeran®); cirolemycin; cladribine (e.g., Leustatin®); clofarabine; cloretazine; crisnatol; crisnatol mesylate; 4-hydroperoxycyclo-phosphamide; dacarbazine (e.g., DTIC-Dome); dactinomycin (e.g., Cosmegen®); dasatanib (e.g., Sprycel®); daunorubicin hydrochloride (e.g., Cerubidine®), liposomal daunorubicin citrate (e.g., DaunoXome®); decitabine (5-aza-2'-deoxycitidine; e.g., Dacogen®); denileukin diftitox (e.g., Ontak®); dexormaplatin; dezaguanine, dezaguanine mesylate; diaziquone; droloxifene, droloxifene citrate; dromostanolone propionate; duazomycin; edatrexate; edrecolomab (Panorex®); eflornithine, eflornithine hydrochloride; elsamitrucin; enloplatin; enpromate; epipropidine; epirubicin hydrochloride (e.g., Ellence®); erbulozole; erlotinib (e.g., Tarceva®); esorubicin hydrochloride; estramustine, estramustine phosphate sodium (e.g., Emcyt®), estramustine analogues; etanidazole; etoposide (VP-16; e.g., Toposar®), etoposide phosphate (e.g., Etopophos®), etoprine; fadrozole hydrochloride; fazarabine; fenretinide; floxuridine (e.g., FUDR®); fluorocitabine; flutamide (e.g., Eulexin®); fosquidone; fostriecin, fostriecin sodium; G250 monoclonal antibody; galiximab; gemtuzumab ozogamicin (Mylotarg®); goserelin acetate (Zoladex®); hydroxyurea (e.g., Droxia®, Hydrea®); ibritumomab tiuxetan (e.g., Zevalin®)+$^{111}$In or $^{90}$Yt; idarubicin, darubicin, idarubicin hydrochloride (e.g., Idamycin®); ifosfamide (e.g., Ifex®) ilmofosine; iproplatin; lanreotide, lanreotide acetate; lapatinib (e.g., Tykerb®); letrozole (e.g., Femara®) leuprolide acetate (e.g., Eligard®, Viadur®); liarozole, liarozole hydrochloride; CD33 antibodies such as lintuzumab; lometrexol, lometrexol sodium; lomustine (e.g., CeeNu®); losoxantrone, losoxantrone hydrochloride; masoprocol; maytansine; mechlorethamine (nitrogen mustard, mustine), mechlorethamine hydrochloride (e.g., Mustargen®) megestrol acetate (e.g., Megace®) melengestrol acetate; menogaril; mercaptopurine (e.g., Purinethol®) methotrexate sodium (e.g., Rheumatrex®) metoprine; meturedepa; mitindomide; mitocarcin; mitocromin; mitogillin; mitomalcin; mitomycin (Mutamycin®) mitomycin analogues; mitosper; mitotane; mitoxantrone, mitoxantrone hydrochloride (e.g., Novantrone®) mycophenolic acid; nelarabine (Arranon®) nocodazole; nogalamycin; ormaplatin; oxisuran; panitumumab (e.g., Vectibix®); pegaspargase (PEG-L-asparaginase; e.g., Oncaspar®) peliomycin; pemetrexed (e.g., Alimta®); pentamustine; peplomycin sulfate; perfosfamide; pertuzumab (e.g., Omnitarg®) pipobroman; piposulfan; piroxantrone hydrochloride; plicamycin; plomestane; porfimer sodium; porfiromycin; prednimustine; procarbazine hydrochloride (e.g., Matulane®) puromycin; puromycin hydrochloride; pyrazofurin; R-roscovitine (seliciclib); riboprine; safingol; safingol hydrochloride; semustine; simtrazene; sorafenib (e.g., Nexavar®) sparfosate sodium; sparsomycin; spirogermanium hydrochloride; spiromustine; spiroplatin; streptonigrin; streptozocin (e.g., Zanosar®) sulofenur; sunitinib malate (e.g., Sutent®) talisomycin; tecogalan sodium; tegafur; teloxantrone hydrochloride; temoporfin; temozolomide (e.g., Temodar®); teniposide (e.g., Vumon®) teroxirone; testolactone; thalidomide (e.g., Thalomid®); thiamiprine; thioguanidine; 6-thioguanine; thiotepa (e.g., Thioplex®) tiazofurin; tipifarnib (e.g., Zarnestra®); tirapazamine; topotecan (e.g., Hycamtin®) toremifene, toremifene citrate (e.g., Fareston®); tositumomab+$^{131}$I (e.g., Bexxar®) trastuzumab (e.g., Herceptin®) trestolone acetate; triciribine, triciribine phosphate; trimetrexate, trimetrexate glucuronate; triptorelin; troxacitabine (e.g., Troxatyl®) tubulozole hydrochloride; uracil mustard; uredepa; vapreotide; verteporfin; vinblastine sulfate (e.g., Velban®) vincristine (leurocristine) sulfate (e.g., Vincasar®); vindesine, vindesine sulfate; vinepidine sulfate; vinglycinate sulfate; vinleurosine sulfate; vinorelbine tartrate (e.g., Navelbine®) vinrosidine sulfate; vinzolidine sulfate; vorozole; zeniplatin; zinostatin, zinostatin stimalamer; and zorubicin (rubidazone) hydrochloride.

Other anticancer agents that can be used in combination with a compound of Formula I or Formula II include, but are not limited to: 20-epi-1,25-dihydroxyvitamin D3; 5-ethynyluracil; abiraterone acetate; acylfulvene, (hydroxymethyl)acylfulvene; adecypenol; ALL-TK antagonists; ambamustine; amidox; amifostine; aminolevulinic acid; amrubicin; anagrelide (e.g., Agrylin®); andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; arsenic trioxide (e.g., Trisenox®); asulacrine; atamestane; atrimustine; axinastatin 1; axinastatin 2; axinastatin 3; azasetron; azatoxin; azatyrosine; baccatin III derivatives; balanol; BCR/ABL antagonists; benzochlorins; benzoylstaurosporine; beta lactam derivatives; beta-alethine; betaclamycin B; betulinic acid; bFGF inhibitor; bisantrene; bisaziridinylspermine; bisnafide; bistratene A; brefeldin A or its prodrug breflate; budotitane; buthionine sulfoximine; calcipotriol; calphostin C; camptothecin derivatives (e.g., irinotecan); carboxamide-amino-triazole; carboxyamido-triazole; CaRest M3; CARN 700; cartilage derived inhibitor; casein kinase inhibitors; castanospermine; cecropin B; cetrorelix; chlorins; chloroquinoxaline sulfonamide; cicaprost; cis-porphyrin; clarithromycin (e.g., Biaxin®); clomifene analogues; clotrimazole; collismycin A; collismycin B; combretastatin A4, combretastatin analogues; conagenin; crambescidin 816; cryptophycin 8; cryptophycin A derivatives; curacin A; cyclopentanthraquinones; cycloplatam; cypemycin; cytolytic factor; cytostatin; dacliximab (daclizumab; e.g., Zenapax®); dehydrodidemnin B; deslorelin; dexamethasone (e.g., Decadron®); dexifosfamide; dexrazoxane; dexverapamil; didemnin B; didox; diethylnorspermine; dihydro-5-azacytidine; 9-dihydrotaxol; dioxamycin; diphenyl; docetaxel (e.g., Taxotere®); docosanol; doxifluridine; duocarmycin SA; ebselen; ecomustine; edelfosine; edrecolomab; elemene; emitefur; epristeride; estrogen agonists; estrogen antagonists; exemestane (e.g., Aromasin®); fadrozole; filgrastim; finasteride; flavopiridol (alvocidib); flezelastine; fluasterone; fluorodaunorunicin hydrochloride; forfenimex; formestane; fotemustine; gadolinium texaphyrin; gallium nitrate; galocitabine; ganciclovir; ganirelix; gelatinase inhibitors; glutathione inhibitors; hepsulfam; heregulin; hexamethylene bisacetamide; hypericin; ibandronic acid; idoxifene; idramantone; ilomastat; imatinib, imatinib mesylate (e.g., Gleevec®); imiquimod (e.g., Aldara®), and other cytokine inducers; immunostimulant peptides; insulin-like growth factor-1 receptor inhibitor; interferon agonists; interferons such as interferon alpha (e.g., Intron® A); pegylated interferon alfa-2b (e.g., PegIntron®); interleukins such as IL-2 (aldesleukin, e.g., Proleukin®); IL-10, IL-12, and IL-18; iobenguane; iododoxorubicin; 4-ipomeanol; iroplact; irsogladine; isobengazole; isohomohalicondrin B; jasplakinolide; kahalalide F; lamellarin-N triacetate; leinamycin; lenograstim; lentinan sulfate; leptolstatin; leukemia inhibiting factor; leukocyte alpha interferon; leuprolide+estrogen+progesterone; leuprorelin; levamisole; linear polyamine analogue; lipophilic disaccharide peptide; lipophilic platinum compounds; lissoclinamide 7; lobaplatin; lombricine; lonidamine; loxoribine; lurtotecan; lutetium texaphyrin; lysofylline; lytic peptides; maitansine; mannostatin A; marimastat; maspin; matrilysin inhibitors; matrix metalloproteinase inhibitors; merbarone; meterelin; methioninase; metoclopramide; MIF inhibitor; mifepristone (e.g., Mifeprex®); miltefosine; mirimostim; mitoguazone; mitolactol; mitonafide; mitotoxin fibroblast growth factor-saporin; mofarotene; cetuximab (e.g., Erbitux®); human chorionic gonadotrophin; monophosphoryl lipid A+mycobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide (e.g., Nilandron®); nisamycin; nitric oxide modulators; nitroxide antioxidants (e.g., tempol); nitrullyn; oblimersen (Genasense®); O6-benzylguanine; octreotide (e.g., Sandostatin®); octreotide acetate (e.g., Sandostatin LAR®); okicenone; oligonucleotides; onapristone; oracin; osaterone; oxaliplatin (e.g., Eloxatin®); oxaunomycin; paclitaxel analogues; paclitaxel derivatives; palauamine; palmitoylrhizoxin; panaxytriol; panomifene; parabactin; pazelliptine; peldesine; pentosan polysulfate sodium; pentostatin (e.g., Nipent®); pentrozole; perflubron; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum-triamine complex; propyl bisacridone; prostaglandin J2; proteasome inhibitors; protein A-based immune modulator; protein kinase C inhibitors, including microalgal PKC inhibitors; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed (e.g., Tomudex®); ras farnesyl protein transferase inhibitors; ras inhibitors; ras-GAP inhibitor; retelliptine demethylated; rhenium (Re186); rhizoxin; ribozymes; RII retinamide; rohitukine; romurtide; roquinimex; rubiginone B1; ruboxyl; saintopin; SarCNU; sarcophytol A; Sdi 1 mimetics; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; splenopentin; spongistatin 1; squalamine; steroids (e.g., prednisone, prednisolone); stipiamide; stromelysin inhibitors; sulfinosine; sulindac; superactive vasoactive intestinal peptide antagonist; suradista; suramin; swainsonine; tallimustine; tamoxifen, tamoxifen citrate (e.g., Nolvadex®), tamoxifen methiodide; tauromustine; tazarotene; tellurapyrylium; telomerase inhibitors; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; titanocene bichloride; topsentin; translation inhibitors; tretinoin (all-trans retinoic acid, e.g., Vesanoid®); triacetyluridine; turosteride; tyrosine kinase inhibitors; tyrphostins; UBC inhibitors; ubenimex; urogenital sinus-derived growth inhibitory factor; urokinase receptor antagonists; variolin B; velaresol; veramine; verdins; vinxaltine; vitaxin; zanoterone; and zilascorb.

For a more comprehensive discussion of updated cancer therapies see, *The Merck Manual*, 18$^{th}$ Ed. 2006. See also the National Cancer Institute (NCI) website (http://www.cancer.gov/drugdictionary/) for a comprehensive list of oncology medications suitable as second active agents, and the US Food and Drug Administration (FDA) website for a list of the FDA-approved oncology medicaments.

In other embodiments, the second agent is a supportive care agent, such as an antiemetic agent or erythropoiesis stimulating agents. Specific antiemetic agents include, but are not limited to, phenothiazines, butyrophenones, benzodiazapines, corticosteroids, serotonin antagonists, cannabinoids, and NK1 receptor antagonists. Examples of phenothiazine antiemetic agents include, but are not limited to, prochlorperazine and trimethobenzamide. Examples of butyrophenone antiemetic agents include, but are not limited to, haloperidol. Examples of benzodiazapine antiemetic agents include, but are not limited to, lorazepam. Examples of corticosteroid antiemetic agents include, but are not limited to, dexamethasone. Examples of serotonin receptor (5-HT3 receptor) antagonist antiemetic agents include, but are not limited to, dolasetron mesylate (e.g., Anzemet®), granisetron (e.g., Kytril®), itasetron, ondansetron (e.g., Zofran®), palonosetron (e.g., Aloxi®) ramosetron, tropisetron (e.g., Navoban®), batanopride, dazopride, renzapride. Examples of cannabinoid antiemetic agents include, but are not limited to, dronabinol. Examples of NK1 receptor antagonists include, but are not limited to, aprepitant (e.g., Emend®).

Other supportive care second agents include agents that stimulate erythropoiesis or other hematopoietic processes, such as epoetin alfa (e.g., Epogen®, Procrit®); G-CSF and recombinant forms such as filgrastim (e.g., Neupogen®), pegfilgrastim (e.g., Neulasta®), and lenofilgrastim; darbepoetin alfa (e.g., Aranesp®); and GM-CSF and recombinant forms such as sargramostim (e.g., Leukine®) or molgramostim. Other supportive care agents include chemoprotectant agents such as amifostine (e.g., Ethyol®), dexrazoxane (e.g., Zinecard®), leucovorin (folinic acid), and mesna (e.g., Mesnex®); thrombopoeitic growth factors such as interleukin-11 (IL-11, oprelvekin, e.g., Neumega®); bisphosphonates such as pamidronate disodium (e.g., Aredia®), etidronate disodium (e.g., Didronel®) and zoledronic acid (e.g., Zometa®); and TNF antagonists, such as infliximab (e.g., Remicade®).

Tumor lysis syndrome (TLS) may be expected in the treatment of hematologic cancers, and supportive care treatment(s) to mitigate or prevent TLS or its component symptoms may be administered to patients treated with a compound of Formula I or Formula II according to the invention. Treatments suitable for preventing or mitigating TLS (or any of the symptoms thereof, including hyperkalemia, hyperphosphatemia, hyperuricemia, hypocalcemia, and acute renal failure), include, for example, allopurinol (e.g., Zyloprim®), rasburicase (e.g., Elitek®), and sodium polystyrene sulfonate (e.g., Kayexalate®).

Doses and dosing regimens of compounds of Formula I or Formula II together with other active second agents and combinations thereof should depend on the specific indication being treated, age and condition of a patient, and severity of adverse effects, and may be adjusted accordingly by those of skill in the art. Examples of doses and dosing regimens for other active moieties can be found, for example, in *Physician's Desk Reference*, and will require adaptation for use in the methods of the invention.

While the active moieties mentioned herein as second agents may be identified as free active moieties or as salt forms (including salts with hydrogen or coordination bonds) or other as non-covalent derivatives (e.g., chelates, complexes, and clathrates) of such active moieties, it is to be understood that the given representative commercial drug products are not limiting, and free active moieties, or salts or other derivative forms of the active moieties may alternatively be employed. Accordingly, reference to an active moiety should be understood to encompass not just the free active moiety but any pharmacologically acceptable salt or other derivative form that is consistent with the specified parameters of use.

6.8 Pharmaceutical Compositions and Dosage Forms

Provided herein are pharmaceutical compositions comprising a compound provided herein as an active ingredient, including a single enantiomer, a mixture of enantiomers, or a mixture of diastereomers thereof, or a pharmaceutically acceptable salt, solvate, or prodrug thereof; in combination with a pharmaceutically acceptable vehicle, carrier, diluent, excipient, or a mixture thereof.

The pharmaceutical compositions may be formulated in various dosage forms, including, but not limited to, the dosage forms for oral, parenteral, or topical administration. The pharmaceutical compositions may also be formulated as modified release dosage forms, including, but not limited to, delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, including a single enantiomer, a mixture of enantiomers, or a mixture of diastereomers thereof, or a pharmaceutically acceptable salt, solvate, or prodrug thereof; and a pharmaceutically acceptable vehicle, carrier, diluent, excipient, or a mixture thereof.

In another embodiment, the pharmaceutical compositions are provided in a dosage form for parenteral administration, which comprise a compound provided herein, including a single enantiomer, a mixture of enantiomers, or a mixture of diastereomers thereof, or a pharmaceutically acceptable salt, solvate, or prodrug thereof; and a pharmaceutically acceptable vehicle, carrier, diluent, excipient, or a mixture thereof.

In yet another embodiment, the pharmaceutical compositions are provided in a dosage form for topical administration, which comprise a compound provided herein, including a single enantiomer, a mixture of enantiomers, or a mixture of diastereomers thereof, or a pharmaceutically acceptable salt, solvate, or prodrug thereof; and a pharmaceutically acceptable vehicle, carrier, diluent, excipient, or a mixture thereof.

The pharmaceutical compositions provided herein may be provided in a unit- or multiple-dosage form. A unit-dosage form, as used herein, refers to a physically discrete unit suitable for administration to a subject, and packaged individually as is known in the art. Each unit-dose contains a predetermined quantity of the active ingredient(s) sufficient to produce the desired therapeutic effect, in association with the required pharmaceutically acceptable vehicle, carrier, diluent, excipient, or a mixture thereof. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include a vial, bottle of tablets or capsules, and bottle of pints or gallons.

The pharmaceutical compositions provided herein may be administered at once, or multiple times at intervals of time. It is understood that the dosage and duration of treatment suitable for a particular patient may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the pharmaceutical compositions provided herein.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In certain embodiments, the binder or filler is present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. In certain embodiments, the pharmaceutical compositions provided herein contain from about 0.5 to about 15% or from about 1 to about 5% by weight of a disintegrant.

Suitable lubricants include, but are not limited to, calcium stearate; magnesium stearate; sodium stearyl fumarate; mineral oil; light mineral oil; glycerin; sorbitol; mannitol; glycols, such as glycerol behenate and polyethylene glycol (PEG); stearic acid; stearyl fumaric acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. In certain embodiments, the pharmaceutical compositions provided herein contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Coloring agents include, but are not limited to, any of the approved, certified, water soluble FD&C dyes, water insoluble FD&C dyes suspended on alumina hydrate, and color lakes, and mixtures thereof. A color lake is the combination by adsorption of a water-soluble dye to a hydrous oxide of a heavy metal, resulting in an insoluble form of the dye. Flavoring agents include, but are not limited to, natural flavors extracted from plants, such as fruits, and synthetic blends of compounds which produce a pleasant taste sensation, such as peppermint and methyl salicylate. Sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include, but are not limited to, sodium carboxymethylcellulose, pectin, tragacanth, Vee-gum, acacia, sodium carbomethylcellulose, hydroxypropyl methylcellulose, and polyvinylpyrrolidone. Preservatives include, but are not limited to, glycerin, methyl and propylparaben, benzoic add, sodium benzoate and alcohol. Wetting agents include, but are not limited to, propylene glycol monostearate, sorbitan monooleate, diethylene glycol monolaurate, and polyoxyethylene lauryl ether. Solvents include, but are not limited to, glycerin, sorbitol, ethyl alcohol, and syrup. Examples of non-aqueous liquids utilized in emulsions include mineral oil and cottonseed oil. Organic acids include, but are not limited to, citric and tartaric acid. Sources of carbon dioxide include, but are not limited to, sodium bicarbonate and sodium carbonate.

It should be understood that a particular carrier or excipient may serve more than one function, even within the same formulation.

The pharmaceutical compositions provided herein may be provided as compressed tablets, tablet triturates, chewable lozenges, rapidly dissolving tablets, multiple compressed tablets, enteric coated tablets, sugar-coated tablets, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable taste or odor and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered, press-coated, and dry-coated tablets.

The tablet dosage forms may be prepared from the active ingredient in powdered, crystalline, or granular forms, alone or in combination with a pharmaceutically acceptable vehicle, carrier, diluent, or excipient, or a mixture thereof; including, e.g., a binder, disintegrant, controlled-release polymer, lubricant, diluent, and/or colorant. Flavoring and sweetening agents are especially useful in the formation of chewable tablets and lozenges.

The pharmaceutical compositions provided herein may be provided as soft or hard capsules, which can be made from, e.g., gelatin, methylcellulose, pullulan, starch, or calcium alginate. The hard gelatin capsule, also known as a dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including, but not limited to, methyl- and propyl-parabens and sorbic acid. The liquid, semisolid, and solid dosage forms provided herein may be encapsulated in a capsule. Suitable liquid and semisolid dosage forms include, but are not limited to, solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including, but not limited to, emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the form of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules or powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, and dextrose and lactated Ringer's injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations can be packaged in, e.g., an ampoule, a vial, or a syringe. In certain embodiments, the multiple dosage parenteral formulations contain an antimicrobial agent at bacteriostatic or fungistatic concentrations. In certain embodiments, the parenteral formulations provided herein are sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained-, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the form of ointments, creams, or gels. Suitable ointment vehicles include oleaginous or hydrocarbon vehicles, including lard, benzoinated lard, olive oil, cottonseed oil, and other oils; white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; and emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream bases can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout a liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. To prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the form of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; and glycerinated gelatin. Combinations of the various vehicles may be used. Rectal and vaginal suppositories may further comprise antioxidants as described herein, including bisulfite and sodium metabisulfite. Rectal and vaginal suppositories may be prepared by the compressed method or molding. The typical mass of a rectal and vaginal suppository is about 2 to about 3 g.

The pharmaceutical compositions provided herein may be administered ophthalmically in the form of solutions, suspensions, ointments, emulsions, gel-forming solutions, powders for solutions, gels, ocular inserts, or implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; or nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent, solvent or solvent system for dispersing, solubilizing, or extending release of the active ingredient provided herein; and/or a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of monohydrates. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavoring agent, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein is formulated in a modified release dosage form using an erodible matrix device, which can be water-swellable, erodible, and/or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In certain embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers; hydrophilic polymers, such as ethyl cellulose, cellulose acetate, crospovidone, and crosslinked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, or melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolate.

Another class of osmotic agents includes osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradual and continual release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating include, but are not limited to, plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters, poly-(methacrylic) acids and esters, and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during the coating process, as in the case of asymmetric membrane coatings as described in U.S. Pat. Nos. 5,612,059 and 5,698,220.

The total amount of the active ingredient(s) released and the release rate can be modulated by adjusting the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as an AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, or dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, those described in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the methods of use provided herein, may be made without departing from the spirit and scope thereof. Patents, patent publications, and other publications referenced herein are incorporated by reference.

7. EXAMPLES

All commercially available starting materials and solvents were reagent grade or better and used without further purification.

Synthesis of Compound A

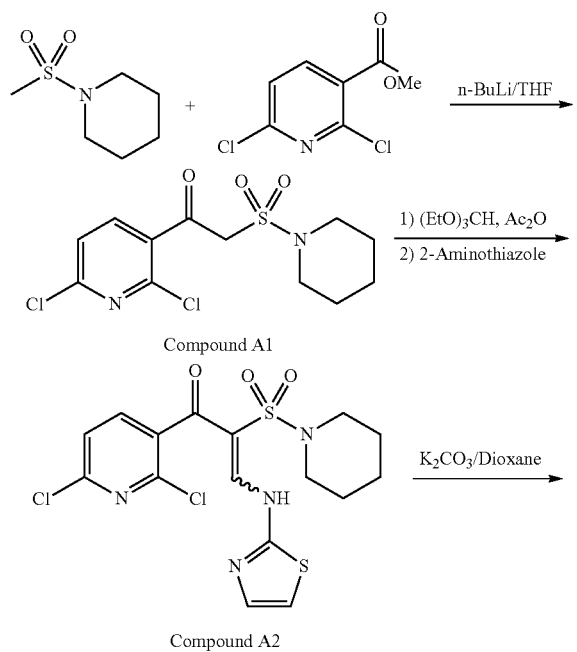

Compound A

Step-1: Synthesis of Compound A1

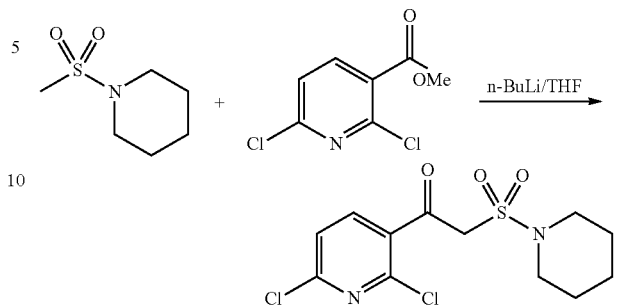

Compound A1

To a solution of N-methanesulfonylpiperidine (23.77 g, 145.6 mmol) in tetrahydrofuran (THF) (150 mL) at −78° C. was added n-butyllithium (2.6 M solution in hexanes, 56 mL, 145.6 mmol) dropwise and the reaction mixture was stirred at the same temperature for 1 hr. Then a solution of methyl 2,6-dichloropyridine-3-carboxylate (20 g, 97 mmol) in THF (150 mL) was added dropwise and the reaction mixture was stirred further for 2 hr during which time it was allowed to warm to room temperature. The reaction mixture was quenched with saturated ammonium chloride solution and then extracted with ethyl acetate (EtOAc). The organic layer was dried over sodium sulphate and concentrated to obtain the product as pale yellow solid (33 g).

1H NMR (300 MHz, CDCl$_3$): 8.0 (d, 8 Hz, 1H), 7.4 (d, 8 Hz, 1H), 4.6 (s, 2H), 3.3 (br t, 4 Hz, 4H), 1.7 (br s, 6H). LC/MS (M+H)$^+$ 337, 339

Step-2: Synthesis of Compound A2

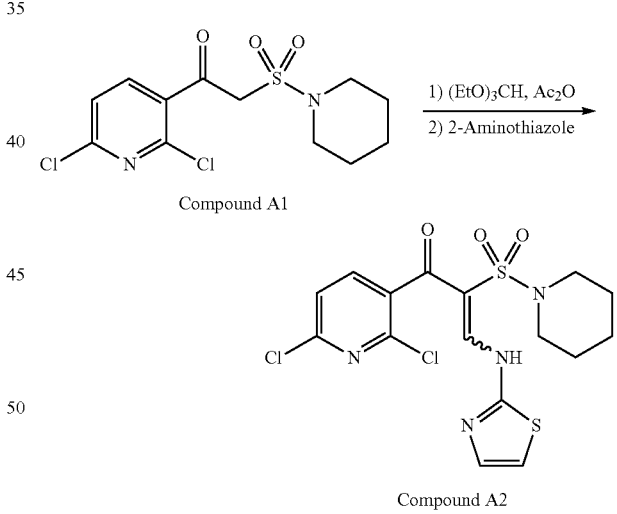

Compound A2

A mixture of Compound A1 (10 g, 29.6 mmol), triethylorthoformate (15 mL, 90 mmol) and acetic anhydride (21 mL, 222 mmol) was heated at 140° C. for 5 hr during which time the resulting EtOAc was distilled off under atmospheric pressure. Then it was concentrated under reduced pressure and the residue was diluted THF (60 mL). To this, 2-aminothiazole (3.27 g, 32.6 mmol) was added and then stirred at room temperature overnight. The reaction mixture was concentrated under reduced pressure and the residue was triturated with diethyl ether. The yellow solid obtained was collected by filtration, washed with diethyl ether and dried. Yield: 10.2 g (77%).

Step-3: Synthesis of Compound A

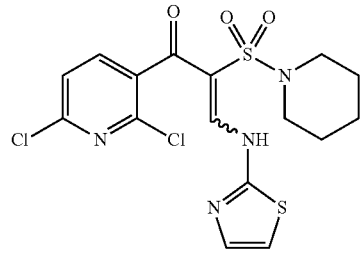

Compound A2

K₂CO₃/Dioxane

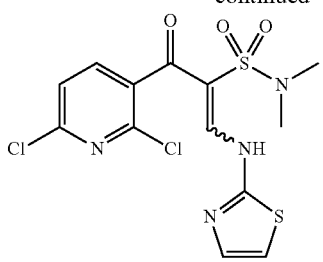

Compound B2

K₂CO₃/Dioxane

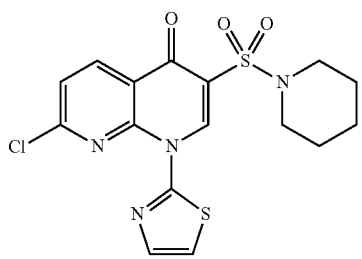

Compound A

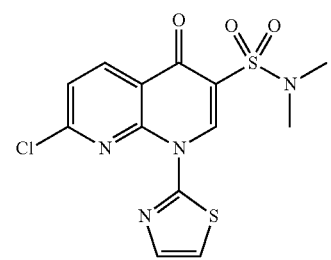

Compound B

Step-1: Synthesis of Compound B1

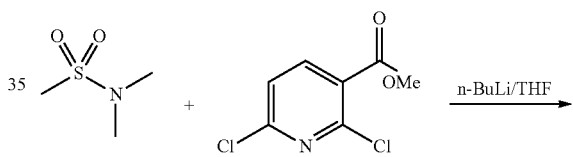

n-BuLi/THF

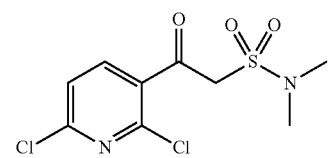

Compound B1

To a solution of Compound A2 (1.9 g, 4.25 mmol) in dioxane (20 mL) was added potassium carbonate (0.88 g, 6.37 mmol) and the reaction mixture was stirred at 60° C. for 1 hr. Then the reaction mixture was filtered to remove potassium carbonate and the filtrate was concentrated. The residue was partitioned in dichloromethane and water. The organic layer was separated, washed with water and brine, dried over sodium sulphate and concentrated. The residue was purified by column chromatography (silica gel 60-120 mesh) eluting with 0-15% EtOAc in petroleum ether to obtain the product as pale yellow solid. Yield: 1.2 g (68.7%).

1H NMR (300 MHz, CDCl₃): 10.0 (s, 1H), 8.7 (d, 8 Hz, 1H), 7.7 (d, 3.5 Hz, 1H), 7.5 (d, 8 Hz, 1H), 7.4 (d, 3.5 Hz, 1H), 3.4 (br s, 4H), 1.7 (br s, 6H). LC/MS (M+H)⁺ 411, 413

Synthesis of Compound B

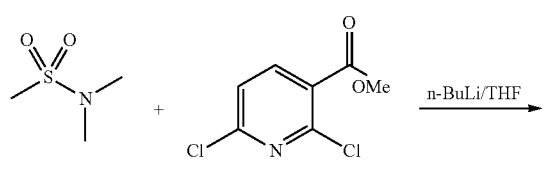

n-BuLi/THF

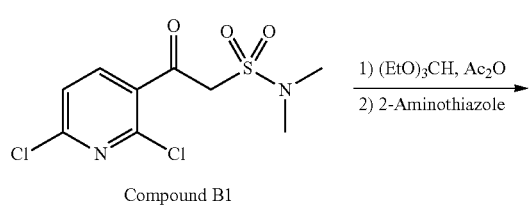

Compound B1

1) (EtO)₃CH, Ac₂O
2) 2-Aminothiazole

To a solution of N,N-dimethylmethanesulfonamide (18 g, 146 mmol) in THF (150 mL) at −78° C. was added n-butyllithium (2.6 M solution in hexanes, 56 mL, 145.6 mmol) dropwise and the reaction mixture was stirred at the same temperature for 1 hr. Then a solution of methyl 2,6-dichloropyridine-3-carboxylate (20 g, 97 mmol) in THF (150 mL) was added dropwise and the reaction mixture was stirred further for ~16 hr during which time it was allowed to warm to room temperature. The reaction mixture was quenched with saturated ammonium chloride solution and then extracted with EtOAc. The organic layer was dried over sodium sulphate and concentrated to obtain the product as pale yellow solid. The product was washed with diethyl ether and petroleum ether and dried under vacuum. Yield: 22 g (76%).

1H NMR (300 MHz, CDCl₃): 8.0 (d, 8 Hz, 1H), 7.4 (d, 8 Hz, 1H), 4.6 (s, 2H), 3.0 (s, 6H). LC/MS (M+H)⁺ 295, 297

Step-2: Synthesis of Compound B2

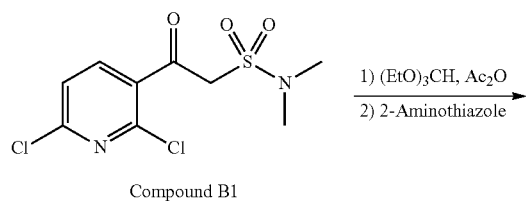

Compound B1

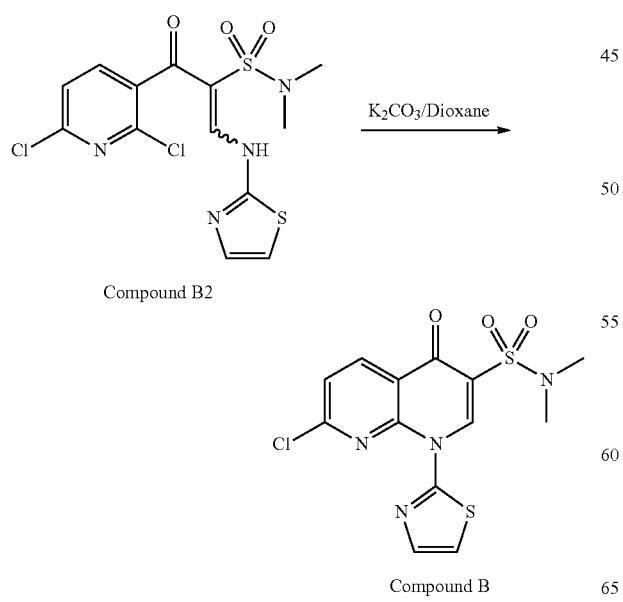

A mixture of Compound B1 (22 g, 74 mmol), triethylorthoformate (30 mL, 180 mmol) and acetic anhydride (45 mL, 476 mmol) was heated at 140° C. for 4 hr during which time the resulting EtOAc was distilled off under atmospheric pressure. Then it was concentrated under reduced pressure and the residue was taken in THF (120 mL). To this, 2-aminothiazole (8 g, 80 mmol) was added and then stirred at room temperature overnight. The reaction mixture was concentrated under reduced pressure and the residue was triturated with diethyl ether. The yellow solid obtained was collected by filtration, washed with diethyl ether and dried.

Yield: 23 g (76%).

Step-3: Synthesis of Compound B

To a solution of Compound B2 (23 g, 56.5 mmol) in dioxane (200 mL) was added potassium carbonate (8.6 g, 62.2 mmol) and the reaction mixture was stirred at 60° C. for 1 hr. Then the reaction mixture was filtered to remove potassium carbonate and the filtrate was concentrated. The residue was partitioned in dichloromethane and water. The organic layer was separated, washed with water and brine, dried over sodium sulphate and concentrated. The residue was purified by column chromatography (silica gel (60-120 mesh) eluting with 0-20% EtOAc in petroleum ether to obtain the product as pale yellow solid.

Yield: 18 g (86%).

1H NMR (300 MHz, CDCl$_3$): 10.0 (s, 1H), 8.7 (d, 8 Hz, 1H), 7.7 (d, 3.5 Hz, 1H), 7.5 (d, 8 Hz, 1H), 7.4 (d, 3.5 Hz, 1H), 3.0 (s, 6H). LC/MS (M+H)$^+$ 371, 373.

Synthesis of Compound C

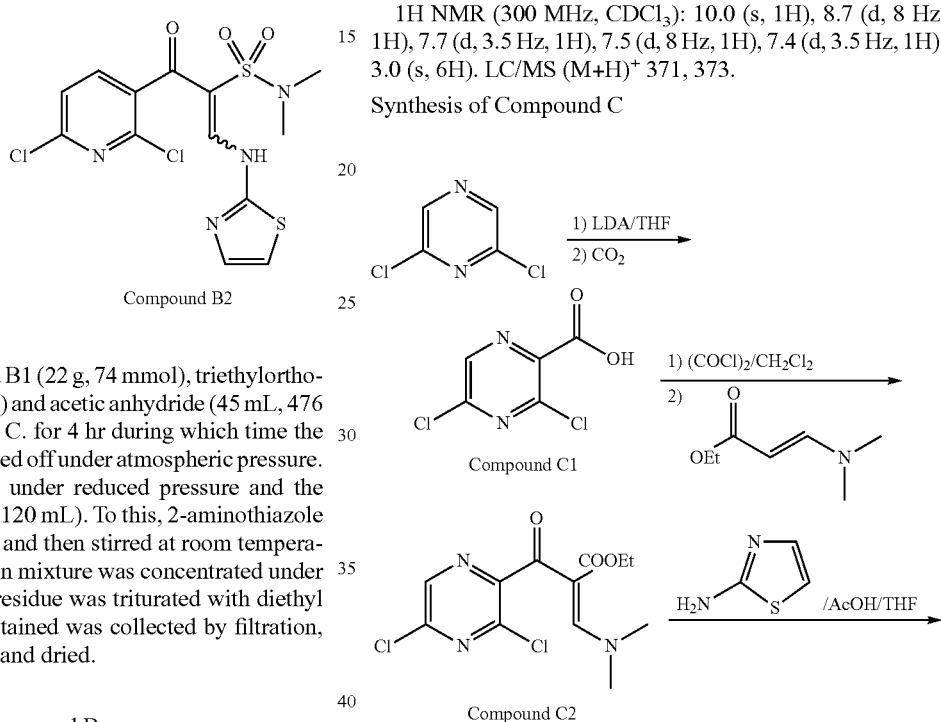

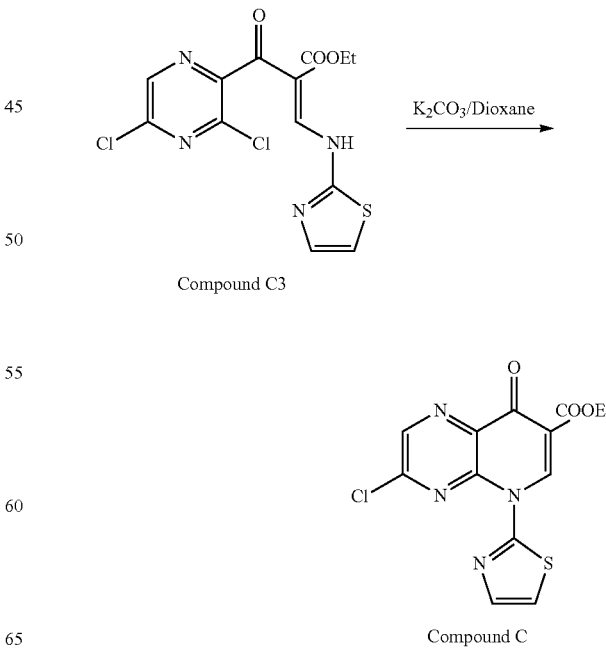

Step-1: Synthesis of Compound C1

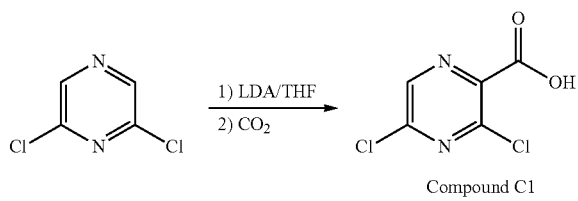 [SMILES: Clc1cncc(Cl)n1 ; O=C(O)c1ncc(Cl)nc1Cl]

Compound C1

To a solution of diisopropylamine (23.5 mL, 167.7 mmol) in THF (400 mL) at −20° C. was added n-butyllithium (1.6 M solution in hexanes, 104 mL, 166 mmol) dropwise and the reaction mixture was stirred at the same temperature for 30 minutes (min). Then the reaction mixture was cooled to −78° C. and a solution of 2,6-dichloropyrazine (10 g, 67 mmol) in THF (400 mL) was added drop wise over a period of 1.5 hr. The reaction mixture was stirred for additional 1 hr. Then the reaction mixture was poured on to dry ice and allowed to warm to room temperature over a period of ~16 hr. The reaction mixture was treated with 1.5 N HCl (~200 mL) and extracted with EtOAc. The EtOAc layer was extracted with saturated sodium bicarbonate solution; the aqueous layer was acidified with 1.5 N HCl, extracted with EtOAc, washed with brine and concentrated to obtain the product as pale yellow solid. The solid thus obtained was not purified further and used as such for the next step.

Yield: ~9 g (69.5%).

1H NMR (300 MHz, DMSO-d6): 8.9 (s, 1H)

Step-2: Synthesis of Compound C2

Compound C1

Compound C2

To a solution of 2,6-dichloropyrazine-3-carboxylic acid (9 g, 46.6 mmol) in dichloromethane (250 mL) at room temperature (RT) was added oxalyl chloride (5.2 mL, 61.5 mmol) dropwise followed by careful addition of DMF (3 drops) and then the reaction mixture was stirred at RT for 3 hr. Then it was concentrated in a rotavap and the residue was taken in toluene (150 mL) and added dropwise to a mixture of 3-dimethylaminoacrylic acid ethyl ester (8.5 g, 59.4 mmol) and triethylamine (9.7 mL, 69.5 mmol) and the resulting reaction mixture was stirred at 90° C. for 16 hr. Then the reaction mixture was cooled, filtered, and the filtrate was concentrated. The residue obtained was purified by column chromatography (silica gel 60-120 mesh) eluting with 0-40% EtOAc in petroleum ether to obtain the product as pale yellow solid.

Yield: 6.7 g (45%).

1H NMR (300 MHz, DMSO-d6): 8.8 (s, 1H), 8.0 (s, 1H), 3.8 (q, 5 Hz, 2H), 3.4 (s, 3H), 3.0 (s, 3H), 0.9 (t, 5 Hz, 3H). LC/MS (M+H)+ 318, 320

Step-3: Synthesis of Compound C3

Compound C2

Compound C3

To a solution of Compound C2 (11 g, 34.5 mmol) and 2-aminothiazole (3.4 g, 34 mmol) in THF (~130 mL) was added acetic acid (2 mL, 34.9 mmol) and the reaction mixture was stirred at room temperature for 18 hr. Then the reaction mixture was filtered and the filtrate was concentrated. The residue was partitioned in EtOAc and water. The organic layer was separated, dried over sodium sulphate and concentrated. The residue obtained was purified by column chromatography (silica gel 60-120 mesh) eluting with 0-15% EtOAc in petroleum ether to obtain the product as pale yellow solid.

Yield: 5.2 g (40.4%).

Step-4: Synthesis of Compound C

Compound C3

Compound C

To a solution of Compound C3 (5.2 g, 13.9 mmol) in dioxane (50 mL) was added potassium carbonate (2.9 g, 21 mmol) and the reaction mixture was stirred at 60° C. for 6 hr. Then the reaction mixture was filtered to remove potassium carbonate and the filtrate was concentrated. The residue was partitioned in chloroform and water; the organic layer was separated, dried over sodium sulphate and concentrated. The residue was triturated with methanol and the yellow solid obtained was collected by filtration and dried under vacuum.

Yield: 4.5 g (96%).

1H NMR (300 MHz, DMSO-d6): 9.7 (s, 1H), 9.1 (s, 1H), 7.9 (dd, 2.6 Hz, 2H), 4.3 (q, 5 Hz, 3H), 1.3 (t, 5 Hz, 3H). LC/MS (M+H)$^+$ 337, 339.

General Procedure for the Reaction of Compound A and Compound B with Amines

To a solution of Compound A or Compound B (0.25 g, 1 eqv) in acetonitrile (5-10 mL) at room temperature were added amine (1.5 eqv) and diisopropylethylamine (4 eqv. for free amines and 6 eqv. for amine salts) and the reaction mixture was heated to 80° C. On heating, the reaction mixture became clear and after ~15-30 min precipitation of pale yellow solid was observed. Heating was continued for 3 hr and then the reaction mixture was cooled. Then the solid obtained was collected by filtration, washed with acetonitrile and dried under vacuum.

The filtrate contains varying amounts of the product depending on their solubility in acetonitrile. No efforts were made to recover additional quantity of product from the filtrate as the first crop was sufficient enough for our purpose.

Example 1

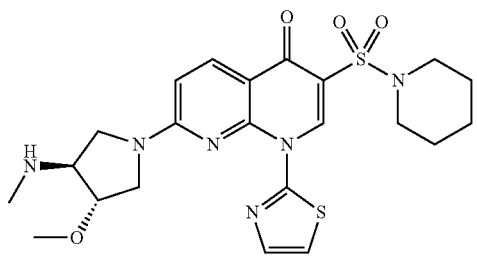 [SMILES: CN[C@H]1CN(c2ccc3c(=O)c(S(=O)(=O)N4CCCCC4)cn(-c4nccs4)c3n2)C[C@@H]1OC]

To a solution of Compound A (0.2 g, 0.48 mmol) in acetonitrile (5 mL) at room temperature were added diisopropylethylamine (0.5 mL, 2.87 mmol) and 595J (0.321 g, 0.68 mmol) and the reaction mixture was stirred 80° C. for 3 hr. Then heating was stopped and the reaction mixture was left aside overnight during which time precipitation of solid occurred. The solid obtained was collected by filtration, washed with acetonitrile and dried under vacuum. LC/MS: (M+H)$^+$: 505. An NMR spectrum is provided in FIG. 1.

Yield: 0.15 g (61%).

Example 2

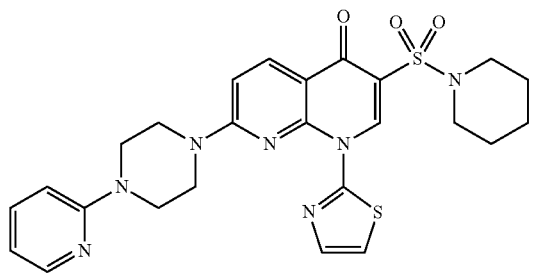 [SMILES: O=c1c(S(=O)(=O)N2CCCCC2)cn(-c2nccs2)c2nc(N3CCN(c4ccccn4)CC3)ccc12]

To a solution of Compound A (0.2 g, 0.48 mmol) in acetonitrile (5 mL) at room temperature were added diisopropylethylamine (0.34 mL, 1.95 mmol) and 1-(2-pyridyl)piperazine (0.119 g, 0.73 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 538. An NMR spectrum is provided in FIG. 2.

Yield: 0.16 g (61%).

Example 3

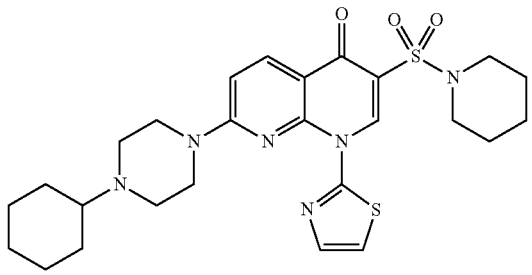 [SMILES: O=c1c(S(=O)(=O)N2CCCCC2)cn(-c2nccs2)c2nc(N3CCN(C4CCCCC4)CC3)ccc12]

To a solution of Compound A (0.2 g, 0.48 mmol) in acetonitrile (5 mL) at room temperature were added diisopropylethylamine (0.34 mL, 1.95 mmol) and 1-cyclohexylpiperazine (0.123 g, 0.73 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 543. An NMR spectrum is provided in FIG. 3.

Yield: 0.19 g (72%).

Example 4

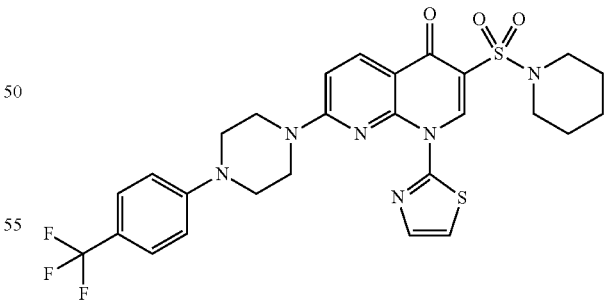

To a solution of Compound A (0.2 g, 0.48 mmol) in acetonitrile (5 mL) at room temperature were added diisopropylethylamine (0.34 mL, 1.95 mmol) and 1-(4-trifluoromethylphenyl)piperazine (0.168 g, 0.73 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 605. An NMR spectrum is provided in FIG. 4.

Yield: 0.13 g (44%).

Example 5

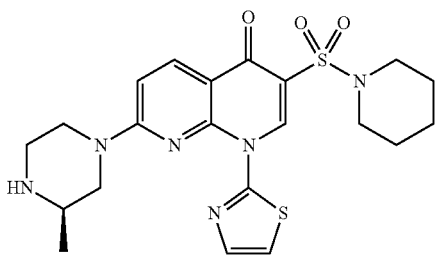 [SMILES: C[C@@H]1CN(c2ccc3c(=O)c(S(=O)(=O)N4CCCCC4)cn(-c4nccs4)c3n2)CCN1]

To a solution of Compound A (0.25 g, 0.60 mmol) in acetonitrile (5 mL) at room temperature were added diisopropylethylamine (0.42 mL, 2.4 mmol) and (R)-(−)-2-methylpiperazine (0.092 g, 0.92 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 475. An NMR spectrum is provided in FIG. 5.

Yield: 0.14 g (49%).

Example 6

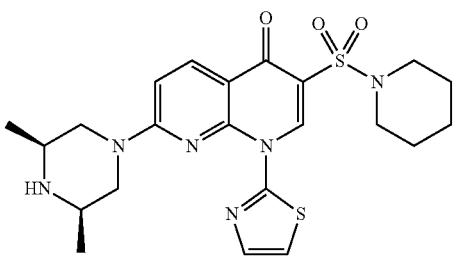 [SMILES: C[C@@H]1CN(c2ccc3c(=O)c(S(=O)(=O)N4CCCCC4)cn(-c4nccs4)c3n2)C[C@H](C)N1]

To a solution of Compound A (0.3 g, 0.73 mmol) in acetonitrile (6 mL) at room temperature were added diisopropylethylamine (0.5 mL, 2.9 mmol) and cis-2,6-dimethylpiperazine (0.125 g, 1.09 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 489. An NMR spectrum is provided in FIG. 6.

Yield: 0.26 g (73%).

Example 7

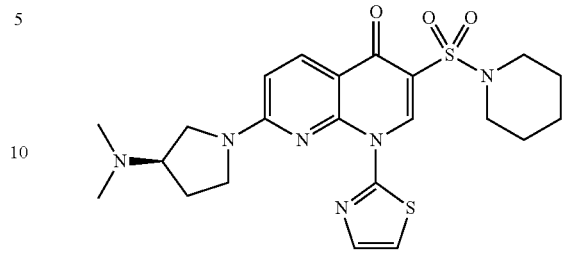

To a solution of Compound A (0.25 g, 0.60 mmol) in acetonitrile (5 mL) at room temperature were added diisopropylethylamine (0.42 mL, 2.4 mmol) and (R)-3-(dimethylamino)pyrrolidine (0.105 g, 0.92 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 489. An NMR spectrum is provided in FIG. 7.

Yield: 0.24 g (81%).

Example 8

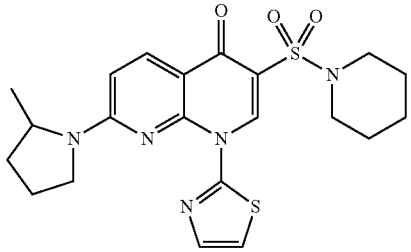 [SMILES: CC1CCCN1c1ccc2c(=O)c(S(=O)(=O)N3CCCCC3)cn(-c3nccs3)c2n1]

To a solution of Compound A (0.25 g, 0.60 mmol) in acetonitrile (5 mL) at room temperature were added diisopropylethylamine (0.42 mL, 2.4 mmol) and 2-methylpyrrolidine (0.077 g, 0.90 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 460. An NMR spectrum is provided in FIG. 8.

Yield: 0.21 g (75%).

Example 9

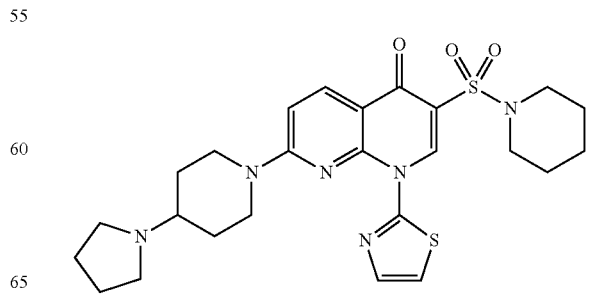

To a solution of Compound A (0.25 g, 0.60 mmol) in acetonitrile (5 mL) at room temperature were added diisopropylethylamine (0.42 mL, 2.4 mmol) and 4-(1-pyrrolidinyl)piperidine (0.14 g, 0.91 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 529. An NMR spectrum is provided in FIG. 9.

Yield: 0.24 g (75%).

Example 10

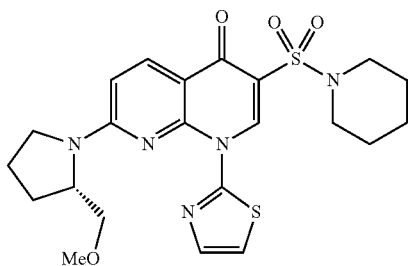 [SMILES: COC[C@@H]1CCCN1c1ccc2c(=O)c(S(=O)(=O)N3CCCCC3)cn(-c3nccs3)c2n1]

To a solution of Compound A (0.25 g, 0.60 mmol) in acetonitrile (6 mL) at room temperature were added diisopropylethylamine (0.42 mL, 2.4 mmol) and (S)-2-(methoxymethyl)pyrrolidine (0.105 g, 0.91 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 490. An NMR spectrum is provided in FIG. 10.

Yield: 0.21 g (70%).

Example 11

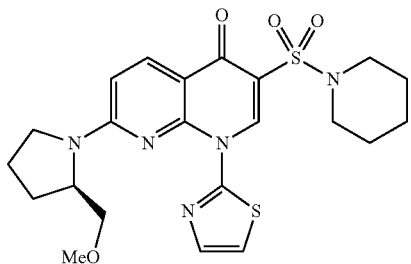 [SMILES: COC[C@H]1CCCN1c1ccc2c(=O)c(S(=O)(=O)N3CCCCC3)cn(-c3nccs3)c2n1]

To a solution of Compound A (0.25 g, 0.60 mmol) in acetonitrile (6 mL) at room temperature were added diisopropylethylamine (0.42 mL, 2.4 mmol) and (R)-2-(methoxymethyl)pyrrolidine (0.105 g, 0.91 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 490. An NMR spectrum is provided in FIG. 11.

Yield: 0.23 g (77%).

Example 12

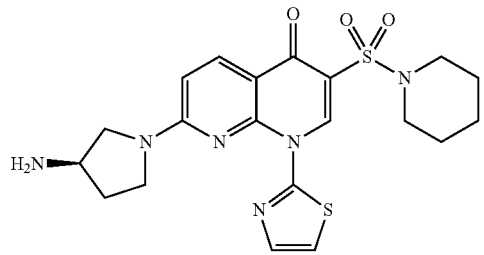 [SMILES: N[C@@H]1CCN(c2ccc3c(=O)c(S(=O)(=O)N4CCCCC4)cn(-c4nccs4)c3n2)C1]

To a solution of Compound A (0.25 g, 0.60 mmol) in acetonitrile (6 mL) at room temperature were added diisopropylethylamine (0.42 mL, 2.4 mmol) and (R)-3-aminopyrrolidine (0.079 g, 0.92 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 461. An NMR spectrum is provided in FIG. 12.

Yield: 0.27 g (96%).

Example 13

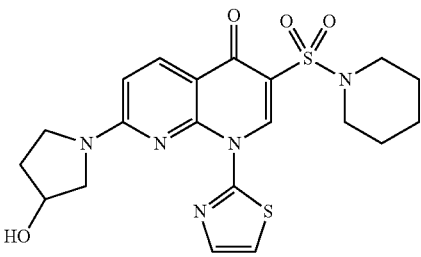 [SMILES: O=c1c(S(=O)(=O)N2CCCCC2)cn(-c2nccs2)c2nc(N3CCC(O)C3)ccc12]

To a solution of Compound A (0.25 g, 0.60 mmol) in acetonitrile (6 mL) at room temperature were added diisopropylethylamine (0.42 mL, 2.4 mmol) and 3-pyrrolidinol (0.08 g, 0.92 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)+: 462. An NMR spectrum is provided in FIG. 13.

Yield: 0.23 g (82%).

Example 14

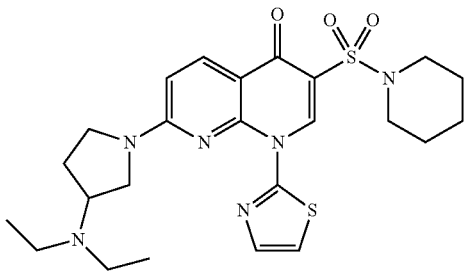 [SMILES: CCN(CC)C1CCN(c2ccc3c(=O)c(S(=O)(=O)N4CCCCC4)cn(-c4nccs4)c3n2)C1]

To a solution of Compound A (0.25 g, 0.60 mmol) in acetonitrile (6 mL) at room temperature were added diisopropylethylamine (0.42 mL, 2.4 mmol) and 3-(diethylamino)pyrrolidine (0.13 g, 0.91 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)⁺: 517. An NMR spectrum is provided in FIG. 14.

Yield: 0.3 g (95%).

Example 15

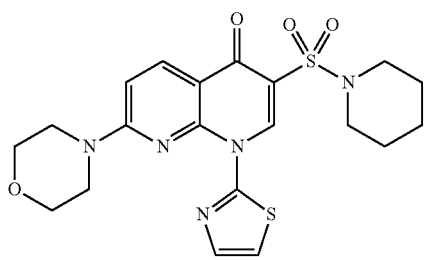 [SMILES: O=c1c(S(=O)(=O)N2CCCCC2)cn(-c2nccs2)c2nc(N3CCOCC3)ccc12]

To a solution of Compound A (0.25 g, 0.60 mmol) in acetonitrile (6 mL) at room temperature were added diisopropylethylamine (0.42 mL, 2.4 mmol) and morpholine (0.08 g, 0.92 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)⁺: 462. An NMR spectrum is provided in FIG. 15.

Yield: 0.26 g (93%).

Example 16

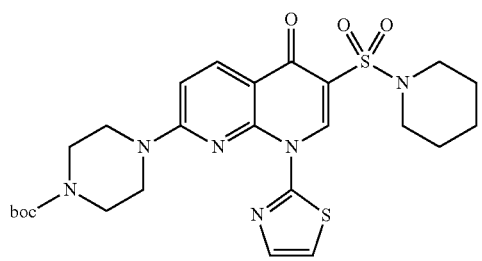

To a solution of Compound A (0.25 g, 0.60 mmol) in acetonitrile (6 mL) at room temperature were added diisopropylethylamine (0.42 mL, 2.4 mmol) and 1-boc-piperazine (0.17 g, 0.91 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)⁺: 561. An NMR spectrum is provided in FIG. 16.

Yield: 0.27 g (79%).

Example 17

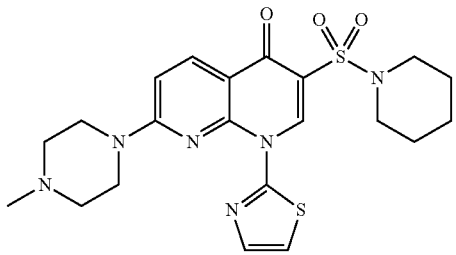 [SMILES: CN1CCN(c2ccc3c(=O)c(S(=O)(=O)N4CCCCC4)cn(-c4nccs4)c3n2)CC1]

To a solution of Compound A (0.25 g, 0.60 mmol) in acetonitrile (6 mL) at room temperature were added diisopropylethylamine (0.42 mL, 2.4 mmol) and 1-methylpiperazine (0.1 mL, 0.90 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)⁺: 475. An NMR spectrum is provided in FIG. 17.

Yield: 0.19 g (66%).

Example 18

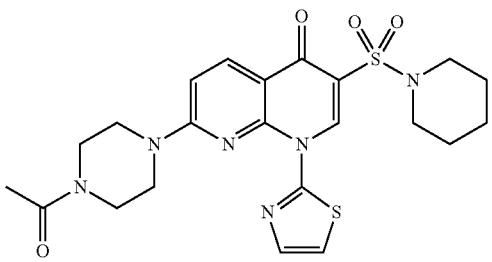 [SMILES: CC(=O)N1CCN(c2ccc3c(=O)c(S(=O)(=O)N4CCCCC4)cn(-c4nccs4)c3n2)CC1]

To a solution of Compound A (0.25 g, 0.60 mmol) in acetonitrile (6 mL) at room temperature were added diisopropylethylamine (0.42 mL, 2.4 mmol) and 1-acetylpiperazine (0.116 g, 0.90 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)⁺: 503. An NMR spectrum is provided in FIG. 18.

Yield: 0.26 g (85%).

Example 19

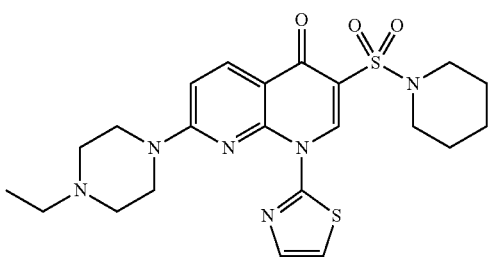 [SMILES: CCN1CCN(c2ccc3c(=O)c(S(=O)(=O)N4CCCCC4)cn(-c4nccs4)c3n2)CC1]

To a solution of Compound A (0.25 g, 0.60 mmol) in acetonitrile (6 mL) at room temperature were added diisopropylethylamine (0.42 mL, 2.4 mmol) and 1-ethylpiperazine (0.12 mL, 0.94 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 489. An NMR spectrum is provided in FIG. 19.

Yield: 0.16 g (54%).

Example 20

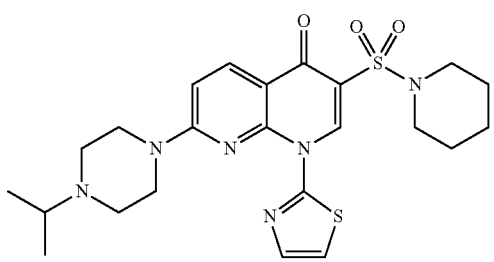

To a solution of Compound A (0.25 g, 0.60 mmol) in acetonitrile (6 mL) at room temperature were added diisopropylethylamine (0.42 mL, 2.4 mmol) and 1-isopropylpiperazine (0.117 g, 0.91 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 503. An NMR spectrum is provided in FIG. 20.

Yield: 0.19 g (62%).

Example 21

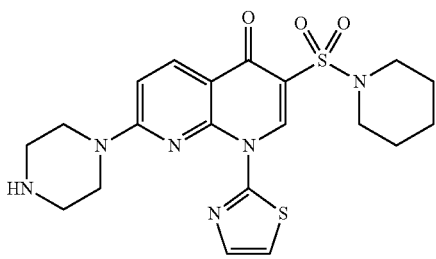 [SMILES: O=c1c(S(=O)(=O)N2CCCCC2)cn(-c2nccs2)c2nc(N3CCNCC3)ccc12]

To a solution of Compound A (0.25 g, 0.60 mmol) in acetonitrile (6 mL) at room temperature were added diisopropylethylamine (0.42 mL, 2.4 mmol) and piperazine (0.079 g, 0.92 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 461. An NMR spectrum is provided in FIG. 21.

Yield: 0.21 g (75%).

Example 22

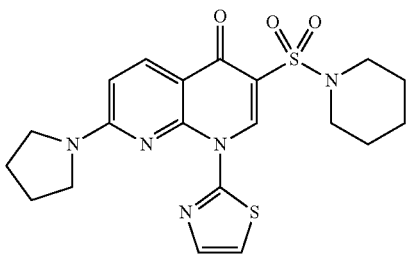 [SMILES: O=c1c(S(=O)(=O)N2CCCCC2)cn(-c2nccs2)c2nc(N3CCCC3)ccc12]

To a solution of Compound A (0.25 g, 0.60 mmol) in acetonitrile (6 mL) at room temperature were added diisopropylethylamine (0.42 mL, 2.4 mmol) and pyrrolidine (0.065 g, 0.90 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 446. An NMR spectrum is provided in FIG. 22.

Yield: 0.21 g (77%).

Example 23

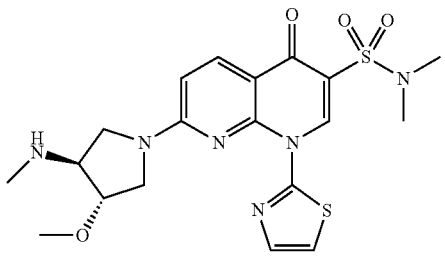

To a solution of Compound B (0.2 g, 0.54 mmol) in acetonitrile (5 mL) at room temperature were added diisopropylethylamine (0.6 mL, 3.44 mmol) and 595J (0.356 g, 0.75 mmol) and the reaction mixture was stirred 80° C. for 3 hr. Then heating was stopped and the reaction mixture was left aside overnight during which time precipitation of solid occurred. The solid obtained was collected by filtration, washed with acetonitrile and dried under vacuum. LC/MS: (M+H)$^+$: 465. An NMR spectrum is provided in FIG. 23.

Yield: 0.18 g (72%).

Example 24

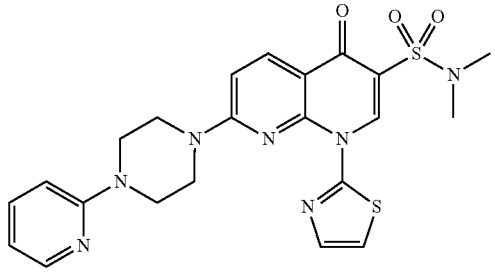 [SMILES: CN(C)S(=O)(=O)c1cn(-c2nccs2)c2nc(N3CCN(c4ccccn4)CC3)ccc2c1=O]

To a solution of Compound B (0.2 g, 0.54 mmol) in acetonitrile (5 mL) at room temperature were added diisopropylethylamine (0.4 mL, 2.3 mmol) and 1-(2-pyridyl)piperazine (0.132 g, 0.81 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 498. An NMR spectrum is provided in FIG. 24.

Yield: 0.21 g (78%).

Example 25

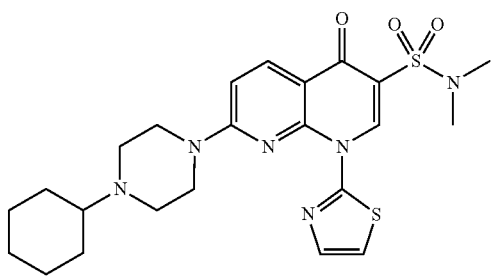 [SMILES: CN(C)S(=O)(=O)c1cn(-c2nccs2)c2nc(N3CCN(C4CCCCC4)CC3)ccc2c1=O]

To a solution of Compound B (0.2 g, 0.54 mmol) in acetonitrile (5 mL) at room temperature were added diisopropylethylamine (0.4 mL, 2.3 mmol) and 1-cyclohexylpiperazine (0.138 g, 0.82 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 503. An NMR spectrum is provided in FIG. 25.

Yield: 0.2 g (74%).

Example 26

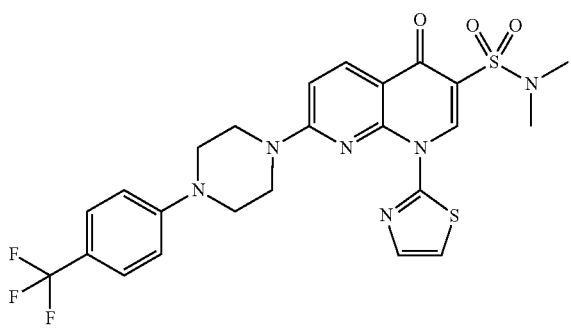 [SMILES: CN(C)S(=O)(=O)c1cn(-c2nccs2)c2nc(N3CCN(c4ccc(C(F)(F)F)cc4)CC3)ccc2c1=O]

To a solution of Compound B (0.2 g, 0.54 mmol) in acetonitrile (5 mL) at room temperature were added diisopropylethylamine (0.4 mL, 2.3 mmol) and 1-(4-trifluoromethylphenyl)piperazine (0.187 g, 0.81 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 565. An NMR spectrum is provided in FIG. 26.

Yield: 0.22 g (72%).

Example 27

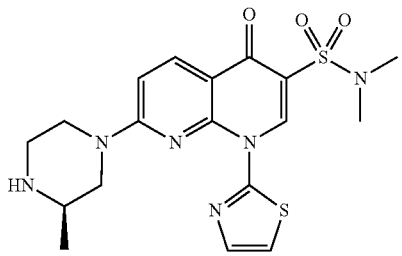 [SMILES: C[C@@H]1CN(c2ccc3c(=O)c(S(=O)(=O)N(C)C)cn(-c4nccs4)c3n2)CCN1]

To a solution of Compound B (0.2 g, 0.54 mmol) in acetonitrile (5 mL) at room temperature were added diisopropylethylamine (0.4 mL, 2.3 mmol) and (R)-(−)-2-methylpiperazine (0.081 g, 0.81 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 435. An NMR spectrum is provided in FIG. 27.

Yield: 0.13 g (55%).

Example 28

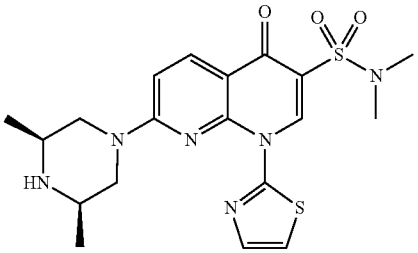

To a solution of Compound B (0.25 g, 0.67 mmol) in acetonitrile (6 mL) at room temperature were added diisopropylethylamine (0.5 mL, 2.9 mmol) and cis-2,6-dimethylpiperazine (0.115 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 449. An NMR spectrum is provided in FIG. 28.

Yield: 0.155 g (51%).

Example 29

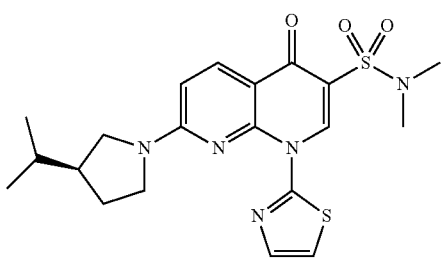 [SMILES: CC(C)[C@@H]1CCN(c2ccc3c(=O)c(S(=O)(=O)N(C)C)cn(-c4nccs4)c3n2)C1]

To a solution of Compound B (0.25 g, 0.67 mmol) in acetonitrile (6 mL) at room temperature were added diisopropylethylamine (0.5 mL, 2.9 mmol) and (R)-3-(dimethylamino)pyrrolidine (0.115 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 449. An NMR spectrum is provided in FIG. 29.

Yield: 0.24 g (79%).

Example 30

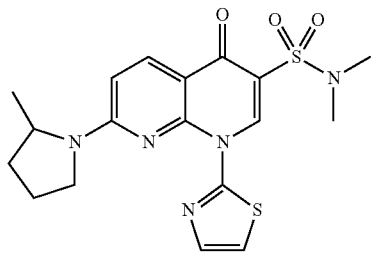 [SMILES: CC1CCCN1c1ccc2c(=O)c(S(=O)(=O)N(C)C)cn(-c3nccs3)c2n1]

To a solution of Compound B (0.25 g, 0.67 mmol) in acetonitrile (5 mL) at room temperature were added diisopropylethylamine (0.5 mL, 2.9 mmol) and 2-methylpyrrolidine (0.086 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 420. An NMR spectrum is provided in FIG. 30.

Yield: 0.21 g (74%).

Example 31

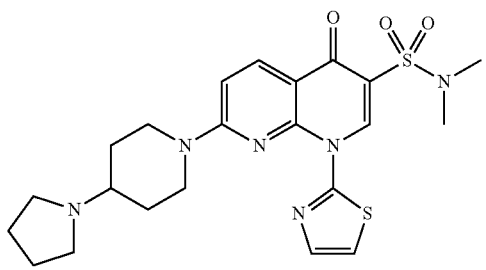 [SMILES: CN(C)S(=O)(=O)c1cn(-c2nccs2)c2nc(N3CCC(N4CCCC4)CC3)ccc2c1=O]

To a solution of Compound B (0.25 g, 0.67 mmol) in acetonitrile (5 mL) at room temperature were added diisopropylethylamine (0.5 mL, 2.9 mmol) and 4-(1-pyrrolidinyl)piperidine (0.156 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 489. An NMR spectrum is provided in FIG. 31.

Yield: 0.23 g (70%).

Example 32

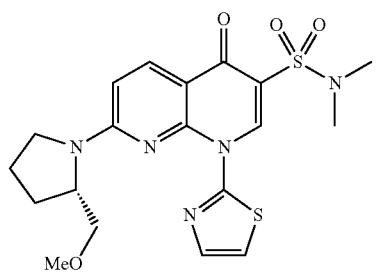 [SMILES: COC[C@@H]1CCCN1c1ccc2c(=O)c(S(=O)(=O)N(C)C)cn(-c3nccs3)c2n1]

To a solution of Compound B (0.25 g, 0.67 mmol) in acetonitrile (5 mL) at room temperature were added diisopropylethylamine (0.5 mL, 2.9 mmol) and (S)-2-(methoxymethyl)pyrrolidine (0.116 g, 1.0 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 450. An NMR spectrum is provided in FIG. 32.

Yield: 0.24 g (79%).

Example 33

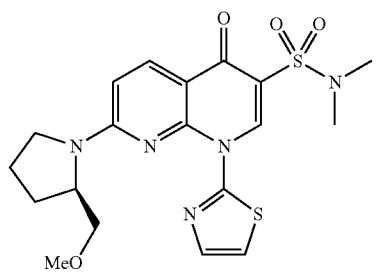 [SMILES: COC[C@H]1CCCN1c1ccc2c(=O)c(S(=O)(=O)N(C)C)cn(-c3nccs3)c2n1]

To a solution of Compound B (0.25 g, 0.67 mmol) in acetonitrile (5 mL) at room temperature were added diisopropylethylamine (0.5 mL, 2.9 mmol) and (R)-2-(methoxymethyl)pyrrolidine (0.116 g, 1.0 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 450. An NMR spectrum is provided in FIG. 33.

Yield: 0.23 g (76%).

Example 34

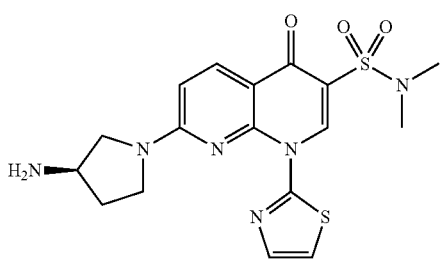 [SMILES: CN(C)S(=O)(=O)c1cn(-c2nccs2)c2nc(N3CC[C@@H](N)C3)ccc2c1=O]

To a solution of Compound B (0.25 g, 0.67 mmol) in acetonitrile (5 mL) at room temperature were added diisopropylethylamine (0.5 mL, 2.9 mmol) and (R)-3-aminopyrrolidine (0.087 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 421. An NMR spectrum is provided in FIG. 34.

Yield: 0.15 g (53%).

Example 35

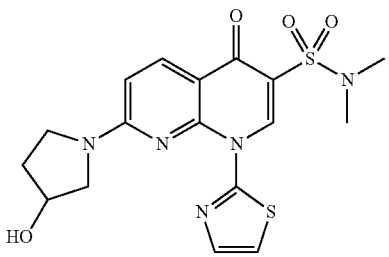 [SMILES: CN(C)S(=O)(=O)c1cn(-c2nccs2)c2nc(N3CCC(O)C3)ccc2c1=O]

To a solution of Compound B (0.25 g, 0.67 mmol) in acetonitrile (5 mL) at room temperature were added diisopropylethylamine (0.5 mL, 2.9 mmol) and 3-pyrrolidinol (0.088 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 422. An NMR spectrum is provided in FIG. 35.

Yield: 0.2 g (70%).

Example 36

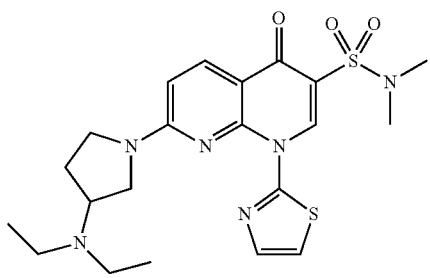 [SMILES: CCN(CC)C1CCN(c2ccc3c(=O)c(S(=O)(=O)N(C)C)cn(-c4nccs4)c3n2)C1]

To a solution of Compound B (0.25 g, 0.67 mmol) in acetonitrile (5 mL) at room temperature were added diisopropylethylamine (0.5 mL, 2.9 mmol) and 3-(diethylamino)pyrrolidine (0.144 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 477. An NMR spectrum is provided in FIG. 36.

Yield: 0.25 g (78%).

Example 37

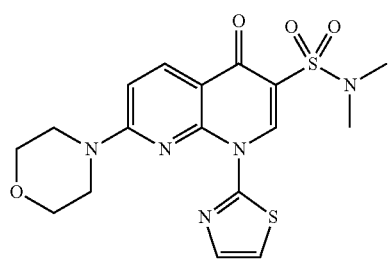 [SMILES: CN(C)S(=O)(=O)c1cn(-c2nccs2)c2nc(N3CCOCC3)ccc2c1=O]

To a solution of Compound B (0.25 g, 0.67 mmol) in acetonitrile (5 mL) at room temperature were added diisopropylethylamine (0.5 mL, 2.9 mmol) and morpholine (0.088 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 422. An NMR spectrum is provided in FIG. 37.

Yield: 0.24 g (84%).

Example 38

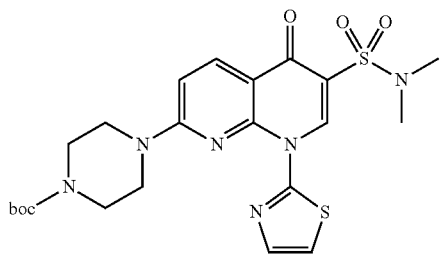

To a solution of Compound B (0.25 g, 0.67 mmol) in acetonitrile (5 mL) at room temperature were added diisopropylethylamine (0.5 mL, 2.9 mmol) and 1-boc-piperazine (0.189 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 521. An NMR spectrum is provided in FIG. 38.

Yield: 0.14 g (40%).

Example 39

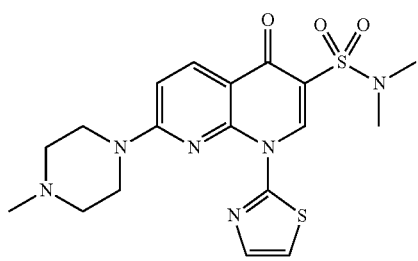

To a solution of Compound B (0.25 g, 0.67 mmol) in acetonitrile (5 mL) at room temperature were added diisopropylethylamine (0.5 mL, 2.9 mmol) and 1-methylpiperazine (0.102 g, 1.02 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 435. An NMR spectrum is provided in FIG. 39.

Yield: 0.125 g (43%).

Example 40

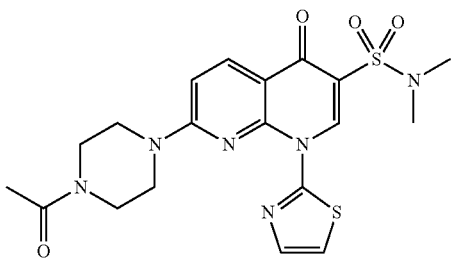 [SMILES: CC(=O)N1CCN(c2ccc3c(=O)c(S(=O)(=O)N(C)C)cn(-c4nccs4)c3n2)CC1]

To a solution of Compound B (0.25 g, 0.67 mmol) in acetonitrile (5 mL) at room temperature were added diisopropylethylamine (0.5 mL, 2.9 mmol) and 1-acetylpiperazine (0.13 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 463. An NMR spectrum is provided in FIG. 40.

Yield: 0.26 g (83%).

Example 41

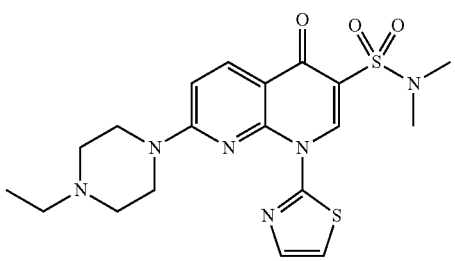 [SMILES: CCN1CCN(c2ccc3c(=O)c(S(=O)(=O)N(C)C)cn(-c4nccs4)c3n2)CC1]

To a solution of Compound B (0.25 g, 0.67 mmol) in acetonitrile (5 mL) at room temperature were added diisopropylethylamine (0.5 mL, 2.9 mmol) and 1-ethylpiperazine (0.115 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 449. An NMR spectrum is provided in FIG. 41.

Yield: 0.22 g (73%).

Example 42

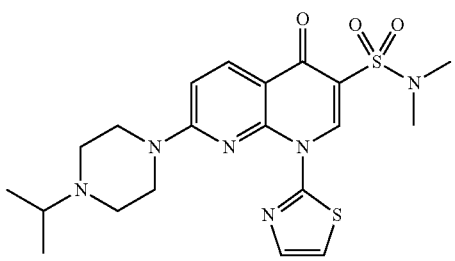 [SMILES: CC(C)N1CCN(c2ccc3c(=O)c(S(=O)(=O)N(C)C)cn(-c4nccs4)c3n2)CC1]

To a solution of Compound B (0.25 g, 0.67 mmol) in acetonitrile (5 mL) at room temperature were added diisopropylethylamine (0.5 mL, 2.9 mmol) and 1-isopropylpiperazine (0.13 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 463. An NMR spectrum is provided in FIG. 42.

Yield: 0.125 g (40%).

Example 43

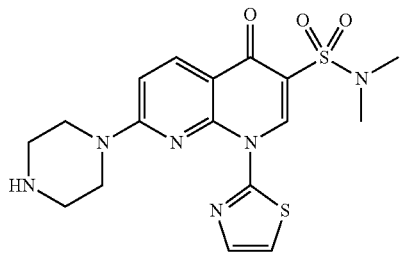 [SMILES: CN(C)S(=O)(=O)c1cn(-c2nccs2)c2nc(N3CCNCC3)ccc2c1=O]

To a solution of Compound B (0.25 g, 0.67 mmol) in acetonitrile (5 mL) at room temperature were added diisopropylethylamine (0.5 mL, 2.9 mmol) and piperazine (0.087 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 421. An NMR spectrum is provided in FIG. 43.

Yield: 0.21 g (74%).

Example 44

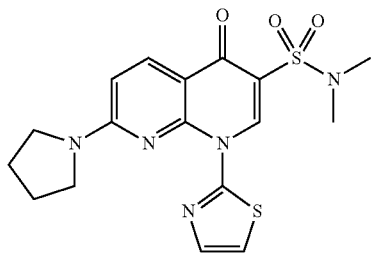 [SMILES: CN(C)S(=O)(=O)c1cn(-c2nccs2)c2nc(N3CCCC3)ccc2c1=O]

To a solution of Compound B (0.25 g, 0.67 mmol) in acetonitrile (5 mL) at room temperature were added diisopropylethylamine (0.5 mL, 2.9 mmol) and pyrrolidine (0.072 g, 1.01 mmol) and the reaction mixture was heated to 80° C. On heating, the reaction mixture became clear and after ~15 min commencement of precipitation of solid was observed. Heating was continued for 3 hr and then the reaction mixture was cooled. The solid obtained was collected by filtration, washed with acetonitrile and dried under vacuum. LC/MS: (M+H)$^+$: 406. An NMR spectrum is provided in FIG. 44.

Yield: 0.22 g (80%).

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A compound of Formula I:

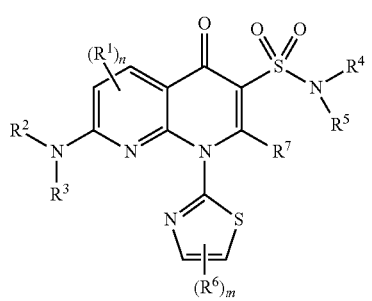

or a pharmaceutically acceptable salt thereof; wherein
R$^1$ is halo, alkyl, haloalkyl, alkoxy, or hydroxyl;
R$^2$ and R$^3$ together with the nitrogen atom on which they are substituted form a substituted or unsubstituted heterocyclic ring, where substituents when present are selected from one, two or three Q$^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;
R$^4$ and R$^5$ are selected as follows:
i) R$^4$ and R$^5$ are each alkyl, or
ii) R$^4$ and R$^5$ together with the nitrogen atom on which they are substituted form a substituted or unsubstituted heterocyclic ring; where substituents when present are selected from one or more Q$^2$ groups selected from halo, alkyl, haloalkyl, alkoxy, and hydroxyl;
R$^6$ is halo, alkyl, haloalkyl, alkoxy, or hydroxyl;
R$^7$ is hydrogen, halo, alkyl, haloalkyl, alkoxy, or hydroxyl;
n is 0 to 2;
m is 0 to 2; and
where Q$^1$ is optionally substituted with one, two or three groups selected from halo, alkyl, amino, alkoxy, hydroxyl, and haloalkyl.

2. The compound of claim 1, wherein R$^1$ is halo or alkyl;
R$^2$ and R$^3$ together with the nitrogen atom on which they are substituted form a substituted or unsubstituted heterocyclic ring, where substituents when present are selected from one, two or three Q$^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;
R$^4$ and R$^5$ are selected as follows:
i) R$^4$ and R$^5$ are each alkyl,
ii) R$^4$ and R$^5$ together with the nitrogen atom on which they are substituted form a substituted or unsubstituted 5 or 6 membered heterocyclic ring; where substituents when present are selected from one or two groups selected from halo and alkyl;
R$^6$ is halo, or alkyl;
R$^7$ is hydrogen, halo or alkyl;
n is 0 or 1; and
m is 0 or 1.

3. The compound of claim 1, wherein R$^2$ and R$^3$ together with the nitrogen atom on which they are substituted form pyrrolidinyl, piperidinyl, piperazinyl or morpholinyl ring, where substituents when present are selected from one, two or three Q$^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl.

4. The compound of claim 1, wherein Q$^1$ group is selected from methyl, ethyl, isopropyl, trifluoromethyl, amino, methylamino, dimethylamino, diethylamino, methoxy, methoxymethyl, hydroxyl, phenyl, trifluoromethylphenyl, cyclohexyl, piperidinyl, pyrrolidinyl, methylcarbonyl, and tert-butyloxycarbonyl.

5. The compound of claim 1, wherein R$^4$ and R$^5$ are each methyl.

6. The compound of claim 1, wherein the compound is of Formula IA

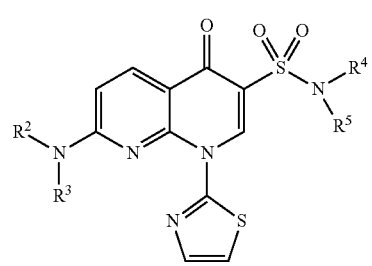

or a pharmaceutically acceptable salt thereof; wherein
R$^2$ and R$^3$ together with the nitrogen atom on which they are substituted form pyrrolidinyl, piperidinyl, piperazinyl or morpholinyl ring, where substituents when present are selected from one, two or three Q$^1$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl; and R⁴ and R⁵ are selected as follows:
i) R⁴ and R⁵ are each alkyl; or
ii) R⁴ and R⁵ together with the nitrogen atom on which they are substituted form an unsubstituted heterocyclic ring.

7. The compound of claim 1, wherein the compound is of Formula IB:

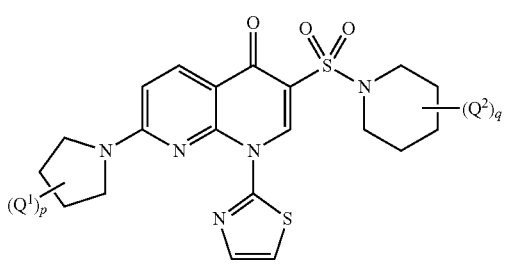

or a pharmaceutically acceptable salt thereof, wherein p is 0 to 3, q is 0 or 1; and Q¹ is amino, alkylamino, hydroxyl, alkoxy, or alkoxyalkyl.

8. The compound of claim 1, wherein the compound is of Formula IC:

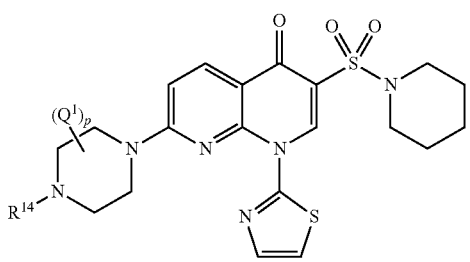

or a pharmaceutically acceptable salt thereof, wherein R¹⁴ is hydrogen, alkyl, haloalkyl, aryl, arylalkyl, alkylaryl, haloalkylaryl, alkylcarbonyl, cycloalkyl, haloalkylaryl, heteroaryl, heterocyclyl or alkyloxycarbonyl; Q¹ is alkyl; and p is 0, 1 or 2.

9. The compound of claim 1, wherein the compound is of Formula IG:

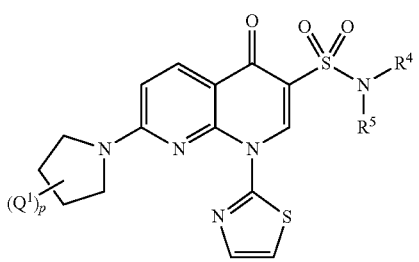

or a pharmaceutically acceptable salt thereof, wherein p is 0 to 3; Q¹ is amino, alkylamino, hydroxyl, alkoxy, or alkoxyalkyl; and R⁴ and R⁵ are each alkyl.

10. The compound of claim 1, wherein the compound is of Formula IH:

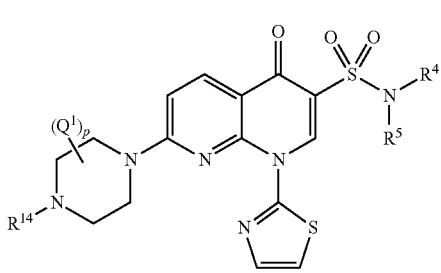

or a pharmaceutically acceptable salt thereof, wherein R¹⁴ is hydrogen, methyl, ethyl, isopropyl, trifluoromethyl, phenyl, methylcarbonyl, cyclohexyl, trifluoromethylphenyl, pyridinyl, pyrrolidinyl, piperidinyl or tert-butyloxycarbonyl; Q¹ is methyl; p is 0, 1 or 2; and R⁴ and R⁵ are each methyl.

11. A compound having Formula II:

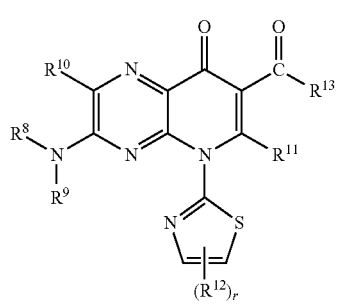

or a pharmaceutically acceptable salt thereof; wherein where R¹⁰ and R¹¹ are each independently hydrogen, halo, alkyl, haloalkyl, alkoxy, or hydroxyl;

R⁸ and R⁹ together with the nitrogen atom on which they are substituted form a substituted or unsubstituted heterocyclic ring, where substituents when present are selected from one or more Q³ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;

R¹² is halo, alkyl, haloalkyl, alkoxy, or hydroxyl;

R¹³ is hydroxyl or alkoxy;

r is 0 to 2; and where Q³ is optionally substituted with one, two or three groups selected from halo, alkyl, amino, alkoxy, hydroxyl, and haloalkyl.

12. The compound of claim 11, wherein R¹⁰ and R¹¹ are each independently hydrogen, halo or alkyl;

R⁸ and R⁹ together with the nitrogen atom on which they are substituted form a substituted or unsubstituted heterocyclic ring, where substituents when present are selected from one or more Q³ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl;

R¹² is halo or alkyl;

R¹³ is hydroxyl or alkoxy; and r is 0 or 1.

13. The compound of claim 12, wherein $R^8$ and $R^9$ together with the nitrogen atom on which they are substituted form a substituted or unsubstituted 5 or 6 membered heterocyclic ring, where substituents when present are selected from one, two or three $Q^3$ groups selected from alkyl, amino, alkylamino, alkoxy, hydroxyl, halo, haloalkyl, cycloalkyl, aryl, arylalkyl, alkylaryl, haloalkylaryl, heterocyclyl, heteroaryl, alkoxyalkyl, alkylcarbonyl, and alkoxycarbonyl.

14. The compound of claim 13, wherein $R^8$ and $R^9$ together with the nitrogen atom on which they are substituted form pyrrolidinyl, piperidinyl, piperazinyl or morpholinyl ring.

15. The compound of claim 11, wherein $R^{10}$ and $R^{11}$ are each hydrogen.

16. The compound of claim 1 selected from:

7-((3S,4S)-3-methoxy-4-(methylamino)pyrrolidin-1-yl)-3-(piperidin-1-ylsulfonyl)-1-(thiazol-2-yl)-1,8-naphthyridin-4(1H)-one;

3-(piperidin-1-ylsulfonyl)-7-(4-(pyridin-2-yl)piperazin-1-yl)-1-(thiazol-2-yl)-1,8-naphthyridin-4(1H)-one;

7-(4-cyclohexylpiperazin-1-yl)-3-(piperidin-1-ylsulfonyl)-1-(thiazol-2-yl)-1,8-naphthyridin-4(1H)-one;

3-(piperidin-1-ylsulfonyl)-1-(thiazol-2-yl)-7-(4-(4-(trifluoromethyl)phenyl)piperazin-1-yl)-1,8-naphthyridin-4(1H)-one;

(R)-7-(3-methylpiperazin-1-yl)-3-(piperidin-1-ylsulfonyl)-1-(thiazol-2-yl)-1,8-naphthyridin-4(1H)-one;

7-((3S,5R)-3,5-dimethylpiperazin-1-yl)-3-(piperidin-1-ylsulfonyl)-1-(thiazol-2-yl)-1,8-naphthyridin-4(1H)-one;

(R)-7-(3-(dimethylamino)pyrrolidin-1-yl)-3-(piperidin-1-ylsulfonyl)-1-(thiazol-2-yl)-1,8-naphthyridin-4(1H)-one;

7-(2-methylpyrrolidin-1-yl)-3-(piperidin-1-ylsulfonyl)-1-(thiazol-2-yl)-1,8-naphthyridin-4(1H)-one;

3-(piperidin-1-ylsulfonyl)-7-(4-(pyrrolidin-1-yl)piperidin-1-yl)-1-(thiazol-2-yl)-1,8-naphthyridin-4(1H)-one;

(S)-7-(2-(methoxymethyl)pyrrolidin-1-yl)-3-(piperidin-1-ylsulfonyl)-1-(thiazol-2-yl)-1,8-naphthyridin-4(1H)-one;

(R)-7-(2-(methoxymethyl)pyrrolidin-1-yl)-3-(piperidin-1-ylsulfonyl)-1-(thiazol-2-yl)-1,8-naphthyridin-4(1H)-one;

(R)-7-(3-aminopyrrolidin-1-yl)-3-(piperidin-1-ylsulfonyl)-1-(thiazol-2-yl)-1,8-naphthyridin-4(1H)-one;

7-(3-hydroxypyrrolidin-1-yl)-3-(piperidin-1-ylsulfonyl)-1-(thiazol-2-yl)-1,8-naphthyridin-4(1H)-one;

7-(3-(diethylamino)pyrrolidin-1-yl)-3-(piperidin-1-ylsulfonyl)-1-(thiazol-2-yl)-1,8-naphthyridin-4(1H)-one;

7-morpholino-3-(piperidin-1-ylsulfonyl)-1-(thiazol-2-yl)-1,8-naphthyridin-4(1H)-one;

tert-butyl 4-(5-oxo-6-(piperidin-1-ylsulfonyl)-8-(thiazol-2-yl)-5,8-dihydro-1,8-naphthyridin-2-yl)piperazine-1-carboxylate;

7-(4-methylpiperazin-1-yl)-3-(piperidin-1-ylsulfonyl)-1-(thiazol-2-yl)-1,8-naphthyridin-4(1H)-one;

7-(4-acetylpiperazin-1-yl)-3-(piperidin-1-ylsulfonyl)-1-(thiazol-2-yl)-1,8-naphthyridin-4(1H)-one;

7-(4-ethylpiperazin-1-yl)-3-(piperidin-1-ylsulfonyl)-1-(thiazol-2-yl)-1,8-naphthyridin-4(1H)-one;

7-(4-isopropylpiperazin-1-yl)-3-(piperidin-1-ylsulfonyl)-1-(thiazol-2-yl)-1,8-naphthyridin-4(1H)-one;

7-(piperazin-1-yl)-3-(piperidin-1-ylsulfonyl)-1-(thiazol-2-yl)-1,8-naphthyridin-4(1H)-one;

3-(piperidin-1-ylsulfonyl)-7-(pyrrolidin-1-yl)-1-(thiazol-2-yl)-1,8-naphthyridin-4(1H)-one;

7-((3S,4S)-3-methoxy-4-(methylamino)pyrrolidin-1-yl)-N,N-dimethyl-4-oxo-1-(thiazol-2-yl)-1,4-dihydro-1,8-naphthyridine-3-sulfonamide;

N,N-dimethyl-4-oxo-7-(4-(pyridin-2-yl)piperazin-1-yl)-1-(thiazol-2-yl)-1,4-dihydro-1,8-naphthyridine-3-sulfonamide;

7-(4-cyclohexylpiperazin-1-yl)-N,N-dimethyl-4-oxo-1-(thiazol-2-yl)-1,4-dihydro-1,8-naphthyridine-3-sulfonamide;

N,N-dimethyl-4-oxo-1-(thiazol-2-yl)-7-(4-(4-(trifluoromethyl)phenyl)piperazin-1-yl)-1,4-dihydro-1,8-naphthyridine-3-sulfonamide;

(R)—N,N-dimethyl-7-(3-methylpiperazin-1-yl)-4-oxo-1-(thiazol-2-yl)-1,4-dihydro-1,8-naphthyridine-3-sulfonamide;

7-((3S,5R)-3,5-dimethylpiperazin-1-yl)-N,N-dimethyl-4-oxo-1-(thiazol-2-yl)-1,4-dihydro-1,8-naphthyridine-3-sulfonamide;

(R)-7-(3-(dimethylamino)pyrrolidin-1-yl)-N,N-dimethyl-4-oxo-1-(thiazol-2-yl)-1,4-dihydro-1,8-naphthyridine-3-sulfonamide;

N,N-dimethyl-7-(2-methylpyrrolidin-1-yl)-4-oxo-1-(thiazol-2-yl)-1,4-dihydro-1,8-naphthyridine-3-sulfonamide;

N,N-dimethyl-4-oxo-7-(4-(pyrrolidin-1-yl)piperidin-1-yl)-1-(thiazol-2-yl)-1,4-dihydro-1,8-naphthyridine-3-sulfonamide;

(S)-7-(2-(methoxymethyl)pyrrolidin-1-yl)-N,N-dimethyl-4-oxo-1-(thiazol-2-yl)-1,4-dihydro-1,8-naphthyridine-3-sulfonamide;

(R)-7-(2-(methoxymethyl)pyrrolidin-1-yl)-N,N-dimethyl-4-oxo-1-(thiazol-2-yl)-1,4-dihydro-1,8-naphthyridine-3-sulfonamide;

(R)-7-(3-aminopyrrolidin-1-yl)-N,N-dimethyl-4-oxo-1-(thiazol-2-yl)-1,4-dihydro-1,8-naphthyridine-3-sulfonamide;

7-(3-hydroxypyrrolidin-1-yl)-N,N-dimethyl-4-oxo-1-(thiazol-2-yl)-1,4-dihydro-1,8-naphthyridine-3-sulfonamide;

7-(3-(diethylamino)pyrrolidin-1-yl)-N,N-dimethyl-4-oxo-1-(thiazol-2-yl)-1,4-dihydro-1,8-naphthyridine-3-sulfonamide;

N,N-dimethyl-7-morpholino-4-oxo-1-(thiazol-2-yl)-1,4-dihydro-1,8-naphthyridine-3-sulfonamide;

tert-butyl 4-(6-(N,N-dimethylsulfamoyl)-5-oxo-8-(thiazol-2-yl)-5,8-dihydro-1,8-naphthyridin-2-yl)piperazine-1-carboxylate;

N,N-dimethyl-7-(4-methylpiperazin-1-yl)-4-oxo-1-(thiazol-2-yl)-1,4-dihydro-1,8-naphthyridine-3-sulfonamide;

7-(4-acetylpiperazin-1-yl)-N,N-dimethyl-4-oxo-1-(thiazol-2-yl)-1,4-dihydro-1,8-naphthyridine-3-sulfonamide;

7-(4-ethylpiperazin-1-yl)-N,N-dimethyl-4-oxo-1-(thiazol-2-yl)-1,4-dihydro-1,8-naphthyridine-3-sulfonamide;

7-(4-isopropylpiperazin-1-yl)-N,N-dimethyl-4-oxo-1-(thiazol-2-yl)-1,4-dihydro-1,8-naphthyridine-3-sulfonamide;

N,N-dimethyl-4-oxo-7-(piperazin-1-yl)-1-(thiazol-2-yl)-1,4-dihydro-1,8-naphthyridine-3-sulfonamide; and N,N-dimethyl-4-oxo-7-(pyrrolidin-1-yl)-1-(thiazol-2-yl)-1,4-dihydro-1,8-naphthyridine-3-sulfonamide.

17. A pharmaceutical composition comprising a compound of claim 1 and a pharmaceutically acceptable carrier.

18. The compound of claim 11 selected from:
3-((3S,4S)-3-methoxy-4-(methylamino)pyrrolidin-1-yl)-8-oxo-5-(thiazol-2-yl)-5,8-dihydropyrido[3,2-b]pyrazine-7-carboxylic acid;
(S)-3-(3-(dimethylamino)pyrrolidin-1-yl)-8-oxo-5-(thiazol-2-yl)-5,8-dihydropyrido[3,2-b]pyrazine-7-carboxylic acid;
(S)-3-(3-aminopyrrolidin-1-yl)-8-oxo-5-(thiazol-2-yl)-5,8-dihydropyrido[3,2-b]pyrazine-7-carboxylic acid;
3-(3-methoxypyrrolidin-1-yl)-8-oxo-5-(thiazol-2-yl)-5,8-dihydropyrido[3,2-b]pyrazine-7-carboxylic acid;
3-(3-hydroxypyrrolidin-1-yl)-8-oxo-5-(thiazol-2-yl)-5,8-dihydropyrido[3,2-b]pyrazine-7-carboxylic acid;
3-(3-(diethylamino)pyrrolidin-1-yl)-8-oxo-5-(thiazol-2-yl)-5,8-dihydropyrido[3,2-b]pyrazine-7-carboxylic acid;
8-oxo-3-(pyrrolidin-1-yl)-5-(thiazol-2-yl)-5,8-dihydropyrido[3,2-b]pyrazine-7-carboxylic acid;
3-(2-methylpyrrolidin-1-yl)-8-oxo-5-(thiazol-2-yl)-5,8-dihydropyrido[3,2-b]pyrazine-7-carboxylic acid;
(R)-3-(2-(methoxymethyl)pyrrolidin-1-yl)-8-oxo-5-(thiazol-2-yl)-5,8-dihydropyrido[3,2-b]pyrazine-7-carboxylic acid;
(S)-3-(2-(methoxymethyl)pyrrolidin-1-yl)-8-oxo-5-(thiazol-2-yl)-5,8-dihydropyrido[3,2-b]pyrazine-7-carboxylic acid;
3-(4-methylpiperazin-1-yl)-8-oxo-5-(thiazol-2-yl)-5,8-dihydropyrido[3,2-b]pyrazine-7-carboxylic acid;
3-(4-ethylpiperazin-1-yl)-8-oxo-5-(thiazol-2-yl)-5,8-dihydropyrido[3,2-b]pyrazine-7-carboxylic acid;
3-(4-acetylpiperazin-1-yl)-8-oxo-5-(thiazol-2-yl)-5,8-dihydropyrido[3,2-b]pyrazine-7-carboxylic acid;
3-(4-cyclohexylpiperazin-1-yl)-8-oxo-5-(thiazol-2-yl)-5,8-dihydropyrido[3,2-b]pyrazine-7-carboxylic acid;
8-oxo-3-(piperazin-1-yl)-5-(thiazol-2-yl)-5,8-dihydropyrido[3,2-b]pyrazine-7-carboxylic acid;
3-((3S,5R)-3,5-dimethylpiperazin-1-yl)-8-oxo-5-(thiazol-2-yl)-5,8-dihydropyrido[3,2-b]pyrazine-7-carboxylic acid;
(R)-3-(3-methylpiperazin-1-yl)-8-oxo-5-(thiazol-2-yl)-5,8-dihydropyrido[3,2-b]pyrazine-7-carboxylic acid;
8-oxo-5-thiazol-2-yl)-3-(4-(4-trifluoromethyl)phenyl)piperazin-1-yl)-5,8-dihydropyrido[3,2-b]pyrazine-7-carboxylic acid;
3-(4-isopropylpiperazin-1-yl)-8-oxo-5-(thiazol-2-yl)-5,8-dihydropyrido[3,2-b]pyrazine-7-carboxylic acid;
3-morpholino-8-oxo-5-(thiazol-2-yl)-5,8-dihydropyrido[3,2-b]pyrazine-7-carboxylic acid;
8-oxo-3-(4-(pyridin-2-yl)piperazin-1-yl)-5-(thiazol-2-yl)-5,8-dihydropyrido[3,2-b]pyrazine-7-carboxylic acid;
8-oxo-3-(4-(pyrrolidin-1-yl)piperidin-1-yl)-5-(thiazol-2-yl)-5,8-dihydropyrido[3,2-b]pyrazine-7-carboxylic acid; and
3-(4-tert-butoxycarbonyl)piperazin-1-yl)-8-oxo-5-(thiazol-2-yl)-5,8-dihydropyrido[3,2-b]pyrazine-7-carboxylic acid.

19. A pharmaceutical composition comprising a compound of claim 11 and a pharmaceutically acceptable carrier.

* * * * *